US008877730B2

(12) United States Patent
Stoffel et al.

(10) Patent No.: US 8,877,730 B2
(45) Date of Patent: *Nov. 4, 2014

(54) TARGETING MICRORNAS FOR METABOLIC DISORDERS

(71) Applicant: ETH Zurich, Zurich (CH)

(72) Inventors: Markus Stoffel, Herrliberg (CH); Mirko Trajkovski, Zurich (CH)

(73) Assignee: ETH Zurich, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/061,365

(22) Filed: Oct. 23, 2013

(65) Prior Publication Data

US 2014/0113953 A1  Apr. 24, 2014

Related U.S. Application Data

(63) Continuation of application No. 13/320,873, filed as application No. PCT/IB2010/001384 on May 19, 2010, now Pat. No. 8,592,388.

(60) Provisional application No. 61/322,878, filed on Apr. 11, 2010, provisional application No. 61/180,024, filed on May 20, 2009.

(51) Int. Cl.
*A61K 48/00* (2006.01)
*C07H 21/02* (2006.01)
*C07H 21/04* (2006.01)
*C12N 15/11* (2006.01)

(52) U.S. Cl.
USPC ..................................... 514/44 A; 536/24.5

(58) Field of Classification Search
USPC ......................................................... 514/44
See application file for complete search history.

(56) References Cited

U.S. PATENT DOCUMENTS 8,592,388 B2 * 11/2013 Stoffel et al. ............... 514/44 A
2006/0058266 A1   3/2006 Manoharan et al.

FOREIGN PATENT DOCUMENTS

| WO | WO 2005/013901 | 2/2005 |
| WO | 2005118806 A2 | 12/2005 |
| WO | 2006137941 A2 | 12/2006 |
| WO | 2007090073 A2 | 8/2007 |
| WO | 2007112753 A2 | 10/2007 |
| WO | WO 2007/112754 | 10/2007 |
| WO | WO 2009/043353 | 4/2009 |

OTHER PUBLICATIONS

Esau et al., "MicroRNA-143 Regulates Adipocyte Differentiation," J Biol Chem, 2004, 279(50):52361-52365.
Greenfield and Chisholm, "Thiazolidinediones—mechanisms of action," Australian Prescriber, 2004, 27:67-70.

(Continued)

*Primary Examiner* — Terra Cotta Gibbs
(74) *Attorney, Agent, or Firm* — Casimir Jones, S.C.

(57) ABSTRACT

Provided herein are methods and compositions for the treatment of metabolic disorders. Also provided herein are methods and compositions for the reduction of blood glucose level, the reduction of gluceoneogenesis, the improvement of insulin resistance and the reduction of plasma cholesterol level. In certain embodiments, the methods comprise inhibiting the activity of miR-103. In certain embodiments, the methods comprise inhibiting the activity of miR-107. In certain embodiments, the activity of both miR-103 and miR-107 is inhibited. In certain embodiments, such methods comprise administering a compound comprising an oligonucleotide targeted to a microRNA.

21 Claims, 9 Drawing Sheets

(56) References Cited

OTHER PUBLICATIONS

Herrera et al. "Global microRNA expression profiles in insulin target tissues in a spontaneous rat model of type 2 diabetes." Diabetologia, 2010, 53:1099-1109.

Jin et al. "MicroRNA expression pattern in different stages of non-alcoholic fatty liver disease." Dig Liver Dis, 2009, 41:289-297.

Kajimoto et al., "MicroRNA and 3T3-L1 pre-adipocyte differentiation," RNA, 2006, 12:1-7.

Regulus Therapeutics Inc., "Regulus Therapeutics Inc. presents: 'MicroRNA: The Year in Review and a Look Ahead,'" Press Release, Dec. 9, 2009, 3 pages.

Regulus Therapeutics Inc., "MicrRNA: The Year in Review and a Look Ahead," Regulus Webinar Series, presented Dec. 14, 2009, 42 pages.

Macisaac, "Clinical indications for thiazolidinediones," Australian Prescriber, 2004, 27:70-74.

Tang et al. "Identification of glucose-regulated miRNAs from pancreatic beta cells reveals a role for miR-30d in insulin transcription." RNA, 2009, 15(2):287-293.

Trajkovski et al., "MicroRNAs 103 and 107 regulate insulin sensitivity," Nature, 2011, 474:649-654.

Wilfred et al. "Energizing miRNA research: a review of the role of miRNAs in lipid metabolism, with a prediction that miR-103/107 regulates human metabolic pathways." Mol. Genet. Metab., 2007, 91:209-217.

Xie et al. "MicroRNAs induced during adipogenesis that accelerate fat cell development are downregulated in obesity." Diabetes, 2009, 58:1050-1057.

International Search Report and Written Opinion for International Application No. PCT/IB2010/001384, mailed Sep. 7, 2010 (16 pages).

Goossens et al. "The role of adipose tissue dysfunction in the pathogenesis of obesity-related insulin resistance," physiol & Behav (2008) 94: 206-218.

Guilherme et al. "Adipocyte dysfunction linking obesity to insulin resistance and type 2 diabetes," Nat Rev Mol Cell Biol (2008) 9(5): 367-377.

* cited by examiner

SEQUENCE LISTING

```
<160> NUMBER OF SEQ ID NOS: 32

<210> SEQ ID NO 1
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 1
agcagcauug uacagggcua uga                                             23
```

```
<210> SEQ ID NO 2
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 2
agcagcauug uacagggcua uca                                            23

<210> SEQ ID NO 3
<211> LENGTH: 78
<212> TYPE: RNA
<213> ORGANISM: Artificial Sequence
<220> FEATURE:
<223> OTHER INFORMATION: Synthetic oligonucleotide

<400> SEQUENCE: 3
uacugcccuc ggcuucuuua cagugcugcc uuguugcaua uggaucaagc agcauuguac    60
agggcuauga aggcauug                                                  78

<210> SEQ ID NO 4
<211> LENGTH: 78
<212> TYPE: RNA
<213> ORGANISM: Artificial Sequence
<220> FEATURE:
<223> OTHER INFORMATION: Synthetic oligonucleotide

<400> SEQUENCE: 4
uugugcuuuc agcuucuuua cagugcugcc uuguagcauu caggucaagc agcauuguac    60
agggcuauga aagaacca                                                  78

<210> SEQ ID NO 5
<211> LENGTH: 81
<212> TYPE: RNA
<213> ORGANISM: Artificial Sequence
<220> FEATURE:
<223> OTHER INFORMATION: Synthetic oligonucleotide

<400> SEQUENCE: 5
cucucugcuu ucagcuucuu uacaguguug ccuuguggca uggaguucaa gcagcauugu    60
acagggcuau caaagcacag a                                              81

<210> SEQ ID NO 6
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 6
ucauagcccu guacaaugcu gcu                                            23

<210> SEQ ID NO 7
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 7
ugauagcccu guacaaugcu gcu                                            23
```

-continued

```
<210> SEQ ID NO 8
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 8
auagcccugu acaaugcugc u                                                  21

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
tcattggcat gtaccatgca gct                                                23

<210> SEQ ID NO 10
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 10 augcugcu                                                                  8

<210> SEQ ID NO 11
<211> LENGTH: 7
<212> TYPE: RNA
<213> ORGANISM: Artificial Sequence
<220> FEATURE:
<223> OTHER INFORMATION: Synthetic oligonucleotide

<400> SEQUENCE: 11 augcugc                                                                   7

<210> SEQ ID NO 12
<211> LENGTH: 7
<212> TYPE: RNA
<213> ORGANISM: Artificial Sequence
<220> FEATURE:
<223> OTHER INFORMATION: Synthetic oligonucleotide

<400> SEQUENCE: 12 ugcugcu                                                                   7

<210> SEQ ID NO 13
<211> LENGTH: 7
<212> TYPE: RNA
<213> ORGANISM: Artificial Sequence
<220> FEATURE:
<223> OTHER INFORMATION: Synthetic oligonucleotide

<400> SEQUENCE: 13 augcugc                                                                   7

<210> SEQ ID NO 14
<211> LENGTH: 6
<212> TYPE: RNA
<213> ORGANISM: Artificial Sequence
<220> FEATURE:
<223> OTHER INFORMATION: Synthetic oligonucleotide
```

```
<400> SEQUENCE: 14 gcugcu                                                                      6

<210> SEQ ID NO 15
<211> LENGTH: 6
<212> TYPE: RNA
<213> ORGANISM: Artificial Sequence
<220> FEATURE:
<223> OTHER INFORMATION: Synthetic oligonucleotide

<400> SEQUENCE: 15 ugcugc                                                                      6

<210> SEQ ID NO 16
<211> LENGTH: 6
<212> TYPE: RNA
<213> ORGANISM: Artificial Sequence
<220> FEATURE:
<223> OTHER INFORMATION: Synthetic oligonucleotide

<400> SEQUENCE: 16 augcug                                                                      6

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
aatacccgca tggaagcagg ctaa                                                 24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
aacatgtctc aaggagagga cggt                                                 24

<210> SEQ ID NO 19
<211> LENGTH: 23
<212> TYPE: DNA
<213> ORGANISM: Homo sapiens

<400> SEQUENCE: 19
gtgagcctat cagagttgct gca                                                  23

<210> SEQ ID NO 20
<211> LENGTH: 23
<212> TYPE: DNA
<213> ORGANISM: Homo sapiens

<400> SEQUENCE: 20
ttgcaaccgt ctgttatgct gtg                                                  23

<210> SEQ ID NO 21
<211> LENGTH: 23
<212> TYPE: DNA
<213> ORGANISM: Mus musculus

<400> SEQUENCE: 21
```
ggggtgtcaa aaaggaggct gct                                         23

<210> SEQ ID NO 22
<211> LENGTH: 23
<212> TYPE: DNA
<213> ORGANISM: Mus musculus

<400> SEQUENCE: 22
ttgcaatagt ctgcaatgct gtg                                         23

<210> SEQ ID NO 23
<211> LENGTH: 23
<212> TYPE: DNA
<213> ORGANISM: Mus musculus

<400> SEQUENCE: 23
attttacact tttttatgct gca                                         23

<210> SEQ ID NO 24
<211> LENGTH: 58
<212> TYPE: DNA
<213> ORGANISM: Mus musculus

<400> SEQUENCE: 24
tgcaaagccc ttgcaatagt ctgcaatgct gtgaagctcg acctttcccc ctgcaagg    58

<210> SEQ ID NO 25
<211> LENGTH: 58
<212> TYPE: DNA
<213> ORGANISM: Rattus norvegicus

<400> SEQUENCE: 25
ggcatagcac aagtaatagt ctgtaacgct gcgaagcctg acctctcccc ctgccagg    58

<210> SEQ ID NO 26
<211> LENGTH: 56
<212> TYPE: DNA
<213> ORGANISM: Monodelphis domestica

<400> SEQUENCE: 26
aagaaagcat gtgcaacatg taatgctgtg ataccccaac tcagccctgc tccagg      56

<210> SEQ ID NO 27
<211> LENGTH: 58
<212> TYPE: DNA
<213> ORGANISM: Canis lupus familiaris

<400> SEQUENCE: 27
agtaaagcac ttgtaaccgt ctgttatgct gtgacacaca gccctcccc ctgccagg     58

<210> SEQ ID NO 28
<211> LENGTH: 58
<212> TYPE: DNA
<213> ORGANISM: Bos taurus

<400> SEQUENCE: 28
attaaagcac ttgcaactgc ctgttatgct gtgacacatg gccctcccc ctgccacg     58

<210> SEQ ID NO 29
<211> LENGTH: 58
<212> TYPE: DNA
<213> ORGANISM: Homo sapiens

```
<400> SEQUENCE: 29
agtaaagcac ttgcaaccgt ctgttatgct gtgacacatg gccctcccc ctgccagg        58

<210> SEQ ID NO 30
<211> LENGTH: 58
<212> TYPE: DNA
<213> ORGANISM: Pan troglodytes

<400> SEQUENCE: 30
agtaaagcac ttgcaaccgt ctgttatgct gtgacacatg gccctcccc ctgccagg        58

<210> SEQ ID NO 31
<211> LENGTH: 58
<212> TYPE: DNA
<213> ORGANISM: Macaca mulatta

<400> SEQUENCE: 31
agtaaagcac ttgcaaccgt ctgttatgct gtgacacatg gccctcctg ctgccagg        58

<210> SEQ ID NO 32
<211> LENGTH: 60
<212> TYPE: DNA
<213> ORGANISM: Gallus gallus

<400> SEQUENCE: 32
ggcaaagccc ttgccacgcg ttctgatgct gtgacctaca ggagctttt gccctcatga      60
```

TARGETING MICRORNAS FOR METABOLIC DISORDERS

This application is a continuation of U.S. application Ser. No. 13/320,873, now U.S. Pat. No. 8,592,388, which is a national stage application of International Application No. PCT/IB2010/001384, filed May 19, 2010, which claims the benefit of U.S. Provisional Application No. 61/180,024, filed May 20, 2009; and U.S. Provisional application No. 61/322,878, filed Apr. 11, 2010. Each of the foregoing applications is incorporated by reference herein in its entirety for any purpose.

SEQUENCE LISTING

The present application is being filed along with a Sequence Listing in electronic format. The Sequence Listing is provided as a file entitled 2013-10-23_32433US4CON_Sequence_Listing_ST25.txt, which is 7 Kb in size. The information in the electronic format of the sequence listing is incorporated herein by reference in its entirety.

FIELD OF INVENTION

Provided herein are methods and compositions for the treatment of metabolic disorders.

DESCRIPTION OF RELATED ART

MicroRNAs (miRNAs), also known as "mature miRNA" are small (approximately 18-24 nucleotides in length), non-coding RNA molecules encoded in the genomes of plants and animals. In certain instances, highly conserved, endogenously expressed miRNAs regulate the expression of genes by binding to the 3'-untranslated regions (3'-UTR) of specific mRNAs. More than 1000 different miRNAs have been identified in plants and animals. Certain mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662).

Families of miRNAs can be characterized by nucleotide identity at positions 2-8 of the miRNA, a region known as the seed sequence. Lewis et al. describe several miRNA families, as well as miRNA superfamilies, which are characterized by related seed sequences (Lewis et al. Cell. 2005, 120(1):15-20). MicroRNAs miR-103 and miR-107 are family members, as they have identical seed regions. Thus these two microRNAs will regulate similar, if not identical, sets of target genes.

SUMMARY OF INVENTION

Provided herein are methods for treating metabolic disorders, and conditions associated with metabolic disorders, comprising administering a compound comprising an oligonucleotide targeted to a microRNA. In certain embodiments, the microRNA is miR-103. In certain embodiments, the microRNA is miR-107.

Provided herein are methods for reducing a blood glucose level of a subject comprising administering to the subject a compound comprising an oligonucleotide consisting of 12 to 30 linked nucleosides and having a nucleobase sequence complementary to miR-103, miR-107 or to a precursor of miR-103 or miR-107; and thereby reducing the blood glucose level of the subject.

Provided herein are methods for reducing blood glucose level of a subject comprising administering to the subject a compound comprising an oligonucleotide consisting of 7 to 12 linked nucleosides and having a nucleobase sequence complementary to miR-103 and miR-107, thereby reducing the blood glucose level of the subject.

In certain embodiments, the subject has an elevated blood glucose level. In certain embodiments, the methods comprise measuring the blood glucose level of the subject. In certain embodiments, the methods comprise selecting a subject having an elevated blood glucose level. In certain embodiments, the blood glucose level is a fasted blood glucose level. In certain embodiments, the blood glucose level is a post-prandial blood glucose level. In certain embodiments, the blood glucose level is a whole blood glucose level. In certain embodiments, the blood glucose level is a plasma blood glucose level.

In certain embodiments, the blood glucose level is reduced to below 200 mg/dL. In certain embodiments, the blood glucose level is reduced to below 175 mg/dL. In certain embodiments, the blood glucose level is reduced to below 150 mg/dL. In certain embodiments, the blood glucose level is reduced to below 125 mg/dL. In certain embodiments, the blood glucose level is reduced to below 120 mg/dL. In certain embodiments, the blood glucose level is reduced to below 115 mg/dL. In certain embodiments, the blood glucose level is reduced to below 110 mg/dL. In certain embodiments, the blood glucose level is reduced to below 105 mg/dL. In certain embodiments, the blood glucose level is reduced to below 100 mg/dL. In certain embodiments, the blood glucose level is reduced to below 110 mg/dL.

Provided herein are methods for preventing or delaying the onset of an elevated blood glucose level in a subject at risk for developing an elevated glucose level comprising administering to the subject a compound comprising an oligonucleotide consisting of 12 to 30 linked nucleosides and having a nucleobase sequence complementary to miR-103, miR-107, or a precursor of miR-103 or miR-107; and, thereby preventing or delaying the onset of an elevated blood glucose level in the subject.

Provided herein are methods for preventing or delaying the onset of an elevated blood glucose level in a subject at risk for developing an elevated glucose level comprising administering to the subject a compound comprising an oligonucleotide consisting of 7 to 12 linked nucleosides and having a nucleobase sequence complementary to miR-103 and miR-107, thereby preventing or delaying the onset of an elevated blood glucose level in the subject.

Provided herein are methods for reducing gluconeogenesis in a subject comprising administering to the subject a compound comprising an oligonucleotide consisting of 12 to 30 linked nucleosides and having a nucleobase sequence complementary to miR-103, miR-107 or a precursor of miR-103 or miR-107; and thereby reducing gluconeogenesis in the subject. In certain embodiments, the subject has elevated gluconeogenesis.

Provided herein are methods for reducing gluconeogenesis in a subject comprising administering to the subject a compound comprising administering to the subject a compound comprising an oligonucleotide consisting of 7 to 12 linked nucleosides and having a nucleobase sequence complementary to miR-103 and miR-107; and thereby reducing gluconeogenesis in the subject.

Provided herein are methods for improving insulin sensitivity in a subject comprising administering to the subject a compound comprising an oligonucleotide consisting of 12 to 30 linked nucleosides and having a nucleobase sequence complementary to miR-103, miR-107 or a precursor of miR-103 or miR-107; and thereby improving insulin sensitivity in the subject. In certain embodiments, the subject has insulin resistance. In certain embodiments, the methods comprise selecting a subject having insulin resistance.

Provided herein are methods for improving insulin sensitivity in a subject comprising administering to the subject a compound comprising administering to the subject a compound comprising an oligonucleotide consisting of 7 to 12 linked nucleosides and having a nucleobase sequence complementary to miR-103 and miR-107; and thereby improving insulin sensitivity in the subject.

Provided herein are methods for preventing or delaying the onset of insulin resistance in a subject at risk for developing insulin resistance comprising administering to the subject a compound comprising an oligonucleotide consisting of 12 to 30 linked nucleosides and having a nucleobase sequence complementary to miR-103, miR-107 or a precursor of miR-103 or miR-107; and thereby preventing or delaying the onset of insulin resistance in the subject. In certain embodiments, the methods comprise selecting a subject at risk for developing insulin resistance.

Provided herein are methods for preventing or delaying the onset of insulin resistance in a subject at risk for developing insulin resistance comprising administering to the subject a compound comprising administering to the subject a compound comprising an oligonucleotide consisting of 7 to 12 linked nucleosides and having a nucleobase sequence complementary to miR-103 and miR-107; and thereby preventing or delaying the onset of insulin resistance in the subject.

Provided herein are methods for improving glucose tolerance in a subject comprising administering to the subject a compound comprising an oligonucleotide consisting of 12 to 30 linked nucleosides and having a nucleobase sequence complementary to miR-103, miR-107 or a precursor of miR-103 or miR-107; and thereby improving glucose tolerance. In certain embodiments, the subject has impaired glucose tolerance. In certain embodiments, the methods comprise selecting a subject having impaired glucose tolerance.

Provided herein are methods for improving glucose tolerance in a subject comprising administering to the subject a compound comprising administering to the subject a compound comprising an oligonucleotide consisting of 7 to 12 linked nucleosides and having a nucleobase sequence complementary to miR-103 and miR-107; and thereby improving glucose tolerance.

Provided herein are methods for decreasing the plasma cholesterol level in a subject comprising administering to the subject a compound comprising an oligonucleotide consisting of 12 to 30 linked nucleosides and having a nucleobase sequence complementary to miR-103, miR-107 or a precursor of miR-103 or miR-107; and thereby decreasing plasma cholesterol in the subject. In certain embodiments, the subject has an elevated plasma cholesterol level. In certain embodiments, the methods comprise selecting a subject having an elevated plasma cholesterol level. In certain embodiments, the plasma cholesterol is LDL-cholesterol. In certain embodiments, the plasma cholesterol is VLDL-cholesterol.

In any of the methods provided herein, the subject may have a metabolic disorder.

Provided herein are methods for treating at least one metabolic disorder in a subject, comprising administering to the subject having a metabolic disorder a compound comprising an oligonucleotide consisting of 12 to 30 linked nucleosides and having a nucleobase sequence complementary to miR-103, miR-107 or a precursor miR-103 or miR-107; and thereby treating the metabolic disorder.

Provided herein are methods for treating at least one metabolic disorder in a subject, comprising administering to the subject having a metabolic disorder a compound comprising administering to the subject a compound comprising an oligonucleotide consisting of 7 to 12 linked nucleosides and having a nucleobase sequence complementary to miR-103 and miR-107; and thereby treating the metabolic disorder.

Provided herein are methods for preventing or delaying the onset of at least one metabolic disorder in a subject at risk for developing a metabolic disorder, comprising administering to the subject a compound comprising modified oligonucleotide consisting of 12 to 30 linked nucleosides and having a nucleobase sequence complementary to miR-103, miR-107 or a precursor miR-103 or miR-107; and thereby preventing or delaying the onset of a metabolic disorder in the subject.

Provided herein are methods for preventing or delaying the onset of at least one metabolic disorder in a subject at risk for developing a metabolic disorder, comprising administering to the subject a compound comprising administering to the subject a compound comprising an oligonucleotide consisting of 7 to 12 linked nucleosides and having a nucleobase sequence complementary to miR-103 and miR-107; and thereby preventing or delaying the onset of a metabolic disorder in the subject.

In certain embodiments, the at least one metabolic disorder is selected from among pre-diabetes, diabetes, metabolic syndrome, obesity, diabetic dyslipidemia, hyperlipdemia, hypertension, hypertriglyceridemia, hyperfattyacidemia, hypercholesterolemia, and hyperinsulinemia.

In certain embodiments, the administering comprises parenteral administration. In certain embodiments, the parenteral administration comprises intravenous administration or subcutaneous administration. In certain embodiments, the administering comprises oral administration.

In certain embodiments, the administering comprises administering at least one additional therapy. In certain embodiments, the at least one additional therapy is a glucose-lowering agent. In certain embodiments, the glucose-lowering agent is selected from among a PPAR agonist (gamma, dual, or pan), a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, a meglitinide, a thiazolidinedione, and sulfonylurea. In certain embodiments, the at least one additional therapy is a lipid-lowering agent. In certain embodiments, the at least one additional therapy is administered at the same time as the compound. In certain embodiments, the at least one additional therapy is administered less frequently than the compound. In certain embodiments, the at least one additional therapy is administered more frequently than the compound. In certain embodiments, the at least one additional therapy is administered prior to administration of the compound. In certain embodiments, the at least one additional therapy is administered after administration of the compound. In certain embodiments, the at least one additional therapy and the compound are co-administered.

In certain embodiments, the compound is administered in the form of a pharmaceutical composition.

Provided herein are methods for improving insulin resistance in a cell or tissue comprising contacting the cell or tissue with a compound comprising an oligonucleotide consisting of 12 to 30 linked nucleosides and having a nucleobase sequence complementary to the nucleobase sequence of SEQ ID NO: 1, 2, 3, 4, or 5. In certain embodiments, the cell or tissue is a liver, fat, or skeletal muscle cell or tissue. In certain embodiments, the cell or tissue is a fat cell or tissue. In certain embodiments, the cell or tissue is contacted in vivo.

Provided herein are methods for increasing adipocyte differentiation in a subject comprising administering to the subject a compound comprising modified oligonucleotide consisting of 12 to 30 linked nucleosides and having a nucleobase sequence complementary to miR-103, miR-107 or a precursor miR-103 or miR-107, thereby increasing adipocyte differentiation in the subject. In certain embodiments, the subject has excess body fat. In certain embodiments, the administration reduces the body weight of the subject. In certain embodiments, the administering reduces body fat in the subject.

Provided herein are methods for increasing adipocyte differentiation in a subject comprising administering to the subject a compound comprising an oligonucleotide consisting of 7 to 12 linked nucleosides and having a nucleobase sequence complementary to miR-103 and miR-107, thereby increasing adipocyte differentiation in the subject.

Provided herein are methods for increasing insulin sensitivity in a cell comprising contacting the cell with a compound comprising an oligonucleotide consisting of 12 to 30 linked nucleosides and having a nucleobase sequence complementary to the nucleobase sequence of SEQ ID NO: 1, 2, 3, 4, or 5. In certain embodiments, the cell has a decreased sensitivity to insulin. In certain embodiments, the cell is an adipocyte cell.

Provided herein are methods for inducing adipocyte differentiation comprising contacting an undifferentiated adipocyte with a compound comprising an oligonucleotide consisting of 12 to 30 linked nucleosides and having a nucleobase sequence complementary to the nucleobase sequence of SEQ ID NO: 1, 2, 3, 4, or 5.

In certain embodiments, the compound consists of the oligonucleotide.

In certain embodiments, the nucleobase sequence of the oligonucleotide is at least 85% complementary to the nucleobase sequence of SEQ ID NO: 1, 2, 3, 4, or 5. In certain embodiments, the nucleobase sequence of the oligonucleotide is at least 90% complementary to the nucleobase sequence of SEQ ID NO: 1, 2, 3, 4, or 5. In certain embodiments, the nucleobase sequence of the oligonucleotide is at least 95% complementary to the nucleobase sequence of SEQ ID NO: 1, 2, 3, 4, or 5. In certain embodiments, the nucleobase sequence of the oligonucleotide is fully complmentary to the nucleobase sequence of SEQ ID NO: 1, 2, 3, 4, or 5. In certain embodiments, the nucleobase sequence of the oligonucleotide has no more than two mismatches to a nucleobase sequence selected from SEQ ID NO: 1, 2, 3, 4, or 5. In certain embodiments, the nucleobase sequence of the oligonucleotide has no more than one mismatch to a nucleobase sequence selected from SEQ ID NO: 1, 2, 3, 4, or 5. In certain embodiments, the nucleobase sequence of the oligonucleotide has one mismatch to a nucleobase sequence selected from SEQ ID NO: 1, 2, 3, 4, or 5. In certain embodiments, the nucleobase sequence of the oligonucleotide has no mismatches to a nucleobase sequence selected from SEQ ID NO: 1, 2, 3, 4, or 5.

In certain embodiments, the oligonucleotide is a modified oligonucleotide. In certain embodiments, the oligonucleotide comprises at least one modified internucleoside linkage. In certain embodiments, the oligonucleotide comprises at least two modified internucleoside linkages. In certain embodiments, the oligonucleotide comprises at least three modified internucleoside linkages. In certain embodiments, the first and last internucleoside linkages of the oligonucleotide are modified internucleoside linkages. In certain embodiments, each internucleoside linkage of the oligonucleotide is a modified internucleoside linkage. In certain embodiments, at least one modified internucleside linkage is a phosphorothioate internucleoside linkage. In certain embodiments, the oligonucleotide comprises at least one nucleoside comprising a modified sugar. In certain embodiments, the oligonucleotide comprises at least two nucleosides comprising a modified sugar. In certain embodiments, the oligonucleotide comprises at least three nucleosides comprising a modified sugar. In certain embodiments, each nucleoside the oligonucleotide comprises a modified sugar. In certain embodiments, each nucleoside the oligonucleotide comprises a 2'-O-methoxyethyl sugar. In certain embodiments, the oligonucleotide comprises a plurality of nucleosides comprising a 2'-O-methoxyethyl sugar and a plurality of nucleosides comprising a 2'-fluoro sugar modification. In certain embodiments, each modified sugar is independently selected from a 2'-O-methoxyethyl sugar, a 2'-fluoro sugar, 2'-O-methyl sugar, and a bicyclic sugar moiety. In certain embodiments, the bicyclic sugar moiety is LNA. In certain embodiments, the compound comprises a conjugate linked to the oligonucleotide. In certain embodiments, the conjugate is cholesterol.

In certain embodiments, the modified oligonucleotide has the following modifications: each nucleoside is a 2'-O-methyl nucleoside, each of the first two 5' internucleoside linkages are phosphorothioate, each of the four 3' terminal internucleoside linkages are phosphorothioate, each of the remaining internucleoside linkages is phosphodiester, and the 3' terminal nucleoside is linked to cholesterol through a hydroxyprolinol linkage.

In certain embodiments, the oligonucleotide consists of 7 linked nucleosides. In certain embodiments, the oligonucleotide consists of 8 linked nucleosides. In certain embodiments, the oligonucleotide consists of 9 linked nucleosides. In certain embodiments, the oligonucleotide consists of 10 linked nucleosides. In certain embodiments, the oligonucleotide consists of 11 linked nucleosides. In certain embodiments, the oligonucleotide consists of 12 linked nucleosides. In certain embodiments, the oligonucleotide consists of 13 linked nucleosides. In certain embodiments, the oligonucleotide consists of 14 linked nucleosides. In certain embodiments, the oligonucleotide consists of 15 linked nucleosides. In certain embodiments, the oligonucleotide consists of 16 linked nucleosides. In certain embodiments, the oligonucleotide consists of 17 linked nucleosides. In certain embodiments, the oligonucleotide consists of 18 linked nucleosides. In certain embodiments, the oligonucleotide consists of 19 linked nucleosides. In certain embodiments, the oligonucleotide consists of 20 linked nucleosides. In certain embodiments, the oligonucleotide consists of 21 linked nucleosides. In certain embodiments, the oligonucleotide consists of 22 linked nucleosides. In certain embodiments, the oligonucleotide consists of 23 linked nucleosides. In certain embodiments, the oligonucleotide consists of 24 linked nucleosides.

In certain embodiments, the nucleobase sequence of the oligonucleotide comprises the nucleobase sequence of SEQ ID NO: 6, 7, or 8. In certain embodiments, the nucleobase sequence of the oligonucleotide consists of the nucleobase sequence of SEQ ID NO: 6, 7, or 8.

In certain embodiments, the oligonucleotide comprises the nucleobase sequence of any of SEQ ID NOs 10, 11, 12, 13, 14, 15, and 16. In certain embodiments, oligonucleotide comprises the nucleobase sequence of SEQ ID NO: 10. In certain embodiments, the oligonucleotide comprises the nucleobase sequence of SEQ ID NO: 11.

BRIEF DESCRIPTION OF DRAWINGS

Unless otherwise specified, wildtype male C57Bl/6 mice (≈20 g) were injected with either PBS, anti-miR-107 (1×15 mg/kg), anti-miR103 (2×15 mg/kg), anti-mm-107 (2×15 µg/kg), or anti-miR-124 (2×15 µg/kg), while male ob/ob (45 g) with either PBS, anti-miR-107 (1×15 mg/kg), anti-miR-103 (2×15 mg/kg), or anti-miR-124 (2×15 mg/kg). Throughout the Figures, the labeling of anti-miR treatment is as described in the following table.

TABLE 1

Description of Modified Oligonucleotides

| Figure Label | Description of Figures & Examples | Sequence and Chemistry |
|---|---|---|
| Ant.103 or Ant-103 | anti-miR-103 | UCAUAGCCCUGUACAAUGCUGCU (SEQ ID NO: 6)<br>2'-O-methyl modification at each sugar<br>Phosphorothioate linkages at each of the first 4 and last 2 internucleoside linkages; remaining linkages are phosphodiester<br>Cholesterol at the 3' end linked through hydroxyprolinol |
| Ant.107 or Ant-107 | anti-miR-107 | UGAUAGCCCUGUACAAUGCUGCU (SEQ ID NO: 7)<br>2'-O-methyl modification at each sugar<br>Phosphorothioate linkages at each of the first 4 and last 2 internucleoside linkages; remaining linkages are phosphodiester<br>Cholesterol at the 3' end linked through hydroxyprolinol |
| Ant.scr or Ant-scr or Ant.MM107 or Anti-MM107 or Ant.MM103 or Ant-MM103 | anti-mm-107 | TCATTGGCATGTACCATGCAGCT (SEQ ID NO: 9)<br>2'-O-methyl modification at each sugar<br>Phosphorothioate linkages at each of the first 4 and last 2 internucleoside linkages; remaining linkages are phosphodiester<br>Cholesterol at the 3' end linked through hydroxyprolinol |
| Ant.124 or Ant-124 | anti-miR-124 | Full complement of miR-124<br>TGGCATTCACCGCGTGCCTTAA (SEQ ID NO: 19)<br>2'-O-methyl modification at each sugar<br>Phosphorothioate linkages at each of the first 4 and last 2 internucleoside linkages; remaining linkages are phosphodiester<br>Cholesterol at the 3' end linked through hydroxyprolinol |

In certain embodiments, the oligonucleotide consists of the nucleobase sequence of any of SEQ ID NOs 10, 11, 12, 13, 14, 15, and 16. In certain embodiments, oligonucleotide consists of the nucleobase sequence of SEQ ID NO: 10. In certain embodiments, the oligonucleotide consists of the nucleobase sequence of SEQ ID NO: 11. In certain such embodiments, each nucleoside comprises a sugar modification.

Provided herein are methods for identifying a subject in need of treatment comprising comparing the amount of a microRNA in a sample obtained from the subject with the amount of negative control, wherein the microRNA is miR-103 or miR-107 and wherein a greater amount of microRNA in the sample obtained from the subject indicates that the subject is in need of treatment with a compound comprising a modified oligonucleotide complementary to miR-103/107. In certain embodiments, the sample is a liver sample. In certain embodiments, the sample is an adipose sample. In certain embodiments, the subject is at risk for developing a metabolic disorder. In certain embodiments, the subject is suspected of having a metabolic disorder. In certain embodiments, the subject is treated with a compound comprising a modified oligonucleotide having nucleobase complementarity to miR-103 and/or miR-107, or a precursor thereof.

These and other embodiments of the present invention will become apparent in conjunction with the figures, description and claims that follow.

Figure 1:
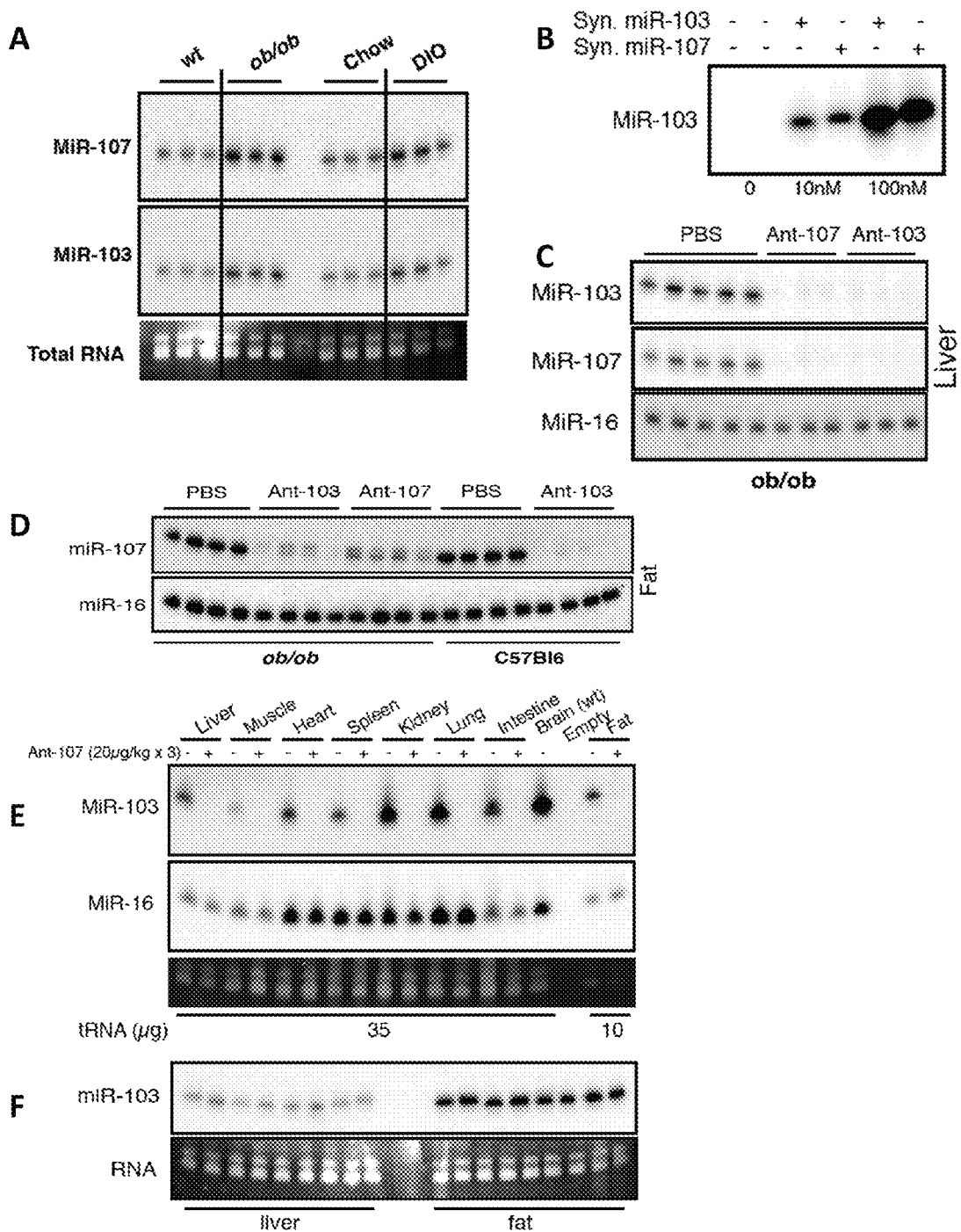

FIG. 1. miR-103 and miR-107 are up-regulated in models of diabetes and obesity. (A) Northern blotting for miR-103 and miR-107 on 25 µg total RNA from livers of wildtype (wt), ob/ob, normal chow-fed (Chow) or DIO mice as indicated (n=3). Ethidium bromide staining of total RNA is shown as control. (B) Northern blotting for miR-103 on 0, 10, or 100 nM synthetic miR-103 or miR-107. (C) Northern blotting for miR-103, miR-107, or miR-16 on 35 µg total RNA from livers of ob/ob mice injected either with anti-miR-103 and anti-miR-107, or PBS as control. (D) Northern blotting for miR-107 or miR-16 on 35 µg total RNA from fat of ob/ob or C57bl/6 mice injected with either anti-miR-103, anti-miR-107, or PBS as control. (E) Northern blotting for miR-103, miR-16 or U6 on 35, 10, or 5 ug of total RNA from different organs of C57Bl/6, with or without anti-miR-103 treatment. (F) Northern blotting for miR-103 on 35 ug of total RNA from livers and fat of C57Bl/6 mice.

Figure 2:
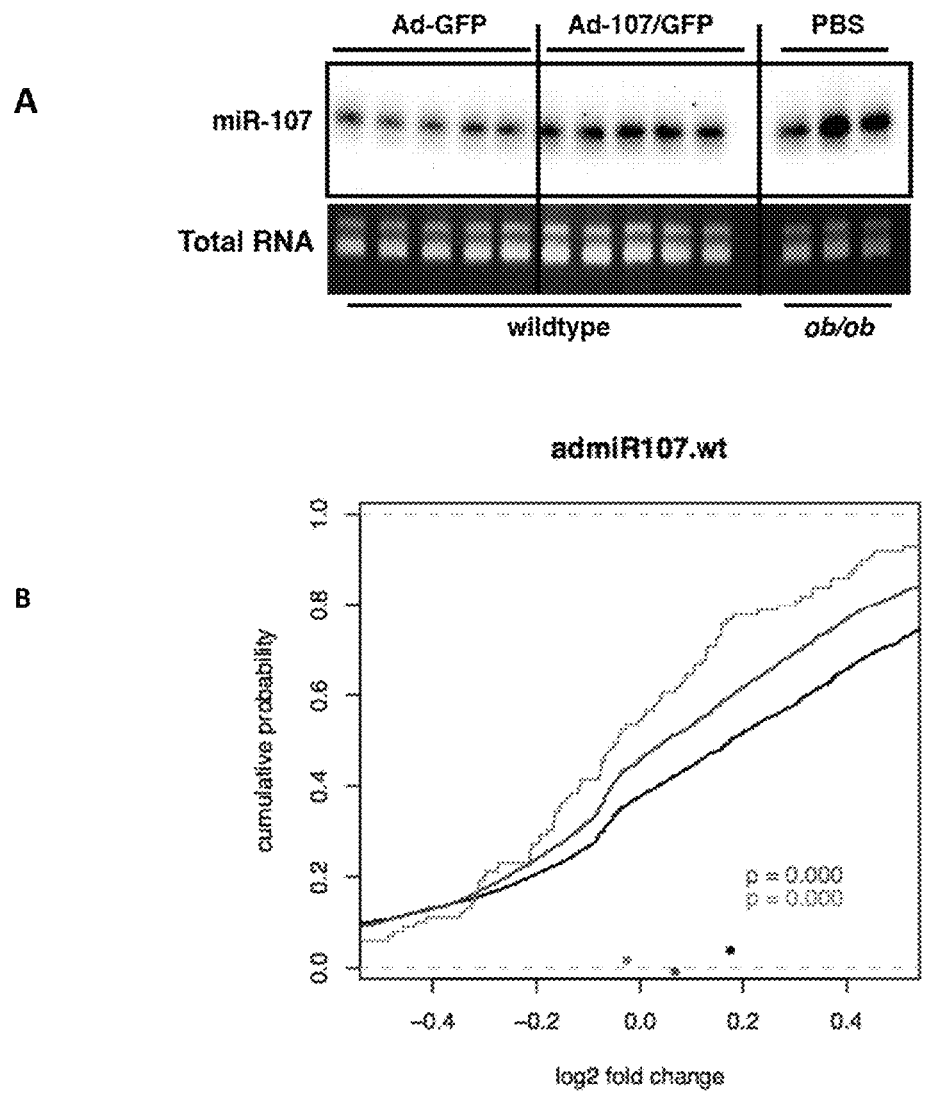

FIG. 2. Adenoviral-mediated overexpression of miR-107 increases miR-107 expression and down-regulates miR-103/107 targets. (A) Northern blot analysis of miR-107 from liver in adenovirus-injected C57Bl/6, or PBS injected ob/ob mice. All experiments shown are from n=5. (B) mRNAs having a seed match to miR-107 in the 3' UTR were significantly downregulated compared to mRNAs without a seed match to miR-107 in the 3' UTR; the down-regulation is more pronounces for the subset of mRNAs harboring seed matches inferred to be under evolutionary selective pressure.

Figure 3:
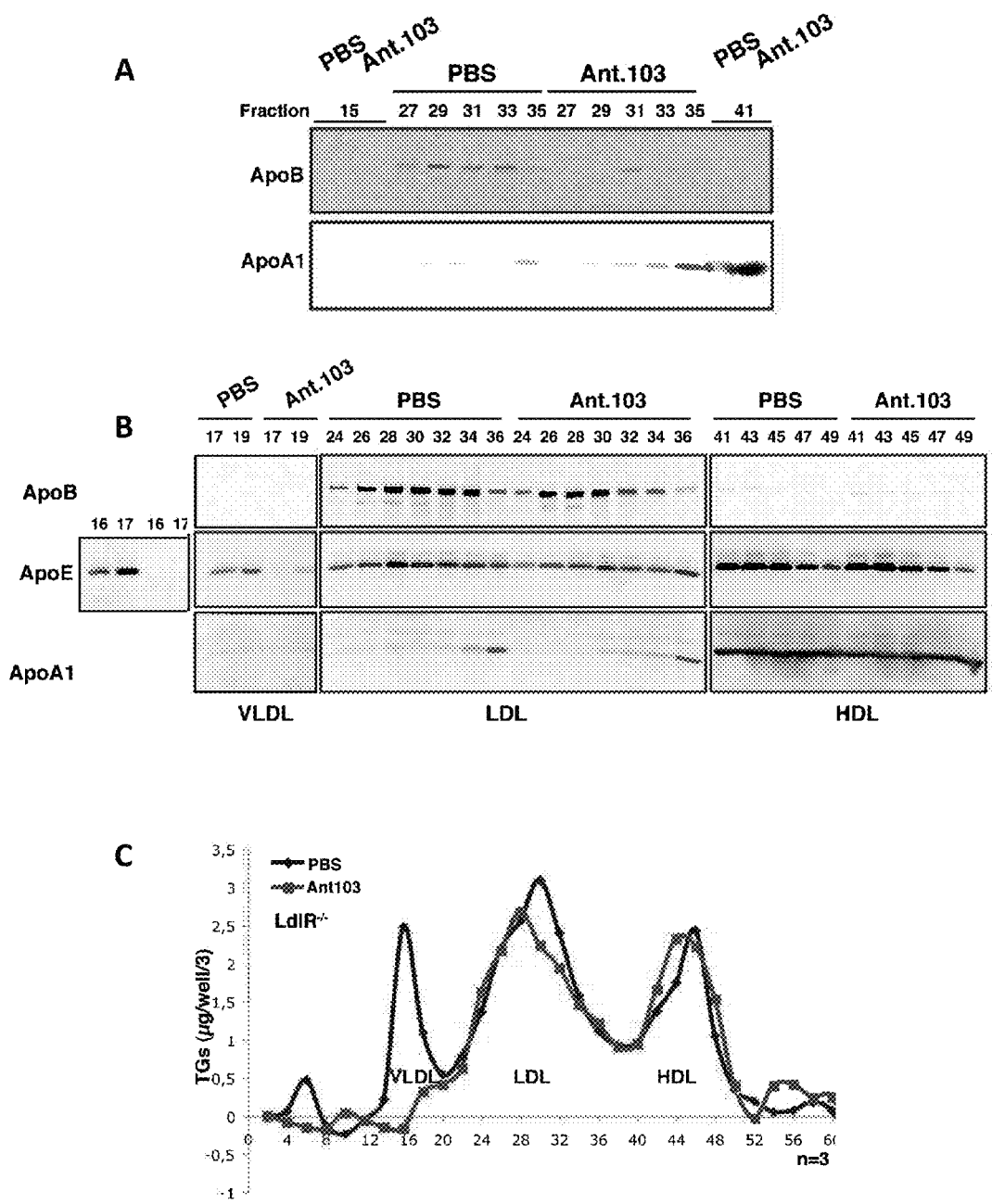

FIG. 3. Anti-miR inhibition of miR-103/107 decreases cholesterol. (A) Western blotting of the fractions as indicated, immunoblotted with anti-apoB, or anti-apoA1 anibodies as markers of LDL, or HDL respectively. (B) Western blotting of the fractions as indicated, immunoblotted with anti-apoE, anti-apoB, or anti-apoA1 antibodies as markers of VLDL, LDL, or HDL respectively. (C) Major lipoprotein fractions separated by FPLC gel filtration from 150 ul of plasma of 8 week old female LDLR-/- mice injected with either PBS or anti-miR-103, assayed for triglycerides.

Figure 4:
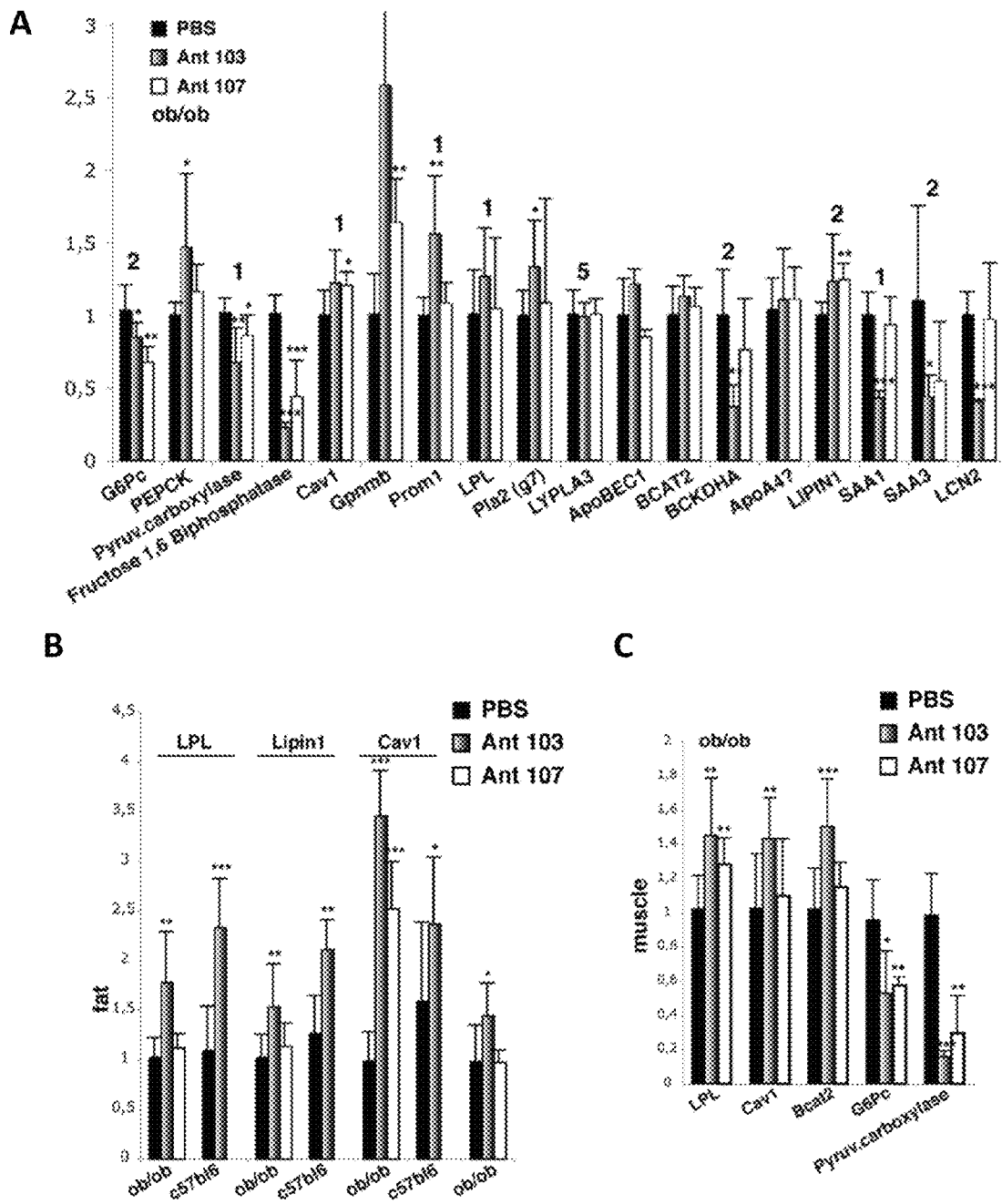

FIG. 4. Anti-miR inhibition of miR-103/107 decreases gene targets. (A) Real-time PCR of target genes using liver RNA from ob/ob mice upon silencing of miR-103/107. (B) Real-time PCR of target genes using fat RNA from ob/ob following anti-miR silencing of miR-103/107. (C) Real-time PCR of target genes using muscle RNA from ob/ob mice following anti-miR silencing of miR-103/107.

Figure 5:
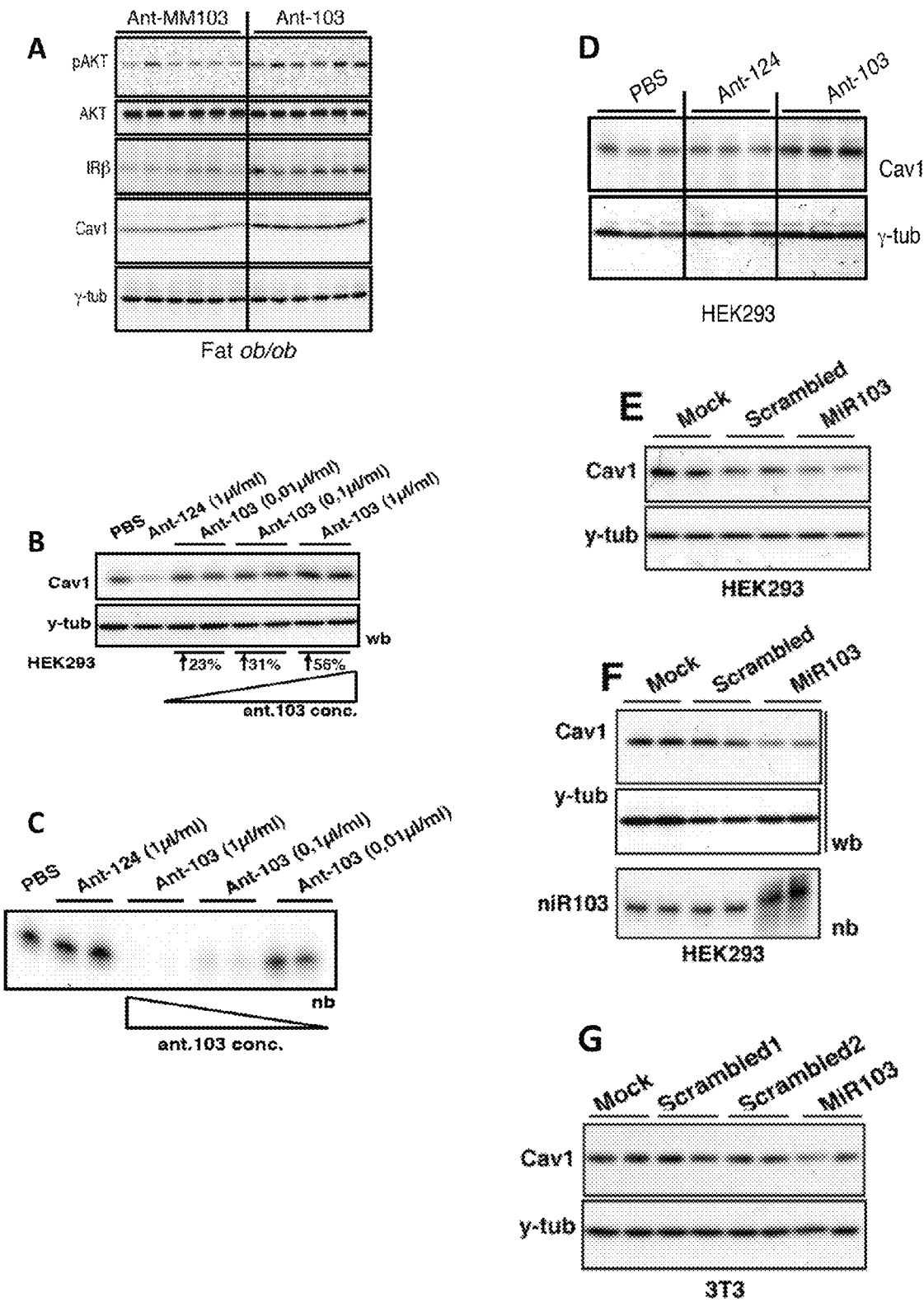

FIG. 5. Modulation of miR-103 or miR-107 regulates target proteins. (A) Western blot of total extracts from fat of ob/ob mice injected with either PBS or anti-miR-103 as in FIGS. 1A and B. Membranes were blotted with antibodies against Caveolin 1 (Santa Cruz), Insulin receptor b (IRb), pAKT, AKT and y-tubulin. (B, C) Western (B), and northern blotting (C) of 35 μg protein extracts, or 25 μg total RNA from HEK293 cells transfected with PBS, anti-miR-124, or anti-miR-103 in concentrations as indicated. Cells were harvested 3 days after the anti-miR treatment. (D) Western blotting of total cell extracts from HEK293 cells plated in 6-well format and incubated with anti-miR-103. Cells were harvested 3 days after anti-miR treatment. (E and F) Western blot of total cell extracts from HEK293 cells plated in 6-well format harvested 2 days after transfection with mock, scrambled or miR103 siRNA in concentration of 250 pmol/well of a 6 well plate. (G) Western blot of total cell extracts from 3T3 cells plated in 6 well format and harvested 2 days after transfection with mock, scrambled 1, scrambled 2, or miR-103 siRNA in concentration of 250 pmol/well of a 6-well plate.

Figure 6:
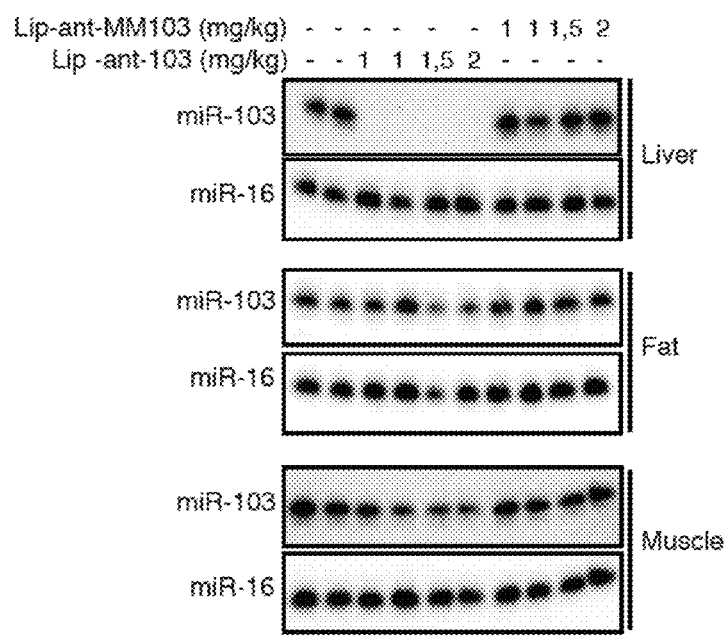

FIG. 6. Liposomal delivery of anti-miR-103. Northern blotting for miR-103 or miR-16 on 30 μg of total RNA from liver, fat, or muscle from ob/ob mice injected with different amounts of Lip-anti-miR-103, Lip-anti-miR-107, or PBS as control.

Figure 7:
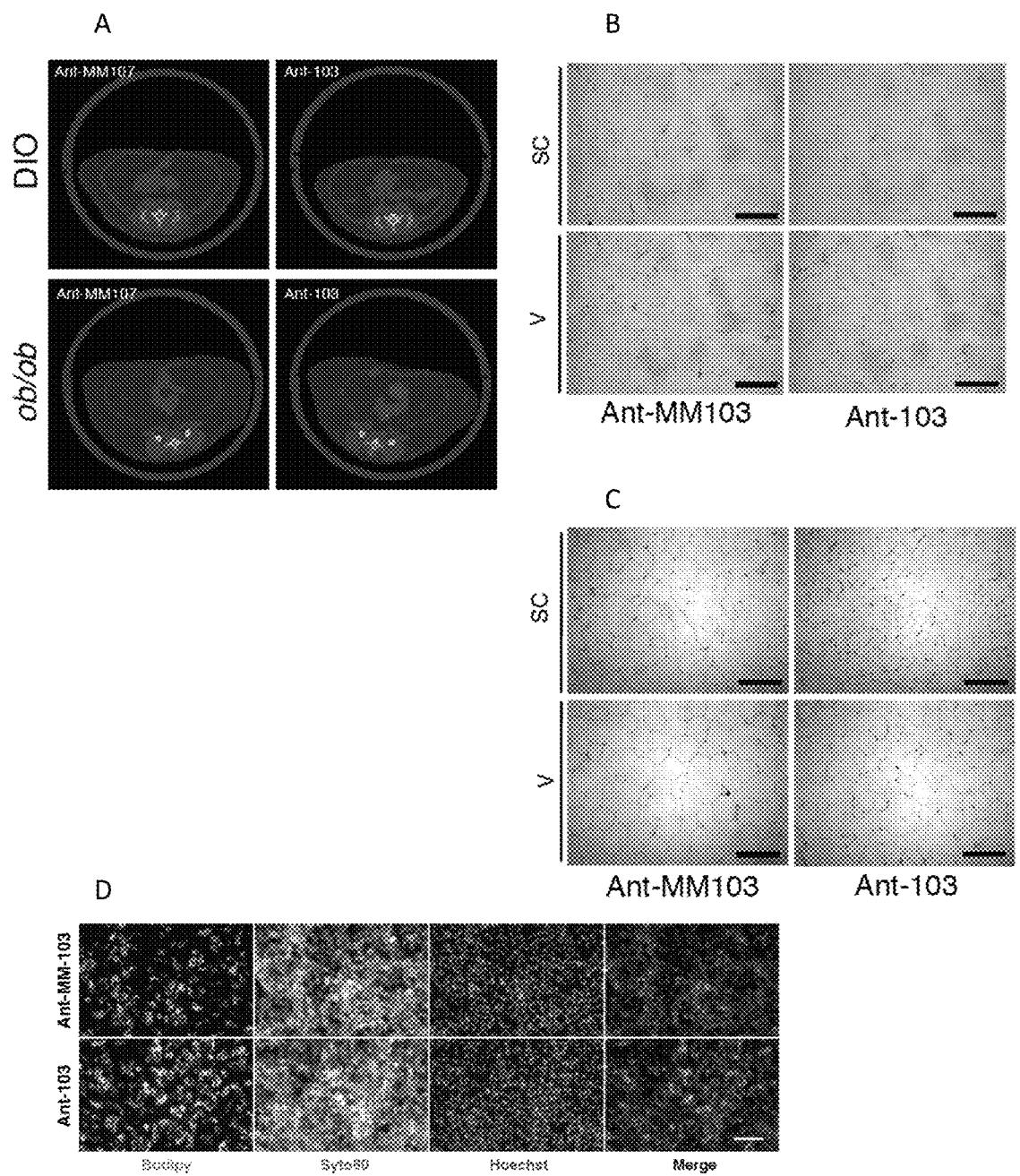

FIG. 7. Effects of miR-103/107 inhibition in adipose tissue. (A) Computer tomography (CT) in anti-miR-107, or anti-miR-103 injected DIO (top), or ob/ob mice (bottom). (B, C) Hematoxylin (HE) staining of paraffin sections from SC, or V fat of anti-miR-107, or anti-miR-103 ob/ob (B), and DIO (C) injected mice. (D) BODIPY lipid droplets staining, Hoechst nuclear detection and Syto60 cytosolic staining in SVF cells after 8 days of differentiation in presence of anti-miR-103, or anti-miR-107.

Figure 8:
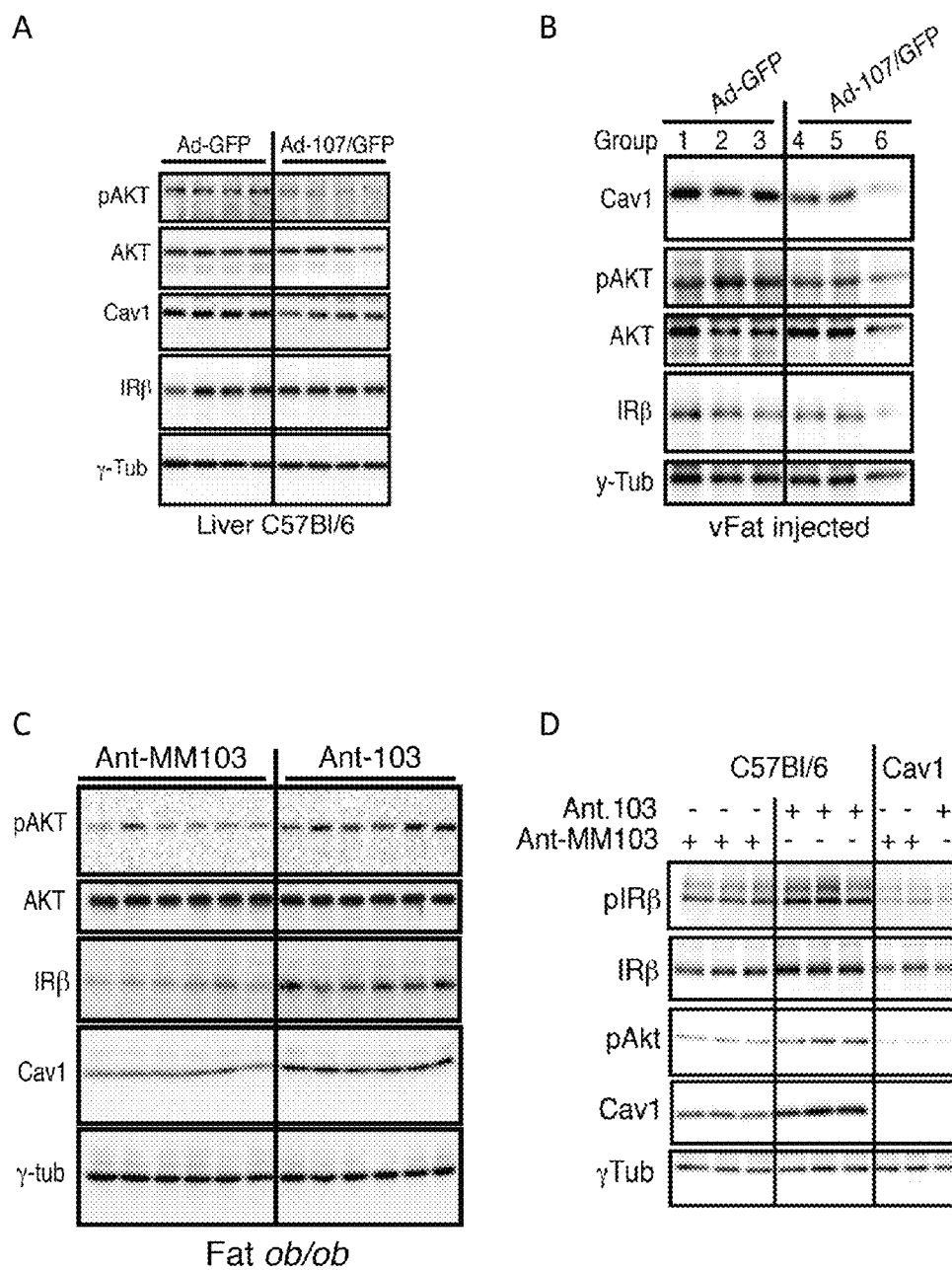

FIG. 8. Regulation of gene expression and insulin signaling by miR-103. (A) Western blotting of 50 μg total protein extracts from livers of C57Bl/6 mice injected with Ad-GFP, or ad-107/GFP. (B) Western blotting on 20 μg protein extracts from V fat of C57Bl/6 mice surgically V fat injected with ad-GFP, or ad-107/GFP. Each lane represents pool of protein extracts from two mice. (C) Western blotting on 20 μg protein extracts from fat of anti-miR-107, or anti-miR-103 injected ob/ob mice. (D) Western blotting on 20 μg protein extracts from fat of C57Bl/6, or Cav1 knockout (Cav1 KO) mice kept on high fat diet for 5 weeks, 8 days after injection with anti-miR-107, or anti-miR-103. Mice were fasted for 12 h and stimulated for 8 minutes with insulin at a dose of 1.2 U/kg.

Figure 9:
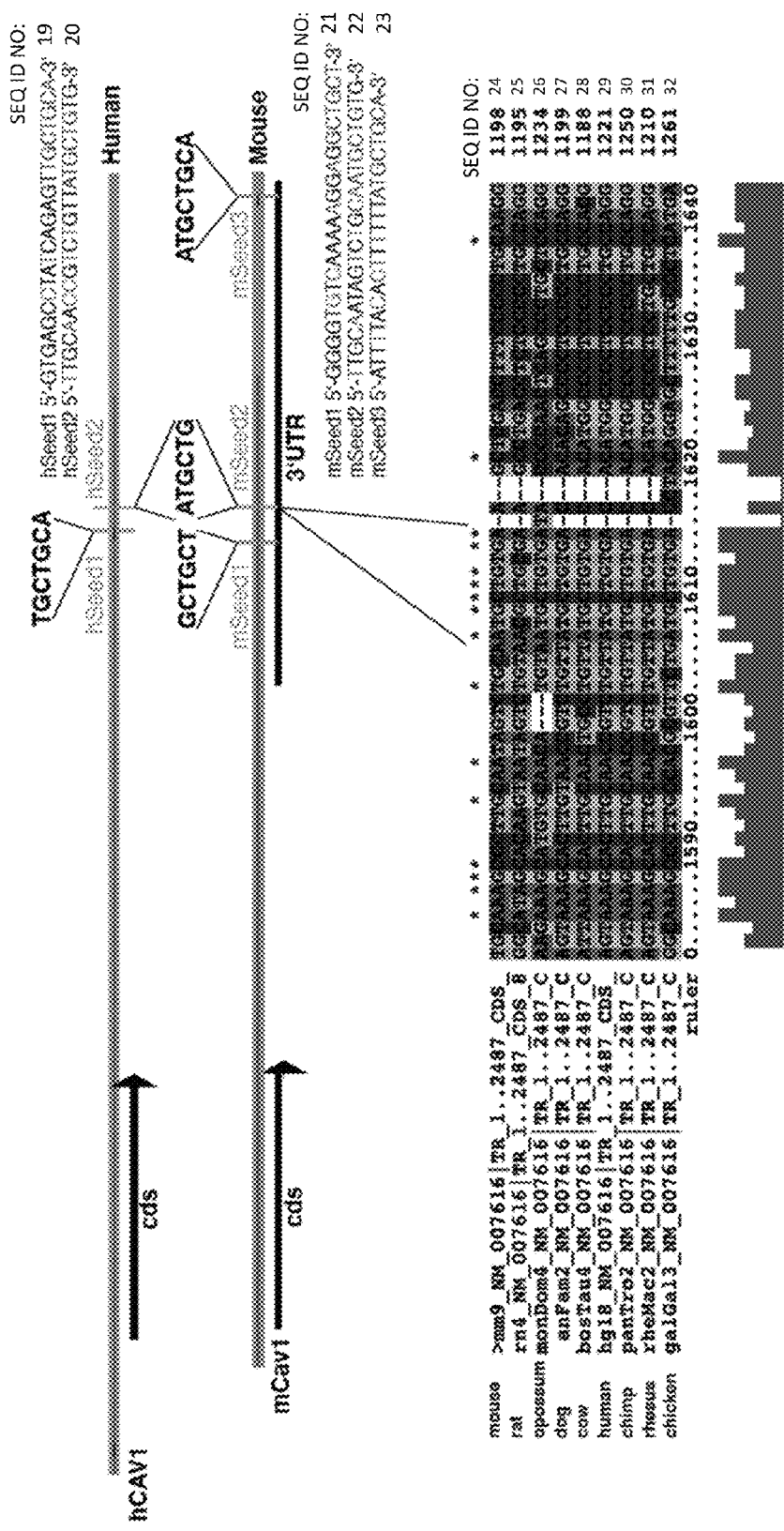

FIG. 9. miR-103 binding sites. Graphical representation of Cav1 coding sequence (CDS) and its 3'UTR with the seeds motifs in human and mouse. The seed sequences are marked in brown, and the matching residues between Cav1 3'UTR and the miR-103 proximal to the seed sequence in red. Multiple alignment of Cav1 seed 2 3'UTR region.

DETAILED DESCRIPTION

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Definitions

"Blood glucose level" means the concentration of glucose in the blood of a subject. In certain embodiments, blood glucose levels are expressed as milligrams of glucose per deciliter of blood. In certain embodiments, blood glucose levels are expressed as mmol of glucose per liter of blood.

"Elevated blood glucose level" means a blood glucose level that is higher than normal.

"Fasted blood glucose level" means a blood glucose level after a subject has fasted for a certain length of time. For example, a subject may fast for at least 8 hours prior to measurement of a fasted blood glucose level.

"Post-prandial blood glucose level" means a blood glucose level after a subject has eaten a meal. In certain embodiments, a post-prandial blood glucose level is measured two hours after a subject has eaten a meal.

"Whole blood gluocose level" means the concentration of glucose in whole blood which has not been subjected to separation.

"Plasma blood glucose level" means the concentration of glucose in plasma following separation of whole blood into plasma and red blood cell fractions.

"Insulin sensitivity" means the ability of cells to take up glucose in response to insulin action.

"Insulin resistance" means a condition in which normal amounts of insulin are inadequate to produce a normal insulin response from fat, muscle and liver cells. Insulin resistance in fat cells results in hydrolysis of stored triglycerides, which elevates free fatty acids in the blood. Insulin resistance in muscle reduces the uptake of glucose from the blood by muscle cells. Insulin resistance in liver reduces glucose storage and a failure to suppress glucose production. Elevated free fatty acids, reduced glucose uptake, and elevated glucose production all contribute to elevated blood glucose levels. High plasma levels of insulin and glucose due to insulin resistance often leads to metabolic syndrome and type 2 diabetes.

"Improving insulin resistance" means increasing the ability of cells to produce a normal insulin response. In certain embodiments, insulin resistance is improved in muscle cells, leading to an increased uptake of glucose in muscle cells. In certain embodiments, insulin resistance is improved in liver cells, leading to increased glucose storage in liver cells. In certain embodiments, insulin resistance is improved in fat cells, leading to reduced hydrolysis of triglycerides, and consequently reduced free fatty acid in the blood.

"Metabolic disorder" means a condition characterized by an alteration or disturbance in one or more metabolic processes in the body. Metabolic disorders include, but are not limited to, hyperglycemia, prediabetes, diabetes, type 1 diabetes, type 2 diabetes, obesity, diabetic dyslipidemia, metabolic syndrome, and hyperinsulinemia. "Diabetes" or "diabetes mellitus" means a disease in which the body does not produce or properly use insulin, resulting in abnormally high blood glucose levels. In certain embodiments, diabetes is type 1 diabetes. In certain embodiments, diabetes is type 2 diabetes.

"Prediabetes" means a condition in which a subject's blood glucose levels are higher than in a subject with normal blood glucose levels but lower but not high enough for a diagnosis of diabetes.

"Type 1 diabetes" means diabetes characterized by loss of the insulin-producing beta cells of the islets of Langerhans in the pancreas leading to a deficiency of insulin (also known as insulin-dependent diabetes mellitus or IDDM). Type I diabetes can affect children or adults, but typically appears between the ages of 10 and 16.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Diabetic dyslipidemia" or "Type 2 diabetes with dyslipidemia" means a condition characterized by Type 2 diabetes, reduced HDL-C, elevated serum triglycerides, and elevated small, dense LDL particles.

"Metabolic syndrome" means a condition characterized by a clustering of lipid and nonlipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Steatosis" means a condition characterized by the excessive accumulation of triglycerides in hepatocytes.

"Steatohepatitis" means steatosis with inflammation.

"Non-alcoholic fatty liver disease (NAFLD)" means a condition characterized accumulation of fat in the liver in subjects who consume little to no alcohol. In certain embodiments, NAFLD is related to insulin resistance and the metabolic syndrome.

"Nonalcoholic steatohepatitis (NASH)" means a condition characterized by accumulation of fat in the liver, combined with inflammation and scarring in the liver. In certain embodiments NASH results from a worsening progression of NAFLD.

"Alcoholic steatohepatitis (ASH)" means an alcohol-induced condition characterized by accumulation of fat in the liver, combined with inflammation and scarring in the liver.

"Glucose Tolerance Test" or "GTT" means a test performed to determine how quickly glucose is cleared from the blood. Typically, the test involves administration of glucose, followed by measurement of glucose levels in blood at intervals over a period of time. "IPGTT" means a GTT performed following intraperitoneal injection of glucose. "OGTT" means a GTT performed following oral administration of glucose. In certain embodiments, a GTT is used to test for pre-diabetes. In certain embodiments, a GTT is used to identify a subject with diabetes. In certain embodiments, a GTT is used to identify a subject at risk for developing diabetes. In certain embodiments a GTT is used to identify a subject having insulin resistance.

"Insulin Tolerance Test (ITT)" means a test performed to measure insulin sensitivity through hormone response to the stress of a low blood sugar level. In certain embodiments, a ITT is used to test for pre-diabetes. In certain embodiments, a ITT is used to identify a subject with diabetes. In certain embodiments, a ITT is used to identify a subject at risk for developing diabetes. In certain embodiments a ITT is used to identify a subject having insulin resistance.

"Metabolic rate" means the rate of metabolism or the amount of energy expended in a given period. "Basal metabolic rate" means the amount of energy expended while at rest in a neutrally temperate environment, in the post-absorptive state (meaning that the digestive system is inactive, which requires about twelve hours of fasting in humans); the release of energy in this state is sufficient only for the functioning of the vital organs, such as the heart, lungs, brain and the rest of the nervous system, liver, kidneys, sex organs, muscles and skin.

"Anti-miR" means an oligonucleotide having a nucleobase sequence complementary to a microRNA. In certain embodiments, an anti-miR is a modified oligonucleotide.

"Subject" means a human or non-human animal selected for treatment or therapy.

"Subject in need thereof" means a subject identified as in need of a therapy or treatment. In certain embodiments, a subject has liver cancer. In such embodiments, a subject has one or more clinical indications of liver cancer or is at risk for developing liver cancer.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein. "Administered concomitantly" refers to the administration of at least two agents to a subject in any manner in which the pharmacological effects of both are manifest in the subject at the same time. Concomitant administration does not require that both agents be administered in a single pharmaceutical composition, in the same dosage form, or by the same route of administration. The time during which the effects of the agents need not be identical. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, surgical resection, liver transplant, and/or chemoembolization.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Improved liver function" means the change in liver function toward normal limits. In certain embodiments, liver function is assessed by measuring molecules found in a subject's blood. For example, in certain embodiments, improved liver function is measured by a reduction in blood liver transaminase levels.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid. In certain embodiments, an has a nucleobase sequence that is complementary to a region of a target nucleic acid. For example, in certain such embodiments an is complementary to a region of a miRNA stem-loop sequence. In certain such embodiments, an is fully complementary to a region of a miRNA stem-loop sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that an oligomeric compound is capable of hybrizing to a target nucleic acid under stringent hybridization conditions.

"Fully complementary" means each nucleobase of an oligomeric compound is capable of pairing with a nucleobase at each corresponding position in a target nucleic acid. For example, in certain embodiments, an oligomeric compound wherein each nucleobase has complementarity to a nucleobase within a region of a miRNA stem-loop sequence is fully complementary to the miRNA stem-loop sequence.

"Percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound. In certain embodiments, percent complementarity of an means the number of nucleobases that are complementary to the target nucleic acid, divided by the length of the modified oligonucleotide.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical" means having the same nucleobase sequence.

"miR-103" means the mature miRNA having the nucleobase sequence set forth in SEQ ID NO: 1 (AGCAGCAUU-GUACAGGGCUAUGA).

"miR-107" means the mature miRNA having the nucleobase sequence set forth in SEQ ID NO: 2 (AGCAGCAUU-GUACAGGGCUAUCA). "miR-103-1 stem-loop sequence" means the miR-103 precursor having the nucleobase sequence set forth in SEQ ID NO: 3 (UACUGCCCUCG-GCUUCUUUACAGUGCUGCCUUGUUG-CAUAUGGAUCAAGCAGCAUUGUACA GGGC-UAUGAAGGCAUUG).

"miR-103-2" means the miR-103 precursor having the nucleobase sequence set forth in SEQ ID NO: 4 (UU-GUGCUUUCAGCUUCUUUACAGUGCUGC-CUUGUAGCAUUCAGGUCAAGCAGCAUUGUACA GGGCUAUGAAAGAACCA.

"miR-107 stem loop sequence" means the miR-107 precursor having the nucleobase sequence set forth in SEQ ID NO: 5 (CUCUCUGCUUUCAGCUUCUUUACAGUG-UUGCCUUGUGGGCAUGGAGUUCAAGCAGCAUUGUA CAGGGCUAUCAAAGCACAGA).

"miR-103/miR-107" means a microRNA having the nucleobase sequence of SEQ ID NO: 1 or SEQ ID NO: 2.

"MicroRNA" means a non-coding RNA between 18 and 25 nucleobases in length, which is the product of cleavage of a pre-miRNA by the enzyme Dicer. Examples of mature miRNAs are found in the miRNA database known as miR-Base (http://microrna.sanger.ac.uk/). In certain embodiments, microRNA is abbreviated as "miRNA" or "miR."

"Pre-miRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (http://microrna.sanger.ac.uk/).

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Monocistronic transcript" means a miRNA precursor containing a single miRNA sequence.

"Polycistronic transcript" means a miRNA precursor containing two or more miRNA sequences.

"Seed sequence" means nucleotides 2 to 6 or 2 to 7 from the 5'-end of a mature miRNA sequence.

"Compound comprising an oligonucleotide consisting of" a number of linked nucleosides means a compound that includes an oligonucleotide having the specified number of linked nucleosides. Thus, the compound may include additional substituents or conjugates. Unless otherwise indicated, the compound does not include any additional nucleosides beyond those of the oligonucleotide. "Oligomeric compound" means a compound comprising a polymer of linked monomeric subunits.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"Modified oligonucleotide" means an oligonucleotide having one or more modifications relative to a naturally occurring terminus, sugar, nucleobase, and/or internucleoside linkage.

"Single-stranded modified oligonucleotide" means an which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a sugar modified by the bridging of two non-geminal ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"Motif" means a pattern of modified and/or unmodified nucleobases, sugars, and/or internucleoside linkages in an oligonucleotide.

A "fully modified oligonucleotide" means each nucleobase, each sugar, and/or each internucleoside linkage is modified.

A "uniformly modified oligonucleotide" means each nucleobase, each sugar, and/or each internucleoside linkage has the same modification throughout the modified oligonucleotide.

A "gapmer" means a modified oligonucleotide having an internal region of linked nucleosides positioned between two external regions of linked nucleosides, where the nucleosides of the internal region comprise a sugar moiety different than that of the nucleosides of each external region.

A "gap segment" is an internal region of a gapmer that is positioned between the external regions.

A "wing segment" is an external region of a gapmer that is located at the 5' or 3' terminus of the internal region.

A "symmetric gapmer" means each nucleoside of each external region comprises the same sugar modification.

An "asymmetric gapmer" means each nucleoside of one external region comprises a first sugar modification, and each nucleoside of the other external region comprises a second sugar modification.

A "stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

A "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

A "stabilizing internucleoside linkage" means an internucleoside linkage that provides improved nuclease stability to an oligonucleotide relative to that provided by a phosphodiester internucleoside linkage. In one embodiment, a stabilizing internucleoside linkage is a phosphorothioate internucleoside linkage.

Overview

Metabolic disorders are characterized by one or more abnormalities in metabolic function in the body. Certain metabolic disorders are related to defects in how the body uses blood glucose, resulting in abnormally high levels of blood glucose. Metabolic disorders may also be characterized by a deficiency in insulin production, or a deficiency in sensitivity to insulin. Metabolic disorders affect millions of people worldwide, and can be life-threatening disorders. As such, there is a need for method and compositions to treat, prevent, or delay the onset of metabolic disorders.

As illustrated herein, the administration of oligonucleotides complementary to miR-103 and/or miR-107 resulted in improved blood glucose levels, decreased gluconeogenesis, enhanced insulin sensitivity, and decreased plasma cholesterol. These effects were observed in animal models of diabetes/insulin resistance. Also observed was a decrease in body weight, which was due to a decrease in body fat. As miR-103 and miR-107 differ by one nucleobase, an oligonucleotide having a sequence complementary to the nucleobase sequence of miR-103 may hybridize to and inhibit the activity of both miR-103 and miR-107. Likewise, an oligonucleotide having a sequence complementary to the nucleobase sequence of miR-107 may hybridize to and inhibit the activity of both miR-103 and miR-107. As such, oligonucleotides complementary to either one or both of miR-103 and miR-107 may be used to achieve the phenotypic outcomes described herein.

Administration of a compound comprising an oligonucleotide complementary to miR-103, miR-107 or a precursor thereof may result in one or more clinically desirable outcomes. Such clinically desirable outcomes include but are not limited to reduced blood glucose levels, reduced HbA1c levels, improved glucose tolerance, improved insulin resistance, and reduced gluconeogenesis.

Accordingly, provided herein are methods and compositions to reduce blood glucose levels, decrease gluconeogenesis, improve insulin sensitivity, and decrease plasma cholesterol. Also provided herein are methods to treat, prevent, or delay the onset of metabolic disorders that are related to elevated blood glucose levels, increased gluconeogenesis, impaired insulin sensitivity, and increased plasma cholesterol. In certain embodiments, metabolic disorders include, but are not limited to, prediabetes, diabetes, including Type 1 or Type 2 diabetes, metabolic syndrome, obesity, diabetic dyslipidemia, hyperglycemia, hypoglycemia, and hyperinsulinemia. In certain embodiments, a subject having a metabolic disorder also has a fatty liver disease. In certain embodiments, fatty liver diseases include, but are not limited to, non-alcoholic fatty liver disease, alchoholic fatty liver disease, and non-alchoholic steatohepatitis.

In certain embodiments, provided herein are methods for reducing blood glucose levels in a subject comprising administering to the subject a compound comprising an oligonucleotide consisting of 12 to 30 linked nucleosides and having a nucleobase sequence complementary to miR-103 and/or miR-107.

In certain embodiments, provided herein are methods for reducing blood glucose levels in a subject comprising administering to the subject a compound comprising an oligonucleotide consisting of 7 to 12 linked nucleosides and having a nucleobase sequence complementary to miR-103 and miR-107.

In certain embodiments, the methods provided herein comprise measuring blood glucose levels. Blood glucose levels may be measured before and/or after administration of a compound comprising an oligonucleotide consisting of 12 to 30 linked nucleosides and having a nucleobase sequence complementary to miR-103 and/or miR-107. Blood glucose levels may be measured in whole blood, or may be measured in plasma. Blood glucose levels may be measured in a clinical laboratory, or may be measured using a blood glucose meter.

In certain embodiments, blood glucose levels are measured in a subject when the subject has fasted for at least 8 hours. In certain embodiments, blood glucose levels are measured at random times, and the measurement is not timed according to the intake of food or drink. In certain embodiments, blood glucose levels are measured in the post-prandial state, i.e. after the subject has eaten a meal. In certain embodiments, blood glucose levels are measured in a subject two hours after the subject has eaten a meal. In certain embodiments, blood glucose levels are measured at timed intervals following administration of glucose to the subject, in order to determine how quickly the subject's body clears glucose from the blood. Any measurements of blood glucose levels may be made in whole blood or in plasma.

In certain embodiments, the subject has elevated blood glucose levels. In certain embodiments, a subject is identified as having elevated blood glucose levels. Such identification is typically made by a medical professional. In certain embodiments, an elevated blood glucose levels is a fasting blood glucose level between 100 and 125 mg/dL. In certain embodiments, an elevated blood glucose level is a fasting blood glucose level above 126 mg/dL. In certain embodiments, an elevated blood glucose level is a two-hour post-prandial glucose level between 140 and 199 mg/dL. In certain embodiments, an elevated blood glucose level is a two-hour post-prandial glucose level at 200 mg/dL or higher.

In certain embodiments, a subject having elevated blood glucose levels has pre-diabetes. In certain embodiments, a subject is identified as having pre-diabetes. In certain such embodiments, the subject has a fasting blood glucose level between 100 and 125 mg/dL. In certain such embodiments, the subject has a two-hour post-prandial blood glucose level between 140 and 199 mg/dL. A diagnosis of pre-diabetes is typically made by a medical professional, who may consider factors in addition to blood glucose levels when determining whether a subject has pre-diabetes.

In certain embodiments, a subject having elevated blood glucose levels has diabetes. In certain embodiments, a subject is identified as having diabetes according to the subject's blood glucose levels. In certain such embodiments, the subject has a fasting blood glucose level above 126 mg/dL. In certain such embodiments, the subject has a two-hour post-prandial blood glucose level at or above 200 mg/dL. A diagnosis of diabetes is typically made by a medical professional, who may consider factors in addition to blood glucose levels when determining whether a subject has diabetes.

In certain embodiments, the method provided herein comprise monitoring blood glucose levels before administration of a compound comprising an oligonucleotide consisting of 12 to 30 linked nucleosides and having a nucleobase sequence complementary to miR-103 and/or miR-107. In certain embodiments, the methods provided herein comprise measuring blood glucose levels after administration of a compound comprising an oligonucleotide consisting of 12 to 30 linked nucleosides and having a nucleobase sequence complementary to miR-103 and/or miR-107. In certain embodiments, a subject measures blood glucose levels one or more times daily.

In certain embodiments, methods for reducing blood glucose levels comprise reducing a subject's blood glucose levels to blood glucose levels determined as desirable by medical organizations, such as the American Diabetes Association or the World Health Organization. In certain embodiments, blood glucose levels are reduced below 130 mg/dL when measured before a subject has had a meal. In certain embodiments, blood glucose levels are reduced to below 180 mg/dL when measured after a subject has had a meal.

In certain embodiments, the administration occurs at least once per week. In certain embodiments, the administration occurs once every two weeks. In certain embodiments, the administration occurs once every three weeks. In certain embodiments, the administration occurs once every four weeks. The frequency of administration may be set by a medical professional to achieve a desirable blood glucose level in a subject. The frequency of administration may be dependent upon a subject's blood glucose levels. For example, in certain embodiments, administration may be more frequent when a subject has elevated blood glucose levels.

Measurements of HbA1c levels may be used to determine how well a subject's blood glucose levels are controlled over time. HbA1c levels are an indication of the amount of glycated hemoglobin in the blood, and can provide an estimate of how well a subject's blood glucose levels have been managed over 2-3 month period prior to the measurement of HbA1c levels. High HbA1c levels may put a subject at risk for developing complications related to diabetes, such as eye disease, heart disease, kidney disease, nerve damage, or stroke. As such, in certain embodiments it is desirable that a subject's HbA1c levels be within ranges that are considered normal by a medical professional. In certain embodiments, an HbA1c level of 6% or less is normal. In certain embodiments, a medical professional may recommend that a subject's HbA1c level be 7% or less. In certain embodiments, the administering results in reduced HbA1c levels.

In certain embodiments, a subject having elevated blood glucose levels is insulin resistant. One of the main functions of insulin is to lower blood glucose levels. A subject whose cells are sensitive to the effects of insulin needs only a relatively small amount of insulin to keep blood glucose levels in the normal range. A subject who is insulin resistant requires more insulin to get the same blood glucose-lowering effects. Insulin resistance may cause hyperinsulinemia. Hyperinsulinemia may be associated with high blood pressure, heart disease and heart failure, obesity (particularly abdominal obesity), osteoporosis, and certain types of cancer, such as colon, breast, and prostate cancer.

Insulin resistance may be detected using a procedure known as the hyperinsulinemic euglycemic clamp, which measures the amount of glucose necessary to compensate for an increased insulin level without causing hypoglycemia. During the procedure, insulin is infused at 10-120 mU per m$^2$ per minute. In order to compensate for the insulin infusion, a 20% solution of glucose is infused to maintain blood sugar levels between 5 and 5.5 mmol/L. The rate of glucose infusion is determined by checking the blood sugar levels every 5 to 10 minutes. Low-dose insulin infusions are more useful for assessing the response of the liver, whereas high-dose insulin infusions are useful for assessing peripheral (i.e., muscle and fat) insulin action. The rate of glucose infusion during the last 30 minutes of the test determines insulin sensitivity. If high levels (7.5 mg/min or higher) are required, the subject is insulin-sensitive. Very low levels (4.0 mg/min or lower) indicate that the subject is resistant to insulin action. Levels between 4.0 and 7.5 mg/min are not definitive and suggest impaired glucose tolerance. Impaired glucose tolerance may be an early sign of insulin resistance. Glucose tracers, such as 3-$^3$H glucose, 6,6$^2$H-glucose, or 1-$^{13}$C glucose, may be used in the procedure. Other radioactive forms of glucose may be employed in a research setting. Prior to beginning the hyperinsulinemic period, a 3 hour tracer infusion enables the determination of the basal rate of glucose production. During the clamp procedure, the plasma tracer concentrations enable the calculation of whole-body insulin-stimulated glucose metabolism, as well as the production of glucose by the body (i.e., endogenous glucose production).

In certain embodiments, provided herein are methods for improving insulin resistance in a subject comprising administering a subject to the subject a compound comprising an oligonucleotide consisting of 12 to 30 linked nucleosides and having a nucleobase sequence complementary to miR-103, miR-107, or precursor thereof. In certain embodiments, the subject has insulin resistance. In certain embodiments, the methods comprise selecting a subject having insulin resistance.

In certain embodiments, provided herein are methods for improving insulin resistance in a subject comprising administering a subject to the subject a compound comprising an oligonucleotide consisting of 7 to 12 linked nucleosides and having a nucleobase sequence complementary to miR-103 and miR-107. In certain embodiments, a subject having elevated blood glucose levels has insulin resistance.

In certain embodiments, a subject having diabetes has insulin resistance. In certain embodiments, a subject having type 2 diabetes has insulin resistance. In certain embodiments, a subject having type 1 diabetes has insulin resistance.

In certain embodiments, provided herein are methods for reducing gluconeogenesis in a subject comprising administering to the subject a compound comprising an oligonucleotide consisting of 12 to 30 linked nucleosides and having a nucleobase sequence complementary to miR-103, miR-107, or precursor thereof. In certain embodiments, the subject has elevated gluconeogenesis. In certain embodiments, the subject is identified as having elevated gluconeogenesis. In certain embodiments, the administering results in a reduction in gluconeogenesis. In certain embodiments, a pyruvate tolerance test is used to measure gluconeogenesis in a subject. In certain embodiments, blood glucose levels are used to measure gluconeogenesis in a subject. In certain embodiments, the rate of gluconeogenesis is measured in a subject. In certain embodiments, a reduction in gluconeogenesis is a reduction in the rate of gluconeogenesis. In certain embodiments, the rate of gluconeogenesis is measured in the subject prior to administration. In certain embodiments, the rate of gluconeogenesis is measured in the subject after administration.

In certain embodiments, provided herein are methods for reducing plasma cholesterol in a subject comprising administering to the subject a compound comprising an oligonucleotide consisting of 12 to 30 linked nucleosides and having a nucleobase sequence complementary to miR-103, miR-107, or precursor thereof. In certain embodiments, the subject has elevated plasma cholesterol. In certain embodiments, the subject is identified as having elevated plasma cholesterol. In certain embodiments, the administering reduces plasma cholesterol. In certain embodiments, the plasma cholesterol is plasma LDL-cholesterol. In certain embodiments, the plasma cholesterol is plasma VLDL-cholesterol.

In certain embodiments, provided herein are methods for reducing plasma cholesterol in a subject comprising administering to the subject a compound comprising an oligonucleotide consisting of 7 to 12 linked nucleosides and having a nucleobase sequence complementary to miR-103 and miR-107.

In certain embodiments, provided herein are methods for treating a metabolic disorder in a subject comprising administering to the subject a compound comprising an oligonucleotide consisting of 12 to 30 linked nucleosides and having a nucleobase sequence complementary to miR-103, miR-107, or a precursor thereof. In certain embodiments, the subject has a metabolic disorder. In certain embodiments, the subject is identified as having a metabolic disorder. In certain embodiments, a metabolic disorder includes, without limitation, prediabetes, diabetes (including Type 1 or Type 2 diabetes), metabolic syndrome, obesity, or diabetic dyslipidemia, hyperglycemia, hypoglycemia, and hyperinsulinemia. In certain embodiments, the subject is diagnosed with one or more metabolic disorders. A subject may be diagnosed with a metabolic disorder following the administration of medical tests well-known to those in the medical profession.

In certain embodiments, provided herein are methods for treating a metabolic disorder in a subject comprising administering to the subject a compound comprising an oligonucleotide consisting of 7 to 12 linked nucleosides and having a nucleobase sequence complementary to miR-103 and miR-107.

Fatty liver diseases are often associated with metabolic disorders. In certain embodiments, a subject having a metabolic disorder also has a fatty liver disease. In certain embodiments, a fatty liver disease is non-alcoholic fatty liver disease. In certain embodiments, a fatty liver disease is alcoholic fatty liver disease. In certain embodiments, a fatty liver disease is alcoholic steatohepatitis.

In certain embodiments, provided herein are methods for preventing the onset of a metabolic disorder in a subject comprising administering to the subject a compound comprising an oligonucleotide consisting of 12 to 30 linked nucleosides and having a nucleobase sequence complementary to miR-103, miR-107, or a precursor thereof. In certain embodiments, the subject is at risk for developing a metabolic disorder. In certain embodiments, the subject is identified being at risk for developing a metabolic disorder. In certain embodiments, a metabolic disorder is prediabetes, diabetes (including Type 1 or Type 2 diabetes), metabolic syndrome, obesity, or diabetic dyslipidemia, hyperglycemia, hypoglycemia, hyperinsulinemia, ketoacidosis and celiac disease.

In certain embodiments, provided herein are methods for preventing the onset of a metabolic disorder in a subject comprising administering to the subject a compound comprising an oligonucleotide consisting of 7 to 12 linked nucleosides and having a nucleobase sequence complementary to miR-103 and miR-107.

In certain embodiments, provided herein are methods for delaying the onset of a metabolic disorder in a subject comprising administering to the subject a compound comprising an oligonucleotide consisting of 12 to 30 linked nucleosides and having a nucleobase sequence complementary to miR-103, miR-107, or a precursor thereof. In certain embodiments, the subject is at risk for developing a metabolic disorder. In certain embodiments, the subject is identified being at risk for developing a metabolic disorder. In certain embodiments, a metabolic disorder includes, without limitation, prediabetes, diabetes (including Type 1 or Type 2 diabetes), metabolic syndrome, obesity, or diabetic dyslipidemia, hyperglycemia, hypoglycemia, and hyperinsulinemia.

In certain embodiments, provided herein are methods for delaying the onset of a metabolic disorder in a subject comprising administering to the subject a compound comprising an oligonucleotide consisting of 7 to 12 linked nucleosides and having a nucleobase sequence complementary to miR-103 and miR-107.

In certain embodiments, a subject has one or more metabolic disorders. In certain embodiments, a subject has been diagnosed with one or more metabolic disorders. A subject may be diagnosed with a metabolic disorder following the administration of medical tests well-known to those in the medical profession.

A subject's response to treatment may be evaluated by tests similar to those used to diagnosis the metabolic disorder, including blood glucose level tests, glucose tolerance tests, and HbA1c tests. Response to treatment may also be assessed by comparing post-treatment test results to pre-treatment test results.

Fatty liver diseases may be associated with metabolic disorders. In certain embodiments, a fatty liver disease is non-alcoholic fatty liver disease. In certain embodiments, a fatty liver disease is alcoholic fatty liver disease. In certain embodiments, a fatty liver disease is alcoholic steatohepatitis.

In certain embodiments, provided herein are methods for treating fatty liver disease in a subject comprising administering to the subject a compound comprising an oligonucleotide consisting of 12 to 30 linked nucleosides and having a nucleobase sequence complementary to miR-103, miR-107, or a precursor thereof.

In certain embodiments, provided herein are methods for treating fatty liver disease in a subject comprising administering to the subject a compound comprising an oligonucleotide consisting of 7 to 12 linked nucleosides and having a nucleobase sequence complementary to miR-103 and miR-107.

In certain embodiments, provided herein are methods for preventing a fatty liver disease in a subject comprising administering to the subject a compound comprising an oligonucleotide consisting of 12 to 30 linked nucleosides and having a nucleobase sequence complementary to miR-103, miR-107, or a precursor thereof. In certain such embodiments, the subject is at risk for developing a fatty liver disease.

In certain embodiments, provided herein are methods for preventing fatty liver disease in a subject comprising administering to the subject a compound comprising an oligonucleotide consisting of 7 to 12 linked nucleosides and having a nucleobase sequence complementary to miR-103 and miR-107.

In certain embodiments, provided herein are methods for delaying the onset of a fatty liver disease in a subject comprising administering to the subject a compound comprising an oligonucleotide consisting of 12 to 30 linked nucleosides and having a nucleobase sequence complementary to miR-103, miR-107, or a precursor thereof. In certain such embodiments, the subject is at risk for developing a fatty liver disease.

In certain embodiments, provided herein are methods for delaying the onset of fatty liver disease in a subject comprising administering to the subject a compound comprising an oligonucleotide consisting of 7 to 12 linked nucleosides and having a nucleobase sequence complementary to miR-103 and miR-107.

In certain embodiments, the activity of miR-103 and/or miR-107 is inhibited by use of a microRNA sponge, which comprises one or more sequences having nucleobase complementarity to miR-103 and/or miR-107. "MicroRNA sponge" means a competitive inhibitor of a microRNA in the form of a transcript expressed from a strong promoter, containing multiple, tandem binding sites to a microRNA of interest. When vectors encoding these sponges are introduced into cells, sponges derepress microRNA targets at least as strongly as chemically modified antisense oligonucleotides. They specifically inhibit microRNAs with a complementary heptameric seed, such that a single sponge can be used to block an entire microRNA seed family. In certain embodiments, the microRNA seed family comprises miR-103 and miR-107.

Certain Compounds

The compounds provided herein are useful for the treatment of metabolic disorders. In certain embodiments, the compound comprises an oligonucleotide. In certain such embodiments, the compound consists of an oligonucleotide. In certain embodiments, the oligonucleotide is a modified oligonucleotide.

In certain such embodiments, the compound comprises an oligonucleotide hybridized to a complementary strand, i.e. the compound comprises a double-stranded oligomeric compound. In certain embodiments, the hybridization of an oligonucleotide to a complementary strand forms at least one blunt end. In certain such embodiments, the hybridization of an oligonucleotide to a complementary strand forms a blunt end at each terminus of the double-stranded oligomeric compound. In certain embodiments, a terminus of an oligonucleotide comprises one or more additional linked nucleosides relative to the number of linked nucleosides of the complementary strand. In certain embodiments, the one or more additional nucleosides are at the 5' terminus of an oligonucleotide. In certain embodiments, the one or more additional nucleosides are at the 3' terminus of an oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of an oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, the compound comprises an oligonucleotide conjugated to one or more moieties which enhance the activity, cellular distribution or cellular uptake of the resulting antisense oligonucleotides. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to an oligonucleotide. In certain embodiments, a conjugate group is attached to an oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises an oligonucleotide having one or more stabilizing groups that are attached to one or both termini of an oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Nucleobase Sequences

In certain embodiments, an oligonucleotide has a sequence that is complementary to a miRNA or a precursor thereof. Nucleobase sequences of mature miRNAs and their corresponding stem-loop sequences described herein are the sequences found in miRBase, an online searchable database of miRNA sequences and annotation, found at http://microrna.sanger.ac.uk/. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miR-NAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. The compositions of the present invention encompass modified oligonucleotides that are complementary to any nucleobase sequence version of the miRNAs described herein.

In certain embodiments, an oligonucleotide has a nucleobase sequence that is complementary to a miRNA or a precursor thereof. Accordingly, in certain embodiments the nucleobase sequence of an oligonucleotide may have one or more mismatched basepairs with respect to its target miRNA or precursor sequence, and remains capable of hybridizing to its target sequence. In certain embodiments, an oligonucleotide has a nucleobase sequence that is fully complementary to a miRNA or precursor thereof.

In certain embodiments, an oligonucleotide has a sequence that is complementary to a nucleobase sequence of a miRNA stem-loop sequence selected from the miR-103-1 stem-loop sequence, the miR-103-2 stem loop sequence, and the miR-107 stem loop sequence.

In certain embodiments, an oligonucleotide has a sequence that is complementary to a nucleobase sequence of a miRNA, where the nucleobase sequence of the miRNA is selected from SEQ ID NO: 1 or 2.

In certain embodiments, an oligonucleotide has a nucleobase sequence that is complementary to a region of the miR-103-1 stem-loop sequence (SEQ ID NO: 3). In certain embodiments, an oligonucleotide has a nucleobase sequence that is complementary to the region of nucleobases 48-70 of SEQ ID NO: 3.

In certain embodiments, an oligonucleotide has a nucleobase sequence that is complementary to a region of the miR-103-2 stem-loop sequence (SEQ ID NO: 4). In certain embodiments, an oligonucleotide has a nucleobase sequence that is complementary to the region of nucleobases 48-70 of SEQ ID NO: 4.

In certain embodiments, an oligonucleotide has a nucleobase sequence that is complementary to a region of the miR-107 stem-loop sequence (SEQ ID NO: 5). In certain embodiments, an oligonucleotide has a nucleobase sequence that is complementary to the region of nucleobases 50-72 of SEQ ID NO: 5.

In certain embodiments, an oligonucleotide has a nucleobase sequence that is complementary to the nucleobase sequence of miR-103 (SEQ ID NO: 1). In certain embodiments, an oligonucleotide has a nucleobase sequence comprising the nucleobase sequence UCAUAGCCCUGUA-CAAUGCUGCU (SEQ ID NO: 6). In certain embodiments, an oligonucleotide has a nucleobase sequence consisting of the nucleobase sequence UCAUAGCCCUGUA-CAAUGCUGCU (SEQ ID NO: 6).

In certain embodiments, an oligonucleotide has a nucleobase sequence that is complementary to the nucleobase sequence of miR-107 (SEQ ID NO: 2). In certain embodiments, an oligonucleotide has a nucleobase sequence comprising the nucleobase sequence UGAUAGCCCUGUA-CAAUGCUGCU (SEQ ID NO: 7). In certain embodiments, an oligonucleotide has a nucleobase sequence consisting of the nucleobase sequence UGAUAGCCCUGUA-CAAUGCUGCU (SEQ ID NO: 7).

In certain embodiments, an oligonucleotide has a nucleobase sequence that is complementary to the nucleobase sequence of miR-103 or miR-107, and is capable of inhibiting the activity of both miR-103 and miR-107, as a result of the sequence similarity between miR-103 and miR-107. An oligonucleotide having a nucleobase sequence fully complementary to miR-103 will have only one mismatch relative to miR-107, thus such an oligonucleotide fully complementary to miR-103 may inhibit the activity of both miR-103 and miR-107. Likewise, an oligonucleotide having a nucleobase sequence fully complementary to miR-107 will have only one mismatch relative to miR-103, thus such an oligonucleotide fully complementary to miR-107 may inhibit the activity of both miR-103 and miR-107. As such, oligonucleotides complementary to one or both of miR-103 and miR-107 may be used in the methods provided herein. In certain embodiments, an oligonucleotide has a nucleobase sequence that is complementary to nucleobases 1-21 of SEQ ID NO: 1 (miR-103) or to nucleobases 1-21 of SEQ ID NO: 2 (miR-107). Such oligonucleotides are 100% complementary to both miR-103 and miR-107. In certain such embodiments, an oligonucleotide comprises the nucleobase sequence AUAGC- CCUGUACAAUGCUGCU (SEQ ID NO: 8). In certain such embodiments, an oligonucleotide consists of the nucleobase sequence AUAGCCCUGUACAAUGCUGCU (SEQ ID NO: 8).

In certain embodiments, an oligonucleotide comprises a nucleobase sequence that is complementary to a seed sequence shared between miR-103 and miR-107. Oligonucleotides having any length described herein may comprise a seed-match sequence. In certain such embodiments, the modified oligonucleotide consists of 7 linked nucleosides. In certain embodiments, the modified oligonucleotide consists of 8 linked nucleosides. In certain embodiments, the modified oligonucleotide consists of 9 linked nucleosides. In certain embodiments, the modified oligonucleotide consists of 10 linked nucleosides. In certain embodiments, the modified oligonucleotide consists of 11 linked nucleosides. In certain embodiments, the modified oligonucleotide consists of 12 linked nucleosides.

In certain embodiments, the nucleobase sequence of the modified oligonucleotide is comprises the nucleobase sequence AUGCUGCU (SEQ ID NO: 10), which is complementary to nucleotides 1-8 of miR-103 (SEQ ID NO: 1) and miR-107 (SEQ ID NO: 2). In certain embodiments, the nucleobase sequence of the modified oligonucleotide comprises the nucleobase sequence AUGCUGC (SEQ ID NO: 11) which is complementary to nucleotides 2-8 of miR-103 and miR-107. In certain embodiments, the nucleobase sequence of the modified oligonucleotide comprises the nucleobase sequence UGCUGCU (SEQ ID NO: 12) which is complementary to nucleotides 1-7 of miR-103 and miR-107. In certain embodiments, the nucleobase sequence of the modified oligonucleotide comprises the nucleobase sequence AUGCUGC (SEQ ID NO: 13) which is complementary to nucleotides 2-8 of miR-103 and miR-107. In certain embodiments, the nucleobase sequence of the modified oligonucleotide comprises the nucleobase sequence GCUGCU (SEQ ID NO: 14) which is complementary to nucleotides 1-6 of miR-103 or miR-107. In certain embodiments, the nucleobase sequence of the modified oligonucleotide comprises the nucleobase sequence UGCUGC (SEQ ID NO: 15) which is complementary to nucleotides 2-7 of miR-103 and miR-107. In certain embodiments, the nucleobase sequence of the modified oligonucleotide comprises the nucleobase sequence AUGCUG (SEQ ID NO: 16) which is complementary to nucleotides 3-8 of miR-103 and miR-107.

Modified oligonucleotides consisting of 7, 8, 9, 10, or 11 linked nucleosides and complementary to nucleotides 2 through 8 or 2 through 7 of a miRNA have been shown to inhibit activity of the miRNA. Modified oligonucleotides consisting of 8 linked nucleosides and complementary to nucleotides 2 through 9 of a miRNA have also been shown to inhibit activity of the miRNA. Certain of these modified oligonucleotides have an LNA sugar modification at each nucleoside. Such inhibitory activity is described in PCT Publication No. WO/2009/043353, which is herein incorporated by reference in its entirety for its description of modified oligonucleotides targeting miRNA seed sequences.

In certain embodiments, an oligonucleotide has a nucleobase sequence that is complementary to a nucleobase sequence having at least 80% identity to a nucleobase sequence of a miR stem-loop sequence selected from SEQ ID NO: 3, 4, and 5. In certain embodiments, an oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miR stem-loop sequence selected from SEQ ID NOs 3, 4, and 5.

In certain embodiments, an oligonucleotide has a nucleobase sequence that is complementary to a nucleobase sequence having at least 80% identity to a nucleobase sequence of a miRNA having a nucleobase sequence selected from SEQ ID NOs 1 and 2. In certain embodiments, an oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miRNA nucleobase sequence selected from SEQ ID NOs 1 and 2.

In certain embodiments, a nucleobase sequence of an oligonucleotide is fully complementary to a miRNA nucleobase sequence listed herein, or a precursor thereof. In certain embodiments, an oligonucleotide has a nucleobase sequence having one mismatch with respect to the nucleobase sequence of the mature miRNA, or a precursor thereof. In certain embodiments, an oligonucleotide has a nucleobase sequence having two mismatches with respect to the nucleobase sequence of the miRNA, or a precursor thereof. In certain such embodiments, an oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, an oligonucleotide consists of a number of linked nucleosides that is equal to the length of the mature miR to which it is complementary.

In certain embodiments, the number of linked nucleosides of an oligonucleotide is less than the length of the mature miRNA to which it is complementary. In certain such embodiments, the number of linked nucleosides of an oligonucleotide is one less than the length of the mature miR to which it is complementary. In certain such embodiments, an oligonucleotide has one less nucleoside at the 5' terminus. In certain such embodiments, an oligonucleotide has one less nucleoside at the 3' terminus. In certain such embodiments, an oligonucleotide has two fewer nucleosides at the 5' terminus. In certain such embodiments, an oligonucleotide has two fewer nucleosides at the 3' terminus. An oligonucleotide having a number of linked nucleosides that is less than the length of the miRNA, wherein each nucleobase of an oligonucleotide is complementary to each nucleobase at a corresponding position in a miRNA, is considered to be an oligonucleotide having a nucleobase sequence that is fully complementary to a portion of a miRNA sequence.

In certain embodiments, the number of linked nucleosides of an oligonucleotide is greater than the length of the miRNA to which it is complementary. In certain such embodiments, the nucleobase of an additional nucleoside is complementary to a nucleobase of a miRNA stem-loop sequence. In certain embodiments, the number of linked nucleosides of an oligonucleotide is one greater than the length of the miRNA to which it is complementary. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of an oligonucleotide is two greater than the length of the miRNA to which it is complementary. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide.

In certain embodiments, a portion of the nucleobase sequence of an oligonucleotide is fully complementary to the nucleobase sequence of the miRNA, but the entire modified oligonucleotide is not fully complementary to the miRNA. In certain such embodiments, the number of nucleosides of an oligonucleotide having a fully complementary portion is greater than the length of the miRNA. For example, an oligonucleotide consisting of 24 linked nucleosides, where the nucleobases of nucleosides 1 through 23 are each complementary to a corresponding position of a miRNA that is 23 nucleobases in length, has a 23 nucleoside portion that is fully complementary to the nucleobase sequence of the miRNA and approximately 96% overall complementarity to the nucleobase sequence of the miRNA.

In certain embodiments, the nucleobase sequence of an oligonucleotide is fully complementary to a portion of the nucleobase sequence of a miRNA. For example, an oligonucleotide consisting of 22 linked nucleosides, where the nucleobases of nucleosides 1 through 22 are each complementary to a corresponding position of a miRNA that is 23 nucleobases in length, is fully complementary to a 22 nucleobase portion of the nucleobase sequence of a miRNA. Such an oligonucleotide has approximately 96% overall complementarity to the nucleobase sequence of the entire miRNA, and has 100% complementarity to a 22 nucleobase portion of the miRNA.

In certain embodiments, a portion of the nucleobase sequence of an oligonucleotide is fully complementary to a portion of the nucleobase sequence of a miRNA, or a precursor thereof. In certain such embodiments, 15 contiguous nucleobases of an oligonucleotide are each complementary to 15 contiguous nucleobases of a miRNA, or a precursor thereof. In certain such embodiments, 16 contiguous nucleobases of an oligonucleotide are each complementary to 16 contiguous nucleobases of a miRNA, or a precursor thereof. In certain such embodiments, 17 contiguous nucleobases of an oligonucleotide are each complementary to 17 contiguous nucleobases of a miRNA, or a precursor thereof. In certain such embodiments, 18 contiguous nucleobases of an oligonucleotide are each complementary to 18 contiguous nucleobases of a miRNA, or a precursor thereof. In certain such embodiments, 19 contiguous nucleobases of an oligonucleotide are each complementary to 19 contiguous nucleobases of a miRNA, or a precursor thereof. In certain such embodiments, 20 contiguous nucleobases of an oligonucleotide are each complementary to 20 contiguous nucleobases of a miRNA, or a precursor thereof. In certain such embodiments, 22 contiguous nucleobases of an oligonucleotide are each complementary to 22 contiguous nucleobases of a miRNA, or a precursor thereof. In certain such embodiments, 23 contiguous nucleobases of an oligonucleotide are each complementary to 23 contiguous nucleobases of a miRNA, or a precursor thereof. In certain such embodiments, 24 contiguous nucleobases of an oligonucleotide are each complementary to 24 contiguous nucleobases of a miRNA, or a precursor thereof.

The nucleobase sequences set forth herein, including but not limited to those found in the Examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$C-GAUCG," wherein $^{me}$C indicates a cytosine base comprising a methyl group at the 5-position.

Certain Modified Oligonucleotides

In certain embodiments, an oligonucleotide consists of 7 to 25 linked nucleosides. In certain embodiments, an oligonucleotide consists of 7 to 11 linked nucleosides. In certain embodiments, an oligonucleotide consists of 12 to 30 linked nucleosides. In certain embodiments, an oligonucleotide consists of 15 to 30 linked nucleosides. In certain embodiments, an oligonucleotide consists of 19 to 24 linked nucleosides. In certain embodiments, an oligonucleotide consists of 21 to 24 linked nucleosides.

In certain embodiments, an oligonucleotide consists of 7 linked nucleosides. In certain embodiments, an oligonucleotide consists of 8 linked nucleosides. In certain embodiments, an oligonucleotide consists of 9 linked nucleosides. In certain embodiments, an oligonucleotide consists of 10 linked nucleosides. In certain embodiments, an oligonucleotide consists of 11 linked nucleosides. In certain embodiments, an oligonucleotide consists of 12 linked nucleosides. In certain embodiments, an oligonucleotide consists of 13 linked nucleosides. In certain embodiments, an oligonucleotide consists of 14 linked nucleosides. In certain embodiments, an oligonucleotide consists of 15 linked nucleosides. In certain embodiments, an oligonucleotide consists of 16 linked nucleosides. In certain embodiments, an oligonucleotide consists of 17 linked nucleosides. In certain embodiments, an oligonucleotide consists of 18 linked nucleosides. In certain embodiments, an oligonucleotide consists of 19 linked nucleosides. In certain embodiments, an oligonucleotide consists of 20 linked nucleosides. In certain embodiments, an oligonucleotide consists of 21 linked nucleosides. In certain embodiments, an oligonucleotide consists of 22 linked nucleosides. In certain embodiments, an oligonucleotide consists of 23 linked nucleosides. In certain embodiments, an oligonucleotide consists of 24 linked nucleosides. In certain embodiments, an oligonucleotide consists of 25 linked nucleosides. In certain embodiments, an oligonucleotide consists of 26 linked nucleosides. In certain embodiments, an oligonucleotide consists of 27 linked nucleosides. In certain embodiments, an oligonucleotide consists of 28 linked nucleosides. In certain embodiments, an oligonucleotide consists of 29 linked nucleosides. In certain embodiments, an oligonucleotide consists of 30 linked nucleosides.

Certain Modifications

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain embodiments, the bicyclic sugar moiety is a D sugar in the alpha configuration. In certain embodiments, the bicyclic sugar moiety is a D sugar in the beta configuration. In certain embodiments, the bicyclic sugar moiety is an L sugar in the alpha configuration. In certain embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—($CH_2$)$_p$—, —O—$CH_2$—, —O—$CH_2CH_2$—, —O—CH(alkyl)-, —NH—($CH_2$)$_p$—, —N(alkyl)-($CH_2$)$_p$—, —O—CH(alkyl)-, —(CH(alkyl))—($CH_2$)$_p$—, —NH—O—($CH_2$)$_p$—, —N(alkyl)—($CH_2$)$_p$—, or —O—N(alkyl)-($CH_2$)$_p$—, wherein p is 1, 2, 3, 4 or 5 and each alkyl group can be further substituted. In certain embodiments, p is 1, 2 or 3. In certain embodiments, a bicyclic sugar moiety is —O—($CH_2$)), also known as 'locked nucleic acid' or 'LNA.'

In certain embodiments, a 2'-modified nucleoside comprises a 2'-substituent group selected from halo, allyl, amino, azido, SH, CN, OCN, $CF_3$, $OCF_3$, O—, S—, or N($R_m$)-alkyl; O—, S—, or N($R_m$)-alkenyl; O—, S— or N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, O($CH_2$)$_3$$NH_2$, $CH_2$—CH=$CH_2$, O—$CH_2$—CH=$CH_2$, $OCH_2CH_2OCH_3$, O($CH_2$)$_2$$SCH_3$, O—($CH_2$)$_2$—O—N($R_m$)($R_n$), —O($CH_2$)$_2$—O—($CH_2$)$_2$N($CH_3$)$_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'—O($CH_2$)$_2$$SCH_3$, O—($CH_2$)$_2$—O—N($CH_3$)$_2$, —O($CH_2$)$_2$—O—($CH_2$)$_2$N($CH_3$)$_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—($CH_2$)$_2$—$OCH_3$, and 2'-F.

In certain embodiments, a modified oligonucleotide comprises one or more internucleoside modifications. In certain such embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages.

In certain such embodiments, an internucleoside linkage has an amide backbone. In certain such embodiments, an internucleoside linkage has mixed N, O, S and $CH_2$ component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleoside comprises the same internucleoside linkage modifications throughout. In certain such embodiments, each internucleoside linkage of a uniformly modified oligonucleotide is a phosphorothioate internucleoside linkage.

In certain embodiments, a positionally modified oligonucleotide comprises regions of linked nucleosides, where each nucleoside of each region comprises the same sugar moiety, and where each nucleoside of each region comprises a sugar moiety different from that of an adjacent region.

In certain embodiments, a positionally modified oligonucleotide comprises at least 10 2'-fluoro modified nucleosides. Such a positionally modified oligonucleotide may be represented by the following formula I:

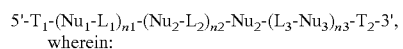
wherein:

each $Nu_1$ and $Nu_3$ is, independently, a stabilizing nucleoside;

at least 10 $Nu_2$ are 2'-fluoro nucleosides;

each $L_1$, $L_2$ and $L_3$ is, independently, an internucleoside linkage;

each $T_1$ and $T_2$ is, independently, H, a hydroxyl protecting group, an optionally linked conjugate group or a capping group;

$n_1$ is from 0 to about 3;

$n_2$ is from about 14 to about 22;

$n_3$ is from 0 to about 3; and provided that if $n_1$ is 0 then $T_1$ is not H or a hydroxyl protecting group, and if $n_3$ is 0, then $T_2$ is not H or a hydroxyl protecting group.

In certain such embodiments, $n_1$ and $n_3$ are each, independently, from 1 to about 3. In certain embodiments, $n_1$ and $n_3$ are each, independently, from 2 to about 3. In certain embodiments, $n_1$ is 1 or 2 and $n_3$ is 2 or 3. In certain embodiments, $n_1$ and $n_3$ are each 2. In certain embodiments, at least one of $n_1$ and $n_3$ is greater than zero. In certain embodiments, $n_1$ and $n_3$ is each greater than zero. In certain embodiments, one of $n_1$ and $n_3$ is greater than zero. In certain embodiments, one of $n_1$ and $n_3$ is greater than one.

In certain embodiments, $n_2$ is from 16 to 20. In certain embodiments, $n_2$ is from 17 to 19. In certain embodiments, $n_2$ is 18. In certain embodiments, $n_2$ is 19. In certain embodiments, $n_2$ is 20.

In certain embodiments, about 2 to about 8 of the $Nu_2$ nucleosides are stabilizing nucleosides. In certain embodiments, from about 2 to about 6 of the $Nu_2$ nucleosides are stabilizing nucleosides. In certain embodiments, from about 3 to about 4 of the $Nu_2$ nucleosides are stabilizing nucleosides. In certain embodiments, 3 of the $Nu_2$ nucleosides are stabilizing nucleosides.

In certain embodiments, each of the $Nu_2$ stabilizing nucleosides is separated from the $Nu_3$ stabilizing nucleosides by from 2 to about 8 2'-fluoro nucleosides. In certain embodiments each of the $Nu_2$ stabilizing nucleosides is separated from the $Nu_3$ stabilizing nucleosides by from 3 to about 8

2'-fluoro nucleosides. In certain embodiments each of the $Nu_2$ stabilizing nucleosides is separated from the $Nu_3$ stabilizing nucleosides by from 5 to about 8 2'-fluoro nucleosides.

In certain embodiments, a modified oligonucleotide comprises from 2 to about 6 $Nu_2$ stabilizing nucleosides. In certain embodiments, a modified oligonucleotide comprises 3 $Nu_2$ stabilizing nucleosides.

In certain embodiments, each of the $Nu_2$ stabilizing nucleosides is linked together in one contiguous sequence. In certain embodiments, at least two of the $Nu_2$ stabilizing nucleosides are separated by at least one of the 2'-fluoro nucleosides. In certain embodiments, each of the $Nu_2$ stabilizing nucleosides is separated by at least one of the 2'-fluoro nucleosides.

In certain embodiments, at least two contiguous sequences of the $Nu_2$ 2'-fluoro nucleosides are separated by at least one of the stabilizing nucleosides wherein each of the contiguous sequences have the same number of 2'-fluoro nucleosides.

In certain embodiments, $T_1$ and $T_2$ are each, independently, H or a hydroxyl protecting group. In certain embodiments, at least one of $T_1$ and $T_2$ is 4,4'-dimethoxytrityl. In certain embodiments, at least one of $T_1$ and $T_2$ is an optionally linked conjugate group. In certain embodiments, at least one of $T_1$ and $T_2$ is a capping group. In certain embodiments, the capping group is an inverted deoxy abasic group.

In certain embodiments, a positionally modified oligonucleotide comprises at least one modified internucleoside linkage. In certain such embodiments, each internucleoside linkage of a positionally modified oligonucleoside is a modified internucleoside linkage. In certain embodiments, at least one internucleoside linkage of a positionally modified oligonucleotide is a phosphorothioate internucleoside linkage. In certain such embodiments, each internucleoside linkage of a positionally modified oligonucleotide is a phosphorothioate internucleoside linkage.

In certain embodiments, a positionally modified motif is represented by the following formula II, which represents a modified oligonucleotide consisting of linked nucleosides:

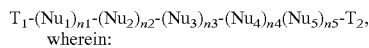
wherein:

$Nu_1$ and $Nu_5$ are, independently, 2' stabilizing nucleosides;
$Nu_2$ and $Nu_4$ are 2'-fluoro nucleosides;
$Nu_3$ is a 2'-modified nucleoside;
each of $n_1$ and $n_5$ is, independently, from 0 to 3;
the sum of $n_2$ plus $n_4$ is between 10 and 25;
$n_3$ is from 0 and 5; and
each $T_1$ and $T_2$ is, independently, H, a hydroxyl protecting group, an optionally linked conjugate group or a capping group.

In certain embodiments, the sum of $n_2$ and $n_4$ is 16. In certain embodiments, the sum of $n_2$ and $n_4$ is 17. In certain embodiments, the sum of $n_2$ and $n_4$ is 18. In certain embodiments, $n_1$ is 2; $n_3$ is 2 or 3; and $n_5$ is 2.

In certain embodiments, $Nu_1$ and $Nu_5$ are, independently, 2'-modified nucleosides. In certain embodiments, each internucleoside linkage is a modified internucleoside linkage. In certain such embodiments, each internucleoside is a phosphorothioate linkage.

In certain embodiments, a nucleoside comprises a modified nucleobase. In certain embodiments, where a 2'-O-methoxyethyl nucleoside comprises cytosine, the cytosine is a 5-methylcytosine.

In certain embodiments, $Nu_1$ is $O-(CH_2)_2-OCH_3$, $Nu_3$ is $O-(CH_2)_2-OCH_3$, and $Nu_5$ $O-(CH_2)_2-OCH_3$.

In certain embodiments, $Nu_1$ is $O-(CH_2)_2-OCH_3$, $Nu_3$ is $O-(CH_2)_2-OCH_3$, $Nu_5$ $O-(CH_2)_2-OCH_3$, $T_1$ is H and $T_2$ is H.

In certain embodiments, the sum of $n_2$ and $n_4$ is 13. In certain embodiments, the sum of $n_2$ and $n_4$ is 14. In certain embodiments, the sum of $n_2$ and $n_4$ is 15. In certain embodiments, the sum of $n_2$ and $n_4$ is 16. In certain embodiments, the sum of $n_2$ and $n_4$ is 17. In certain embodiments, the sum of $n_2$ and $n_4$ is 18.

In certain embodiments, $n_1$, $n_2$, and $n_3$ are each, independently, from 1 to 3. In certain embodiments, $n_1$, $n_2$, and $n_3$ are each, independently, from 2 to 3. In certain embodiments, $n_1$ is 1 or 2; $n_2$ is 2 or 3; and $n_3$ is 1 or 2. In certain embodiments, $n_1$ is 2; $n_3$ is 2 or 3; and $n_5$ is 2. In certain embodiments, $n_1$ is 2; $n_3$ is 3; and $n_5$ is 2. In certain embodiments, $n_1$ is 2; $n_3$ is 2; and $n_5$ is 2.

In certain embodiments, a modified oligonucleotide consists of 20 linked nucleosides. In certain such embodiments, the sum of $n_2$ and $n_4$ is 13; $n_1$ is 2; $n_3$ is 3; and $n_5$ is 2. In certain such embodiments, the sum of $n_2$ and $n_4$ is 14; $n_1$ is 2; $n_3$ is 2; and $n_5$ is 2.

In certain embodiments, a modified oligonucleotide consists of 21 linked nucleosides. In certain such embodiments, the sum of $n_2$ and $n_4$ is 14; $n_1$ is 2; $n_3$ is 3; and $n_5$ is 2. In certain such embodiments, the sum of $n_2$ and $n_4$ is 15; $n_1$ is 2; $n_3$ is 2; and $n_5$ is 2.

In certain embodiments, a modified oligonucleotide consists of 22 linked nucleosides. In certain such embodiments, the sum of $n_2$ and $n_4$ is 15; $n_1$ is 2; $n_3$ is 3; and $n_5$ is 2. In certain such embodiments, the sum of $n_2$ and $n_4$ is 16; $n_1$ is 2; $n_3$ is 2; and $n_5$ is 2.

In certain embodiments, a modified oligonucleotide consists of 23 linked nucleosides. In certain such embodiments, the sum of $n_2$ and $n_4$ is 16; $n_1$ is 2; $n_3$ is 3; and $n_5$ is 2. In certain such embodiments, the sum of $n_2$ and $n_4$ is 17; $n_1$ is 2; $n_3$ is 2; and $n_5$ is 2.

In certain embodiments, a modified oligonucleotide consists of 24 linked nucleosides. In certain such embodiments, the sum of $n_2$ and $n_4$ is 17; $n_1$ is 2; $n_3$ is 3; and $n_5$ is 2. In certain such embodiments, the sum of $n_2$ and $n_4$ is 18; $n_1$ is 2; $n_3$ is 2; and $n_5$ is 2.

In certain embodiments, a modified oligonucleotide consists of 23 linked nucleosides; $n_1$ is 2; $n_2$ is 10; $n_3$ is 3; $n_4$ is 6; $n_5$ is 2; $Nu_1$ is $O-(CH_2)_2-OCH_3$; $Nu_3$ is $O-(CH_2)_2-OCH_3$; and $Nu_5$ $O-(CH_2)_2-OCH_3$.

In certain embodiments, a modified oligonucleotide consists of 23 linked nucleosides; $n_1$ is 2; $n_2$ is 10; $n_3$ is 3; $n_4$ is 6; $n_5$ is 2; $Nu_1$ is $O-(CH_2)_2-OCH_3$; $Nu_3$ is $O-(CH_2)_2-OCH_3$; and $Nu_5$ $O-(CH_2)_2-OCH_3$; and each internucleoside linkage is a phosphorothioate linkage.

In certain embodiments, a modified oligonucleotide consists of 23 linked nucleosides; has the nucleobase sequence of SEQ ID NO: 6; $n_1$ is 2; $n_2$ is 10; $n_3$ is 3; $n_4$ is 6; $n_5$ is 2; $Nu_1$ is $O-(CH_2)_2-OCH_3$; $Nu_3$ is $O-(CH_2)_2-OCH_3$; $Nu_5$ $O-(CH_2)$; each internucleoside linkage is a phosphorothioate linkage; the cytosine at nucleobase 2 is a 5-methylcytosine; the cytosine at position 14 is a 5-methylcytosine; and the cytosine at nucleobase 22 is a 5-methylcytosine.

In certain embodiments, a modified oligonucleotide consists of 23 linked nucleosides; has the nucleobase sequence of SEQ ID NO: 7; $n_1$ is 2; $n_2$ is 10; $n_3$ is 3; $n_4$ is 6; $n_5$ is 2; $Nu_1$ is $O-(CH_2)_2-OCH_3$; $Nu_3$ is $O-(CH_2)_2-OCH_3$; $Nu_5$ $O-(CH_2)$; each internucleoside linkage is a phosphorothioate linkage; the cytosine at nucleobase 2 is a 5-methylcytosine; the cytosine at position 14 is a 5-methylcytosine; and the cytosine at nucleobase 22 is a 5-methylcytosine.

In certain embodiments, a modified oligonucleotide consists of 21 linked nucleosides; has the nucleobase sequence of SEQ ID NO: 8; $n_1$ is 2; $n_2$ is 8; $n_3$ is 3; $n_4$ is 6; $n_5$ is 2; $Nu_1$ is O—(CH$_2$)$_2$—OCH$_3$; $Nu_3$ is O—(CH$_2$)$_2$—OCH$_3$; $Nu_5$ O—(CH$_2$); each internucleoside linkage is a phosphorothioate linkage; the cytosine at nucleobase 2 is a 5-methylcytosine; and the cytosine at position 14 is a 5-methylcytosine.

In certain embodiments, a modified oligonucleotide complementary to a miRNA and consisting of 21 linked nucleosides has a Formula II selected from Table 2, where each internucleoside linkage is a phosphorothioate internucleoside linkage. In certain embodiments, a modified oligonucleotide having a Formula II selected from Table 2 has the nucleobase sequence of SEQ ID NO: 8.

TABLE 2

| SEQ ID NO | $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|---|
| 8 | 2 | 17 | 0 | 0 | 2 | 2'-MOE | 2'-MOE | 2'-MOE | H | H |
| 8 | 2 | 2 | 2 | 13 | 2 | 2'-MOE | 2'-MOE | 2'-MOE | H | H |
| 8 | 2 | 3 | 2 | 12 | 2 | 2'-MOE | 2'-MOE | 2'-MOE | H | H |
| 8 | 2 | 4 | 2 | 11 | 2 | 2'-MOE | 2'-MOE | 2'-MOE | H | H |
| 8 | 2 | 5 | 2 | 10 | 2 | 2'-MOE | 2'-MOE | 2'-MOE | H | H |
| 8 | 2 | 6 | 2 | 9 | 2 | 2'-MOE | 2'-MOE | 2'-MOE | H | H |
| 8 | 2 | 7 | 2 | 8 | 2 | 2'-MOE | 2'-MOE | 2'-MOE | H | H |
| 8 | 2 | 8 | 2 | 7 | 2 | 2'-MOE | 2'-MOE | 2'-MOE | H | H |
| 8 | 2 | 9 | 2 | 6 | 2 | 2'-MOE | 2'-MOE | 2'-MOE | H | H |
| 8 | 2 | 10 | 2 | 5 | 2 | 2'-MOE | 2'-MOE | 2'-MOE | H | H |
| 8 | 2 | 11 | 2 | 4 | 2 | 2'-MOE | 2'-MOE | 2'-MOE | H | H |
| 8 | 2 | 12 | 2 | 3 | 2 | 2'-MOE | 2'-MOE | 2'-MOE | H | H |
| 8 | 2 | 13 | 2 | 2 | 2 | 2'-MOE | 2'-MOE | 2'-MOE | H | H |
| 8 | 2 | 2 | 3 | 12 | 2 | 2'-MOE | 2'-MOE | 2'-MOE | H | H |
| 8 | 2 | 3 | 3 | 11 | 2 | 2'-MOE | 2'-MOE | 2'-MOE | H | H |
| 8 | 2 | 4 | 3 | 10 | 2 | 2'-MOE | 2'-MOE | 2'-MOE | H | H |
| 8 | 2 | 5 | 3 | 9 | 2 | 2'-MOE | 2'-MOE | 2'-MOE | H | H |
| 8 | 2 | 6 | 3 | 8 | 2 | 2'-MOE | 2'-MOE | 2'-MOE | H | H |
| 8 | 2 | 7 | 3 | 7 | 2 | 2'-MOE | 2'-MOE | 2'-MOE | H | H |
| 8 | 2 | 8 | 3 | 6 | 2 | 2'-MOE | 2'-MOE | 2'-MOE | H | H |
| 8 | 2 | 9 | 3 | 5 | 2 | 2'-MOE | 2'-MOE | 2'-MOE | H | H |
| 8 | 2 | 10 | 3 | 4 | 2 | 2'-MOE | 2'-MOE | 2'-MOE | H | H |
| 8 | 2 | 11 | 3 | 3 | 2 | 2'-MOE | 2'-MOE | 2'-MOE | H | H |
| 8 | 2 | 12 | 3 | 2 | 2 | 2'-MOE | 2'-MOE | 2'-MOE | H | H |
| 8 | 2 | 8 | 6 | 3 | 2 | 2'-MOE | 2'-MOE | 2'-MOE | H | H |

In certain embodiments, a modified oligonucleotide complementary to a miRNA and consisting of 22 linked nucleosides has a Formula II selected from Table 3, where each internucleoside linkage is a phosphorothioate internucleoside linkage. In certain embodiments, a modified oligonucleotide having a Formula II selected from Table 3 comprises 22 linked nucleosides of SEQ ID NO: 6, 7, or 8.

TABLE 3

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 18 | 0 | 0 | 2 | 2'-MOE | 2'-MOE | 2'-MOE | H | H |
| 2 | 2 | 2 | 14 | 2 | 2'-MOE | 2'-MOE | 2'-MOE | H | H |
| 2 | 3 | 2 | 13 | 2 | 2'-MOE | 2'-MOE | 2'-MOE | H | H |
| 2 | 4 | 2 | 12 | 2 | 2'-MOE | 2'-MOE | 2'-MOE | H | H |
| 2 | 5 | 2 | 11 | 2 | 2'-MOE | 2'-MOE | 2'-MOE | H | H |
| 2 | 6 | 2 | 10 | 2 | 2'-MOE | 2'-MOE | 2'-MOE | H | H |
| 2 | 7 | 2 | 9 | 2 | 2'-MOE | 2'-MOE | 2'-MOE | H | H |
| 2 | 8 | 2 | 8 | 2 | 2'-MOE | 2'-MOE | 2'-MOE | H | H |
| 2 | 9 | 2 | 7 | 2 | 2'-MOE | 2'-MOE | 2'-MOE | H | H |
| 2 | 10 | 2 | 6 | 2 | 2'-MOE | 2'-MOE | 2'-MOE | H | H |
| 2 | 11 | 2 | 5 | 2 | 2'-MOE | 2'-MOE | 2'-MOE | H | H |
| 2 | 12 | 2 | 4 | 2 | 2'-MOE | 2'-MOE | 2'-MOE | H | H |
| 2 | 13 | 2 | 3 | 2 | 2'-MOE | 2'-MOE | 2'-MOE | H | H |
| 2 | 14 | 2 | 2 | 2 | 2'-MOE | 2'-MOE | 2'-MOE | H | H |
| 2 | 2 | 3 | 13 | 2 | 2'-MOE | 2'-MOE | 2'-MOE | H | H |
| 2 | 3 | 3 | 12 | 2 | 2'-MOE | 2'-MOE | 2'-MOE | H | H |
| 2 | 4 | 3 | 11 | 2 | 2'-MOE | 2'-MOE | 2'-MOE | H | H |

TABLE 3-continued

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 5 | 3 | 10 | 2 | 2'-MOE | 2'-MOE | 2'-MOE | H | H |
| 2 | 6 | 3 | 9 | 2 | 2'-MOE | 2'-MOE | 2'-MOE | H | H |
| 2 | 7 | 3 | 8 | 2 | 2'-MOE | 2'-MOE | 2'-MOE | H | H |
| 2 | 8 | 3 | 7 | 2 | 2'-MOE | 2'-MOE | 2'-MOE | H | H |
| 2 | 9 | 3 | 6 | 2 | 2'-MOE | 2'-MOE | 2'-MOE | H | H |
| 2 | 10 | 3 | 5 | 2 | 2'-MOE | 2'-MOE | 2'-MOE | H | H |
| 2 | 11 | 3 | 4 | 2 | 2'-MOE | 2'-MOE | 2'-MOE | H | H |
| 2 | 12 | 3 | 3 | 2 | 2'-MOE | 2'-MOE | 2'-MOE | H | H |
| 2 | 13 | 3 | 2 | 2 | 2'-MOE | 2'-MOE | 2'-MOE | H | H |
| 2 | 8 | 6 | 4 | 2 | 2'-MOE | 2'-MOE | 2'-MOE | H | H |

In certain embodiments, a modified oligonucleotide complementary to a miRNA and consisting of 23 linked nucleosides has a Formula II selected from Table 4, where each internucleoside linkage is a phosphorothioate internucleoside linkage. In certain embodiments, a modified oligonucleotide having a Formula II selected from Table 4 comprises a nucleobase sequence selected SEQ ID NO: 6, 7, or 8.

TABLE 4

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 19 | 0 | 0 | 2 | 2'-MOE | 2'-MOE | 2'-MOE | H | H |
| 2 | 2 | 2 | 15 | 2 | 2'-MOE | 2'-MOE | 2'-MOE | H | H |
| 2 | 3 | 2 | 14 | 2 | 2'-MOE | 2'-MOE | 2'-MOE | H | H |
| 2 | 4 | 2 | 13 | 2 | 2'-MOE | 2'-MOE | 2'-MOE | H | H |
| 2 | 5 | 2 | 12 | 2 | 2'-MOE | 2'-MOE | 2'-MOE | H | H |
| 2 | 6 | 2 | 11 | 2 | 2'-MOE | 2'-MOE | 2'-MOE | H | H |
| 2 | 7 | 2 | 10 | 2 | 2'-MOE | 2'-MOE | 2'-MOE | H | H |
| 2 | 8 | 2 | 9 | 2 | 2'-MOE | 2'-MOE | 2'-MOE | H | H |
| 2 | 9 | 2 | 8 | 2 | 2'-MOE | 2'-MOE | 2'-MOE | H | H |
| 2 | 10 | 2 | 7 | 2 | 2'-MOE | 2'-MOE | 2'-MOE | H | H |
| 2 | 11 | 2 | 6 | 2 | 2'-MOE | 2'-MOE | 2'-MOE | H | H |
| 2 | 12 | 2 | 5 | 2 | 2'-MOE | 2'-MOE | 2'-MOE | H | H |
| 2 | 13 | 2 | 4 | 2 | 2'-MOE | 2'-MOE | 2'-MOE | H | H |
| 2 | 14 | 2 | 3 | 2 | 2'-MOE | 2'-MOE | 2'-MOE | H | H |
| 2 | 15 | 2 | 2 | 2 | 2'-MOE | 2'-MOE | 2'-MOE | H | H |
| 2 | 2 | 3 | 14 | 2 | 2'-MOE | 2'-MOE | 2'-MOE | H | H |
| 2 | 3 | 3 | 13 | 2 | 2'-MOE | 2'-MOE | 2'-MOE | H | H |
| 2 | 4 | 3 | 12 | 2 | 2'-MOE | 2'-MOE | 2'-MOE | H | H |
| 2 | 5 | 3 | 11 | 2 | 2'-MOE | 2'-MOE | 2'-MOE | H | H |
| 2 | 6 | 3 | 10 | 2 | 2'-MOE | 2'-MOE | 2'-MOE | H | H |
| 2 | 7 | 3 | 9 | 2 | 2'-MOE | 2'-MOE | 2'-MOE | H | H |
| 2 | 8 | 3 | 8 | 2 | 2'-MOE | 2'-MOE | 2'-MOE | H | H |
| 2 | 9 | 3 | 7 | 2 | 2'-MOE | 2'-MOE | 2'-MOE | H | H |
| 2 | 10 | 3 | 6 | 2 | 2'-MOE | 2'-MOE | 2'-MOE | H | H |
| 2 | 11 | 3 | 5 | 2 | 2'-MOE | 2'-MOE | 2'-MOE | H | H |
| 2 | 12 | 3 | 4 | 2 | 2'-MOE | 2'-MOE | 2'-MOE | H | H |
| 2 | 13 | 3 | 3 | 2 | 2'-MOE | 2'-MOE | 2'-MOE | H | H |
| 2 | 14 | 3 | 2 | 2 | 2'-MOE | 2'-MOE | 2'-MOE | H | H |
| 2 | 8 | 6 | 5 | 2 | 2'-MOE | 2'-MOE | 2'-MOE | H | H |

In certain embodiments, a modified oligonucleotide complementary to a miRNA and consisting of 24 linked nucleosides has a Formula II selected from Table 5, where each internucleoside linkage is a phosphorothioate internucleoside linkage. In certain embodiments, a modified oligonucleotide having a Formula II selected from Table 5 comprises a nucleobase sequence of SEQ ID NO: 6, 7, or 8.

TABLE 5

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 20 | 0 | 0 | 2 | 2'-MOE | 2'-MOE | 2'-MOE | H | H |
| 2 | 2 | 2 | 16 | 2 | 2'-MOE | 2'-MOE | 2'-MOE | H | H |
| 2 | 3 | 2 | 15 | 2 | 2'-MOE | 2'-MOE | 2'-MOE | H | H |
| 2 | 4 | 2 | 14 | 2 | 2'-MOE | 2'-MOE | 2'-MOE | H | H |
| 2 | 5 | 2 | 13 | 2 | 2'-MOE | 2'-MOE | 2'-MOE | H | H |
| 2 | 6 | 2 | 12 | 2 | 2'-MOE | 2'-MOE | 2'-MOE | H | H |
| 2 | 7 | 2 | 11 | 2 | 2'-MOE | 2'-MOE | 2'-MOE | H | H |

TABLE 5-continued

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 8 | 2 | 10 | 2 | 2'-MOE | 2'-MOE | 2'-MOE | H | H |
| 2 | 9 | 2 | 9 | 2 | 2'-MOE | 2'-MOE | 2'-MOE | H | H |
| 2 | 10 | 2 | 8 | 2 | 2'-MOE | 2'-MOE | 2'-MOE | H | H |
| 2 | 11 | 2 | 7 | 2 | 2'-MOE | 2'-MOE | 2'-MOE | H | H |
| 2 | 12 | 2 | 6 | 2 | 2'-MOE | 2'-MOE | 2'-MOE | H | H |
| 2 | 13 | 2 | 5 | 2 | 2'-MOE | 2'-MOE | 2'-MOE | H | H |
| 2 | 14 | 2 | 4 | 2 | 2'-MOE | 2'-MOE | 2'-MOE | H | H |
| 2 | 15 | 2 | 3 | 2 | 2'-MOE | 2'-MOE | 2'-MOE | H | H |
| 2 | 16 | 2 | 2 | 2 | 2'-MOE | 2'-MOE | 2'-MOE | H | H |
| 2 | 2 | 3 | 15 | 2 | 2'-MOE | 2'-MOE | 2'-MOE | H | H |
| 2 | 3 | 3 | 14 | 2 | 2'-MOE | 2'-MOE | 2'-MOE | H | H |
| 2 | 4 | 3 | 13 | 2 | 2'-MOE | 2'-MOE | 2'-MOE | H | H |
| 2 | 5 | 3 | 12 | 2 | 2'-MOE | 2'-MOE | 2'-MOE | H | H |
| 2 | 6 | 3 | 11 | 2 | 2'-MOE | 2'-MOE | 2'-MOE | H | H |
| 2 | 7 | 3 | 10 | 2 | 2'-MOE | 2'-MOE | 2'-MOE | H | H |
| 2 | 8 | 3 | 9 | 2 | 2'-MOE | 2'-MOE | 2'-MOE | H | H |
| 2 | 9 | 3 | 8 | 2 | 2'-MOE | 2'-MOE | 2'-MOE | H | H |
| 2 | 10 | 3 | 7 | 2 | 2'-MOE | 2'-MOE | 2'-MOE | H | H |
| 2 | 11 | 3 | 6 | 2 | 2'-MOE | 2'-MOE | 2'-MOE | H | H |
| 2 | 12 | 3 | 5 | 2 | 2'-MOE | 2'-MOE | 2'-MOE | H | H |
| 2 | 13 | 3 | 4 | 2 | 2'-MOE | 2'-MOE | 2'-MOE | H | H |
| 2 | 14 | 3 | 3 | 2 | 2'-MOE | 2'-MOE | 2'-MOE | H | H |
| 2 | 15 | 3 | 2 | 2 | 2'-MOE | 2'-MOE | 2'-MOE | H | H |
| 2 | 8 | 6 | 6 | 2 | 2'-MOE | 2'-MOE | 2'-MOE | H | H |

In certain embodiments, a modified oligonucleotide complementary to a miRNA and consisting of 25 linked nucleosides has a Formula II selected from Table 6, where each internucleoside linkage is a phosphorothioate internucleoside linkage. In certain embodiments, a modified oligonucleotide having a Formula II selected from Table 6 comprises a nucleobase sequence of SEQ ID NO: 6, 7, or 8.

TABLE 6

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 21 | 0 | 0 | 2 | 2'-MOE | 2'-MOE | 2'-MOE | H | H |
| 2 | 2 | 2 | 17 | 2 | 2'-MOE | 2'-MOE | 2'-MOE | H | H |
| 2 | 3 | 2 | 16 | 2 | 2'-MOE | 2'-MOE | 2'-MOE | H | H |
| 2 | 4 | 2 | 15 | 2 | 2'-MOE | 2'-MOE | 2'-MOE | H | H |
| 2 | 5 | 2 | 14 | 2 | 2'-MOE | 2'-MOE | 2'-MOE | H | H |
| 2 | 6 | 2 | 13 | 2 | 2'-MOE | 2'-MOE | 2'-MOE | H | H |
| 2 | 7 | 2 | 12 | 2 | 2'-MOE | 2'-MOE | 2'-MOE | H | H |
| 2 | 8 | 2 | 11 | 2 | 2'-MOE | 2'-MOE | 2'-MOE | H | H |
| 2 | 9 | 2 | 10 | 2 | 2'-MOE | 2'-MOE | 2'-MOE | H | H |
| 2 | 10 | 2 | 9 | 2 | 2'-MOE | 2'-MOE | 2'-MOE | H | H |
| 2 | 11 | 2 | 8 | 2 | 2'-MOE | 2'-MOE | 2'-MOE | H | H |
| 2 | 12 | 2 | 7 | 2 | 2'-MOE | 2'-MOE | 2'-MOE | H | H |
| 2 | 13 | 2 | 6 | 2 | 2'-MOE | 2'-MOE | 2'-MOE | H | H |
| 2 | 14 | 2 | 5 | 2 | 2'-MOE | 2'-MOE | 2'-MOE | H | H |
| 2 | 15 | 2 | 4 | 2 | 2'-MOE | 2'-MOE | 2'-MOE | H | H |
| 2 | 16 | 2 | 3 | 2 | 2'-MOE | 2'-MOE | 2'-MOE | H | H |
| 2 | 17 | 2 | 2 | 2 | 2'-MOE | 2'-MOE | 2'-MOE | H | H |
| 2 | 2 | 3 | 16 | 2 | 2'-MOE | 2'-MOE | 2'-MOE | H | H |
| 2 | 3 | 3 | 15 | 2 | 2'-MOE | 2'-MOE | 2'-MOE | H | H |
| 2 | 4 | 3 | 14 | 2 | 2'-MOE | 2'-MOE | 2'-MOE | H | H |
| 2 | 5 | 3 | 13 | 2 | 2'-MOE | 2'-MOE | 2'-MOE | H | H |
| 2 | 6 | 3 | 12 | 2 | 2'-MOE | 2'-MOE | 2'-MOE | H | H |
| 2 | 7 | 3 | 11 | 2 | 2'-MOE | 2'-MOE | 2'-MOE | H | H |
| 2 | 8 | 3 | 10 | 2 | 2'-MOE | 2'-MOE | 2'-MOE | H | H |
| 2 | 9 | 3 | 9 | 2 | 2'-MOE | 2'-MOE | 2'-MOE | H | H |
| 2 | 10 | 3 | 8 | 2 | 2'-MOE | 2'-MOE | 2'-MOE | H | H |
| 2 | 11 | 3 | 7 | 2 | 2'-MOE | 2'-MOE | 2'-MOE | H | H |
| 2 | 12 | 3 | 6 | 2 | 2'-MOE | 2'-MOE | 2'-MOE | H | H |
| 2 | 13 | 3 | 5 | 2 | 2'-MOE | 2'-MOE | 2'-MOE | H | H |
| 2 | 14 | 3 | 4 | 2 | 2'-MOE | 2'-MOE | 2'-MOE | H | H |
| 2 | 15 | 3 | 3 | 2 | 2'-MOE | 2'-MOE | 2'-MOE | H | H |
| 2 | 16 | 3 | 2 | 2 | 2'-MOE | 2'-MOE | 2'-MOE | H | H |
| 2 | 8 | 6 | 7 | 2 | 2'-MOE | 2'-MOE | 2'-MOE | H | H |

In certain embodiments, a compound is represented by the following formula III:

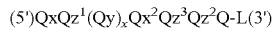

In certain embodiments, Q is a 2'-O-methyl modified nucleoside. In certain embodiments, x is phosphorothioate. In certain embodiments, y is phosphodiester. In certain embodiments, each of z1, z2, z3, and z4 is, independently phosphorothioate or phosphodiester. In certain embodiments, n is 6 to 17. In certain embodiments, L is cholesterol. In certain embodiments, n is 12 to 17.

In certain embodiments, x is

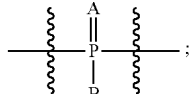

One of A and B is S while the other is O;

y is

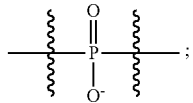 [SMILES: *P(*)(=O)[O-]]

Each of z1, z2, z3, and z4 is independently x or y;

n=6-17

L is

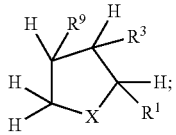

Wherein:

X is $N(CO)R^7$, or $NR^7$;

Each of $R^1$, $R^3$ and $R^9$, is independently, H, OH, or $-CH_2OR^b$ provided that at least one of $R^1$, $R^3$ and $R^9$ is OH and at least one of $R^1$, $R^3$ and $R^9$ is $-CH_2OR^b$;

$R^7$ is $R^d$ or $C_1$-$C_{20}$ alkyl substituted with $NR^cR^d$ or $NHC(O)R^d$;

$R^c$ is H or $C_1$-$C_6$ alkyl;

$R^d$ is a carbohydrate radical; or a steroid radical, which is optionally tethered to at least one carbohydrate radical; and $R^b$ is

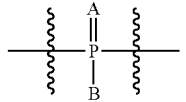

with one of A and B is S while the other is O.

In certain embodiments, Rd is cholesterol. In certain embodiments each of $z^1$, $z^2$, $z^3$, and $z^4$ is

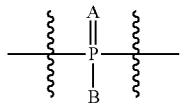

with one of A and B is S while the other is O.

In certain embodiments, $R^1$ is —$CH_2OR^b$. In certain embodiments, $R^9$ is OH. In certain embodiments, $R^1$ and $R^9$ are trans. In certain embodiments, $R^9$ is OH. In certain embodiments, $R^1$ and $R^3$ are trans. In certain embodiments, R3 is —$CH_2OR^b$. In certain embodiments, $R^1$ is OH. In certain embodiments, $R^1$ and $R^3$ are trans. In certain embodiments, $R^9$ is OH. In certain embodiments, $R^3$ and $R^9$ are trans. In certain embodiments, $R^9$ is $CH_2OR^b$. In certain embodiments, $R^1$ is OH. In certain embodiments, $R^1$ and $R^9$ are trans. In certain embodiments, X is $NC(O)R^7$. In certain embodiments, $R^7$ is —$CH_2(CH_2)_3CH_2NHC(O)R^d$.

In certain embodiments, a modified oligonucleotide having a positionally modified motif comprises LNA. In certain embodiments, a modified oligonucleotide has a motif selected from among one of the motifs listed below, wherein L=an LNA nucleoside, d=a DNA nucleoside, M=a 2'-MOE nucleoside, and F=a 2'-Fluoro nucleoside. In certain embodiments, nucleosides in parentheses are optionally included in the modified oligonucleotide, in other words, the motif encompasses modified oligonucleotides of varying lengths depending upon how many nucleosides in parentheses are included.

LdLddLLddLdLdLL
LdLdLLLddLLLdLL
LMLMMLLMMLMLMLL
LMLMLLLMMLLLMLL
LFLFFLLFFLFLFLL
LFLFLLLFFLLLFLL
LddLddLddL(d)(d)(L)(d)(d)(L)(d)
dLddLddLdd(L)(d)(d)(L)(d)(d)(L)
ddLddLddLd(d)(L)(d)(d)(L)(d)(d)
LMMLMMLMML(M)(M)(L)(M)(M)(L)(M)
MLMMLMMLMM(L)(M)(M)(L)(M)(M)(L)
MMLMMLMMLM(M)(L)(M)(M)(L)(M)(M)
LFFLFFLFFL(F)(F)(L)(F)(F)(L)(F)
FLFFLFFLFF(L)(F)(F)(L)(F)(F)(L)
FFLFFLFFLF(F)(L)(F)(F)(L)(F)(F)
dLdLdLdLdL(d)(L)(d)(L)(d)(L)(d)
LdLdLdLdLdL(d)(L)(d)(L)(d)(L)(d)(L)
MLMLMLMLML(M)(L)(M)(L)(M)(L)(M)
LMLMLMLMLM(L)(M)(L)(M)(L)(M)(L)
FLFLFLFLFL(F)(L)(F)(L)(F)(L)(F)
LFLFLFLFLF(L)(F)(L)(F)(L)(F)(L)

Additional motifs are disclosed in PCT Publication No. WO/2007/112754, which is herein incorporated by reference in its entirety for the description of oligonucleotide modifications and patterns of oligonucleotide modifications.

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the external regions is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2'-O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-O-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different that that of the other external region.

In certain embodiments, the external regions comprise, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiments, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

Certain Additional Therapies

Treatments for metabolic disorders may comprise more than one therapy. As such, in certain embodiments the present invention provides methods for treating metabolic disorders comprising administering to a subject in need thereof a compound comprising an oligonucleotide complementary to miR-103 and/or miR-107, or a precursor thereof, and further comprising administering at least one additional pharmaceutical agent.

In certain embodiments, the additional pharmaceutical agent is a glucose-lowering agent.

In certain embodiments, the glucose-lowering agent is a PPAR agonist (gamma, dual, or pan), a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, a meglitinide, a thiazolidinedione, or a sulfonylurea.

In certain embodiments, the glucose-lowering agent is a GLP-I analog. In certain embodiments, the GLP-I analog is exendin-4 or liraglutide.

In certain embodiments, the glucose-lowering agent is a sulfonylurea. In certain embodiments, the sulfonylurea is acetohexamide, chlorpropamide, tolbutamide, tolazamide, glimepiride, a glipizide, a glyburide, or a gliclazide.

In certain embodiments, the glucose-lowering agent is a biguanide. In certain embodiments, the biguanide is metformin. In certain embodiments, blood glucose levels are decreased without increased lactic acidosis as compared to the lactic acidosis observed after treatment with metformin alone.

In certain embodiments, the glucose-lowering agent is a meglitinide. In certain embodiments, the meglitinide is nateglinide or repaglinide.

In certain embodiments, the glucose-lowering agent is a thiazolidinedione. In certain embodiments, the thiazolidinedione is pioglitazone, rosiglitazone, or troglitazone. In certain embodiments, blood glucose levels are decreased without greater weight gain than observed with rosiglitazone treatment alone.

In certain embodiments, the glucose-lowering agent is an alpha-glucosidase inhibitor. In certain embodiments, the alpha-glucosidase inhibitor is acarbose or miglitol.

In certain embodiments, the glucose-lowering agent is an antisense oligonucleotide targeted to PTP1B.

In certain embodiments, an additional therapy is an anti-obesity agent. In certain embodiments, an anti-obesity agent is Orlistat, Sibutramine, or Rimonabant.

In a certain embodiment, the additional therapy is therapeutic lifestyle change. In certain embodiments, the therapeutic lifestyle change includes an exercise regimen and/or diet.

In certain embodiments the dose of an additional pharmaceutical agent is the same as the dose that would be administered if the additional pharmaceutical agent was administered alone.

In certain embodiments the dose of an additional pharmaceutical agent is lower than the dose that would be administered if the additional pharmaceutical agent was administered alone. In certain embodiments the dose of an additional pharmaceutical agent is greater than the dose that would be administered if the additional pharmaceutical agent was administered alone.

Further examples of additional pharmaceutical agents include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-I inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, an additional therapy is a lipid-lowering therapy. In certain such embodiments, a lipid-lowering therapy is therapeutic lifestyle change. In certain such embodiments, a lipid-lowering therapy is LDL apheresis.

Certain Pharmaceutical Compositions

Provided herein are pharmaceutical compositions comprising oligonucleotides. In certain embodiments, such pharmaceutical compositions are used for the treatment of metabolic disorders, and associated conditions. In certain embodiments, a pharmaceutical composition provided herein comprises a compound comprising an oligonucleotide consisting of 12 to 30 linked nucleosides and having a nucleobase sequence complementary to miR-103, miR-107, or a precursor thereof. In certain embodiments, a pharmaceutical composition provided herein comprises a compound consisting of an oligonucleotide consisting of 12 to 30 linked nucleosides and having a nucleobase sequence complementary to miR-103, miR-107, or a precursor thereof.

Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

In certain embodiments, a pharmaceutical composition is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of an oligonucleotide which has been prepared in water for injection, or in saline for injection, adjusted to pH 7.0-9.0 with acid or base during preparation, and then lyophilized. The lyophilized modified oligonucleotide may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety complexed with a nucleic acid. In certain embodiments, such preparations comprise one or more compounds each individually having a structure defined by formula (I) or a pharmaceutically acceptable salt thereof, formula (I)

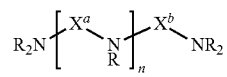

wherein each $X_a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (I) in the preparation are not H; m is 1, 2, 3 or 4; Y is O, $NR^2$, or S; R' is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tabletting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising an oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Kits

The present invention also provides kits. In some embodiments, the kits comprise one or more compounds of the invention comprising a modified oligonucleotide, wherein the nucleobase sequence of the oligonucleotide is complementary to miR-103 and/or 107. The compounds complementary to miR-103 and/or miR-107 can be any of the compounds described herein, and can have any of the modifications described herein. In some embodiments, the compounds complementary to miR-103 and/or miR-107 can be present within a vial. A plurality of vials, such as 10, can be present in, for example, dispensing packs. In some embodiments, the vial is manufactured so as to be accessible with a syringe. The kit can also contain instructions for using the compounds complementary to miR-103 and/or miR-107.

In some embodiments, the kits may be used for administration of the compound complementary to miR-103 and/or miR-107 to a subject. In such instances, in addition to compounds complementary to miR-103 and/or miR-107, the kit can further comprise one or more of the following: syringe, alcohol swab, cotton ball, and/or gauze pad. In some embodiments, the compounds complementary to miR-103 and/or miR-107 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds complementary to miR-103 and/or miR-107.

Certain Experimental Models

In certain embodiments, the present invention provides methods of using and/or testing modified oligonucleotides of the present invention in an experimental model. Those having skill in the art are able to select and modify the protocols for such experimental models to evaluate a pharmaceutical agent of the invention.

Generally, modified oligonucleotides are first tested in cultured cells. Suitable cell types include those that are related to the cell type to which delivery of an oligonucleotide is desired in vivo. For example, suitable cell types for the study of the methods described herein include primary hepatocytes, primary adipocytes, preadipocytes, differentiated adipocytes, HepG2 cells, Huh7 cells, 3T3L1 cells, and C2C12 cells (murine myoblasts).

In certain embodiments, the extent to which an oligonucleotide interferes with the activity of a miRNA is assessed in cultured cells. In certain embodiments, inhibition of miRNA activity may be assessed by measuring the levels of the miRNA. Alternatively, the level of a predicted or validated miRNA target may be measured. An inhibition of miRNA activity may result in the increase in the mRNA and/or protein of a miRNA target. Further, in certain embodiments, certain phenotypic outcomes may be measured. For example, suitable phenotypic outcomes include insuling signaling.

Suitable experimental animal models for the testing of the methods described herein include: ob/ob mice (a model for diabetes, obesity and insulin resistance), db/db mice (a model for diabetes, obesity and insulin resistance), high-fat fed C57B16/J mice, Zucker diabetic rats, and aP2-SREBP transgenic mice.

Certain Quantitation Assays

The effects of antisense inhibition of a miRNA following the administration of modified oligonucleotides may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, antisense inhibition of a miRNA is assessed by measuring the mRNA and/or protein level of a target of a miRNA. Antisense inhibition of a miRNA generally results in the increase in the level of mRNA and/or protein of a target of the miRNA.

The following examples are presented in order to more fully illustrate some embodiments of the invention. They should, in no way be construed, however, as limiting the broad scope of the invention.

Throughout the examples, unless otherwise indicated, statistical significance is indicated as follow: *=p<0.05; =p<0.01; *=p<0.001.

EXAMPLES

Example 1

Expression of microRNAs in Insulin Sensitive Tissues

To identify microRNAs involved in insulin signaling and response, insulin sensitive tissues were screened for microRNA expression. Microarray analysis was performed to identify microRNAs that are dysregulated in livers of ob/ob and high-fat diet induced obese (DIO) C57B16/J mice, both of which are animal models of obesity, insulin-resistance, and diabetes. The microRNAs miR-103 and miR-107, two conserved and ubiquitously expressed microRNAs (see FIG. 1E, F) were found to be upregulated in the liver in several of these models, including ob/ob mice and high-fat fed mice (DIO mice).

Northern blotting confirmed this result and demonstrated a 2 to 3-fold up-regulation in livers of both ob/ob and high fat fed induced obese mice (see FIG. 1A). Real-time PCR was used to distinguish miR-103 from miR-107, which differ by one base at position 21 (see Table 7 and FIG. 1B). Both miR-103 and miR-107 were up-regulated in livers of ob/ob and high fat fed induced obese mice (See Table 8).

TABLE 7

Distinguishing miR-103 from miR-107 by real-time PCR

|  | 0.5 nM Synthetic miR-107 | | 0.5 nM Synthetic miR-103 | |
| --- | --- | --- | --- | --- |
|  | + | − | − | + |
| Real time 107 level | 1 | No CT | No CT | 0.016 |
| Real time 103 level | 0.0002 | No CT | No CT | 1 |

TABLE 8

Upregulation of miR-103 and miR-107 in ob/ob and DIO livers

|  | wt | ob/ob | Normal chow fed | DIO |
| --- | --- | --- | --- | --- |
| Relative miR-103 expression value | 1 | 1.9194 | 1 | 2.272 |
| Relative miR-107 expression value | 1 | 2.1753 | 1 | 2.3992 |

MicroRNA expression was also analyzed in liver biopsies of healthy individuals, HBV- and HCV-infected individuals, and human patients with alcoholic steatohepatitis (ASH), non-alcoholic fatty liver disease (NAFLD), and non-alcoholic steatohepatitis (NASH). miR-103 and miR-107 were similar in normal subjects and HBV- and HCV-infected subjects. However, miR-103 and miR-107 levels were increased in liver samples of subjects with ASH, NAFLD, and NASH, conditions often associated with diabetes (See Table 9).

TABLE 9 miR-103 and miR-107 expression in liver samples of human subjects

|  | # Subjects | miR-103 Relative Expression Level | miR-107 Relative Expression Level |
| --- | --- | --- | --- |
| Control | 8 | 1.0222 | 1.1253 |
| HBV | 7 | 1.106 | 0.9555 |
| HCV | 7 | 0.9652 | 0.9565 |
| ASH | 7 | 1.516 | 1.2226 |
| NAFLD | 15 | 1.3033 | 1.3277 |
| NASH | 13 | 1.7141* | 1.628* |
| Control + HBV + HCV | 22 | 1.0307 | 1.0176 |
| ASH | 7 | 1.516** | 1.2226 |
| NAFLD | 15 | 1.3033** | 1.3277** |
| NASH | 13 | 1.7141* | 1.628* |

Example 2

Inhibition of miR-103 or miR-107 Alleviates Hyperglycemia in Animals

The inhibition of miR-103 or miR-107 may result in therapeutic benefits in subjects having diabetes or insulin resistance. Obese, insulin-resistant ob/ob mice are commonly used as a model for diabetes and obesity. Mice fed a high fat diet are used as a model of impaired glucose tolerance and Type 2 diabetes. Accordingly, the inhibition of miR-103 or miR-107 was assessed in ob/ob mice and DIO mice.

Unless otherwise specified, anti-miRs used are modified as follows:

anti-miR-103 having the sequence of SEQ ID NO: 6,2'-O-methyl modifications at each sugar, phosphorothioate modifications at each of the first 4 internucleoside linkages (at the 5' end), phosphorothioate modifications at each of the last 2 internucleosides linkages (at the 3' end), and a cholesterol linked to the 3' end through a hydroxyprolinol linkage anti-miR-107 having the sequence of SEQ ID NO: 7,2'-O-methyl modifications at each sugar, phosphorothioate modifications at each of the first 4 internucleoside linkages (at the 5' end), phosphorothioate modifications at each of the last 2 internucleosides linkages (at the 3' end), and a cholesterollinked to the 3' end through a hydroxyprolinol linkage.

Control anti-miR anti-mm-[107], having the nucleobase sequence TCATTGGCATGTACCATGCAGCT (SEQ ID NO: 9), 2'-O-methyl modifications at each sugar, phosphorothioate modifications at each of the first 4 internucleoside linkages, phosphorothioate modifications at each of the last 2 internucleoside linkages, and a cholesterol linked to the 3' end through a hydroxyprolinol linkage. As miR-103 and miR-107 differ by a single nucleotide, anti-mm-107 is mismatched with respect to both miR-103 (4 total mismatches) and miR-107 (5 total mismatches); and Control anti-miR anti-miR-124, having the nucleobase sequence of SEQ ID NO: 19; 2'-O-methyl modifications at each sugar, phosphorothioate modifications at each of the first 4 internucleoside linkages, phosphorothioate modifications at each of the last 2 internucleoside linkages, and a cholesterol linked to the 3' end through a hydroxyprolinol linkage.

Unless otherwise specified, wildtype mice were 6- to 8-week old wildtype male C57Bl/6 mice (≈20 g); ob/ob mice were 6- to 8-week old male mice; and DIO mice were 12-week old male mice having been on a high fat diet for 8 weeks. Mice were injected with either PBS, anti-miR-107 (1×15 mg/kg), anti-miR103 (2×15 mg/kg), anti-mm-107 (2×15 μg/kg), or anti-miR-124 (2×15 μg/kg).

Wild-Type Mice

Wild-type mice received two injections of 15 mg/kg anti-miR-103 or anti-mm-107, intraperitoneally. PBS was administered as a control treatment. Northern analysis of miR-103 and miR-107 demonstrated that anti-miR-103 silenced miR-107 in fat while having no effect o the expression of the unrelated microRNA miR-16. See FIG. 1d.

Following treatment, mice were tested for blood glucose levels, both in ad libitum fed and in fasted conditions. Silencing of miR-103/107 did not reveal any significant changes in blood glucose levels in wild-type mice. Wild-type mice also responded well to an intraperitoneal glucose challenge. Further, treatment with anti-miR-103 or anti-miR-107 did not cause overt toxicity, as judged by ALT levels (~25 IU/L and ~19 IU/L in mice treated with PBS and anti-miR-107, respectively; ~17 IU/L and ~18 IU/L in mice treated with PBS and anti-miR-103, respectively).

Ob/ob Mice

Ob/ob mice received two injections of 15 mg/kg anti-miR-103 or anti-miR-107, intraperitoneally. PBS was administered as a control treatment. Following treatment, mice were tested for blood glucose levels (with and without fasting), IPGTT, ITT, and pyruvate tolerance. Each treatment group contained 5 to 6 8-week old mice. Control treatments were PBS, anti-miR-124, or anti-mm-107. Northern analysis of miR-103 and miR-107 demonstrated that anti-miR-103 and anti-miR-107 effectively silenced both miR-103 and miR-107 in liver and fat while having no effect on the expression of the unrelated microRNA miR-16. See FIG. 1C, D.

To test blood glucose levels in the ad libitum fed condition, blood glucose was measured 2, 3, and 5 days after the second dose of anti-miR-103 or anti-miR-107. Inhibition of miR-103 resulted in a statistically significant reduction in blood glucose, compared to PBS treatment Inhibition of miR-107 also resulted in statistically significant reductions in blood glucose, compared to PBS treatment. See Table 10 (N.D. means 'not determined').

TABLE 10

Statistically Significant Reductions in Blood Glucose following anti-miR inhibition of miR-103/107

| Treatment | Random Blood Glucose (mM) | | | Blood glucose 8 h fast (mM) | |
|---|---|---|---|---|---|
| | Day 2 | Day 3 | Day 5 | Day 3 | Day 5 |
| PBS | 9.73 | 11.61 | 10.10 | 11.85 | 11.10 |
| anti-miR-103 | 7.67 | 6.77* | 7.25* | 6.69** | 6.61** |
| anti-miR-107 | 6.96** | 7.03* | 6.27** | N.D. | N.D. |
| anti-miR-124 | N.D. | N.D. | N.D. | 11.82 | 11.22 |

Significant reductions in blood glucose were also observed following 3 or 6 days of treatment with anti-miR-103, compared to anti-mm-107 treatment. See Table 11.

TABLE 11

Statistically significant reductions in blood glucose following anti-miR inhibition of miR-103/107

| | Random Blood Glucose (nM) | | |
|---|---|---|---|
| Treatment | Day 0 | Day 3 | Day 6 |
| anti-miR-103 | 8.58 | 5.50* | 6.33* |
| anti-mm-107 | 8.29 | 7.30 | 8.44 |

An IPGTT was also performed. Following a 16 hour fast, mice (n=5) received intraperitoneal injections of 2 grams of glucose per kg of body weight at day 6 after injection of anti-miR-103 or anti-miR-107. Blood was collected at 0, 15, 30, 60, 120, and 180 minutes. Statistically significant improvements in glucose tolerance were observed in mice treated with anti-miR-103 or anti-miR-107, compared to PBS control treatment. See Table 12. Statistically significant improvements in glucose tolerance are also evident when IPGTT results from anti-miR-103 treated mice are compared to IPGTT results from anti-miR-124 treated mice. See Table 13.

TABLE 12

IPGTT: anti-miR inhibition of miR-103/107 improves glucose tolerance

| | Blood Glucose (nM) after indicated time | | | | | |
|---|---|---|---|---|---|---|
| | 0 min | 15 min | 30 min | 60 min | 120 min | 180 min |
| PBS | 7.69 | 21.41 | 26.76 | 22.53 | 17.13 | 14.64 |
| anti-miR-103 | 6.13 | 16.66 | 22.83* | 19.70 | 11.28** | 9.73** |
| anti-miR-107 | 5.46 | 17.87* | 21.52* | 18.75 | 11.89** | 9.34** |

TABLE 13

IPGTT: anti-miR inhibition of miR-103 improves glucose tolerance

| | Blood Glucose (nM) after indicated time | | | | | |
|---|---|---|---|---|---|---|
| | 0 min | 15 min | 30 min | 60 min | 120 min | 180 min |
| anti-miR-124 | 7.65 | 21.43 | 26.54 | 22.74 | 17.03 | 14.49 |
| anti-miR-103 | 6.13 | 16.66* | 22.83* | 19.70 | 11.28** | 9.73** |

On day 9 following anti-miR treatment, an insulin tolerance test (ITT) was also performed in anti-miR-103 treated mice (n=5). 2 U insulin per kg bodyweight was administered following a 6 hour fast. Blood was collected at 0, 15, 30, 60, 90, and 120 minutes; values at 0 minutes were normalized to 100. Statistically significant reductions in blood glucose levels were observed relative to control treatment with PBS (see Table 14) or relative to control treatment with anti-miR-124 (see Table 15), indicating an improvement in insulin sensitivity.

TABLE 14

ITT: anti-miR-103 treatment improves insulin tolerance in ob/ob mice

| | Blood Glucose (nM) after indicated time | | | | | |
|---|---|---|---|---|---|---|
| | 0 min | 15 min | 30 min | 60 min | 90 min | 120 min |
| PBS | 100.00 | 111.79 | 104.84 | 82.89 | 75.19 | 77.12 |
| anti-miR-103 | 100.00 | 102.17 | 53.10*** | 43.00*** | 44.19** | 58.91 |

TABLE 15

ITT: Treatment with anti-miR-103 improves insulin tolerance in ob/ob mice

| | Blood Glucose (nM) after indicated time | | | | | |
|---|---|---|---|---|---|---|
| | 0 min | 15 min | 30 min | 60 min | 90 min | 120 min |
| anti-miR-124 | 100.00 | 121.66 | 110.72 | 86.92 | 77.80 | 80.24 |
| anti-miR-103 | 100.00 | 101.25 | 52.66 | 40.44 | 43.57 | 57.05 |

As a measure of gluconeogenesis (also known as de novo hepatic glucose production), a pyruvate tolerance test was performed (n=5). On day 12 following treatment with control or anti-miR-103, following an overnight (16 hour) fast mice (n=5) received intraperitoneal injections of 2 grams of pyruvate per kg body weight. Statistically significant reductions in blood glucose levels were observed. See Table 16. The decrease in gluconeogenesis was also supported by a reduction in hepatic levels of G-6-Pase, PC and FBPase in anti-miR-103 treated mice (n=5), compared to control mice (anti-mm-107; n=5). See Table 17.

TABLE 16

Treatment with anti-miR-103 decreases gluconeogenesis

| | Blood Glucose (nM) after indicated time | | | | |
|---|---|---|---|---|---|
| | 0 min | 15 min | 30 min | 60 min | 120 min |
| PBS | 6.78 | 16.48 | 16.35 | 12.40 | 10.20 |
| anti-miR-124 | 7.24 | 18.46 | 18.12 | 14.26 | 10.23 |
| anti-miR-103 | 5.53* | 13.65*** | 11.37 | 9.22* | 6.28** |

TABLE 17

Treatment with anti-miR-103 decreases expression of genes involved in gluconeogenesis

| | Relative Expression Levels | | |
|---|---|---|---|
| | G6Pc | PC | FBPase |
| anti-mm-107 | 1.03 | 1.02 | 1.01 |
| anti-miR-103 | 0.68** | 0.67** | 0.23*** |

Liver glycogen content was also measured (n=5 mice) and found to be increased in livers of anti-miR-103 (367 umol) treated mice relative to PBS-treated mice (246 umol) (BioVision Glycogen Assay Kit according to manufacturer's instructions).

Plasma insulin was measured (n=10 mice), after an overnight fast, and found to be reduced in mice treated with anti-miR-103 (26 ng/mL, $p<0.05$), compared to control-treated mice (anti-mm-107; 34 ng/mL).

Measurements of ALT indicated no overt toxicities. In ob/ob mice, ALT levels were 125 IU/L, 107 IU/L, 98 IU/L and 92 IU/L in mice treated with PBS, anti-miR-124, anti-miR-107, and anti-miR-103, respectively.

High-Fat Fed Obese Mice

Anti-miR-103 was also administered to high-fat fed obese mice (also called diet-induced obese mice or DIO mice), a model of impaired glucose tolerance and type 2 diabetes. Mice were kept on a high-fat diet for 12 weeks, starting at age 4 weeks. Mice received two injections of 15 mg/kg anti-miR-103. PBS was administered as a control treatment. Additional control treatments were anti-miR-124 or anti-mm-107. Each treatment group contained 4 to 5 mice.

After 3 days, blood glucose was measured and observed to be significantly reduced, in both the fed and fasted states, in anti-miR-103 treated mice (n=5; ~8 nM ad libitum, ~7.5 nM following 8 hour fast) relative to the PBS control (n=4; 10.5 nM ad libitum, 9.5 nM following 8 hour fast). Blood glucose in anti-miR-103 treated mice was also compared to anti-mm-107 treated mice, and found to be significantly reduced in both fed and fasted states. See Table 18.

TABLE 18

Anti-miR-103 treatment reduces fed and fasted blood glucose in DIO mice

| | Blood Glucose (nM) on indicated day (ad libitum unless otherwise indicated) | | | | | | |
|---|---|---|---|---|---|---|---|
| Treatment | 3 | 4 | 5 | 9 | 16 | 3 6 h fast | 17 12 h fast |
| anti-miR-124 | 8.55 | 9.38 | 8.93 | 9.35 | 9.10 | 7.33 | 9.10 |
| anti-miR-103 | 4.26*** | 5.14** | 6.70** | 7.92** | 7.92** | 3.64** | 7.62** |

On day 8 after anti-miR or PBS treatment, following an overnight (16 hour) fast, an IPGTT was also performed by administering 2 g/kg glucose; n=5 mice. Glucose tolerance was improved in a statistically significant manner, compared to PBS control treatment (see Table 19).

TABLE 19

Anti-miR-103 treatment improves glucose tolerance in DIO mice

| | Blood Glucose (nM) after indicated time | | | | | |
|---|---|---|---|---|---|---|
| | 0 min | 15 min | 30 min | 60 min | 120 min | 180 min |
| PBS | 7.55 | 24.68 | 31.10 | 29.10 | 18.98 | 12.53 |
| anti-miR-103 | 6.80 | 24.80 | 30.25 | 23.98* | 13.65** | 10.00* |

Measurement of plasma insulin levels (n=5 mice) revealed a reduction in plasma insulin in anti-miR-103 treated mice (5.4 ng/ml), relative to control treated mice (7 ng/ml, anti-mm-107).

Together, these data in animal models of diabetes and obesity demonstrate that inhibition of miR-103/107 enhances insulin sensitivity. Compounds that enhance insulin sensitivity are useful for the treatment and/or prevention of metabolic disorder, such as diabetes, pre-diabetes, metabolic syndrome, hyperglycemia, and insulin resistance.

Example 3

Overexpression of miR-107 Induces Hyperglycemia in Animals

To further investigate the role of miR-107, 8-week old male wild type mice were treated with an adenoviral vector expressing miR-107 (ad-107/GFP; n=5), which resulted in the overexpression of miR-107 in a variety of cell types and tissues, including liver. Mice treated with an adenoviral vector expression green fluorescent protein (GFP) (ad-GFP; n=5) were used as control animals. Each mouse received an injection of $5 \times 10^9$ viral particles.

Northern blotting revealed increased levels of miR-107, similar to levels observed in ob/ob mice (See FIG. 2A).

Blood glucose was found to be elevated in the mice treated with ad-107/GFP, relative to the mice treated with ad-GFP, in both fed and fasted animals (see Table 20). These data demonstrate that increased miR-107 expression leads to increases in blood glucose.

TABLE 20

Viral expression of miR-103 elevates blood glucose

| | Blood Glucose (nM) after indicated time | | | |
|---|---|---|---|---|
| | Day 5 | Day 7 | Day 8 | Day 8 8 hour fast |
| ad-GFP | 5.93 | 5.60 | 5.66 | 5.02 |
| ad-107/GFP | 7.30** | 7.52*** | 7.65** | 6.97*** |

The intraperitoneal glucose tolerance test (IPGTT) measures the clearance of intraperitoneally injected glucose from the body. This test was used to identify whether animals treated with ad-107/GFP exhibit impaired glucose tolerance Animals were fasted for approximately 15 hours, a solution of glucose was administered at 2 g/kg by intraperitoneal (IP) injection and blood glucose is measured at different time points during the 2 hours following the injection. Glucose (mg/dl) was measured in blood from tail bleeds at 0, 30, 60 and 120 min during IPGTT. The glucose area under the curve (AUC, mg/dl min) was calculated as an indication of impaired glucose tolerance according to the trapezoid rule from the glucose measurements at 0, 30, 60 and 120 min Animals treated with ad-107/GFP exhibited an impaired tolerance to glucose, relative to animals injected with ad-GFP. See Table 21.

TABLE 21

Viral overexpression of miR-107 impairs glucose tolerance

| | Blood Glucose (mM) at indicated time | | | | |
|---|---|---|---|---|---|
| | 0 min | 15 min | 30 min | 60 min | 120 min |
| ad-GFP | 3.78 | 11.68 | 8.38 | 6.40 | 4.23 |
| ad-miR-107/GFP | 4.13 | 17.07*** | 13.48*** | 8.90*** | 5.28 |

The insulin tolerance test (ITT) measures sensitivity to insulin. This test was used to identify whether the overexpression of miR-107 causes sensitivity to insulin. Five days following treatment with ad-107/GFP or ad-GFP, mice were fasted for approximately 6 hours and then given an intraperitoneal injection of 0.75 U/kg of insulin. Blood glucose was measured in blood from tail bleeds at 0, 15, 30, 60, 90 and 120 minutes during the ITT. At the 60 minute time point, animals treated with ad-107/GFP exhibited a decreased sensitivity to insulin, as measured by a higher amount of blood glucose at this time point, relative to animals treated with ad-GFP. See Table 22.

TABLE 22

Viral overexpression of miR-107 decreases insulin sensitivity

| | Blood Glucose (mM) at indicated time | | | | | |
|---|---|---|---|---|---|---|
| | 0 min | 15 min | 30 min | 60 min | 90 min | 120 min |
| ad-GFP | 100.00 | 57.48 | 35.05 | 22.20 | 27.80 | 100.00 |
| ad-107/GFP | 100.00 | 66.85 | 48.62 | 34.62* | 26.52 | 100.00 |

The pyruvate tolerance test measures gluconeogenesis, also known as de novo hepatic glucose production. This test was used to assess whether the overexpression of miR-107 adversely affects gluconeogenesis. Ten days following treatment with ad-107/GFP or ad-GFP, mice were fasted for approximately 15 hours and then given an intraperitoneal injection of 2 g/kg of pyruvate. Blood glucose was measured in blood from tail bleeds at 0, 20, 30, 60 and 120 minutes during the test. At the 30 minute time point and the 60 minute time point, animals treated with ad-107/GFP exhibited increased blood glucose relative to animals treated with ad-GFP, indicating an increase in gluconeogenesis as a result of overexpression of miR-107. See Table 23.

TABLE 23

Viral overexpression of miR-107 increases gluconeogenesis

| | Blood Glucose (mM) at indicated time | | | | |
|---|---|---|---|---|---|
| | 0 min | 15 min | 30 min | 60 min | 120 min |
| ad-GFP | 3.72 | 6.70 | 7.84 | 6.74 | 4.30 |
| ad-107/GFP | 3.33 | 7.00 | 9.07 | 8.76*** | 5.08 |

Real-time PCR was used to measure levels of genes associated with gluconeogenesis; levels were normalized to 36B4; n=5 mice. Additionally, the increase in hepatic glucose production was accompanied by augmented expression of glucose 6-phosphatase (G6Pc), phosphoenol pyruvate carboxykinase (Pepck), pyruvate carboxylase (PC) and fructose 1,6 bisphosphatase (FBPase), suggesting that increased gluconeogenesis is the primary cause of the elevated glucose levels. See Table 24. These data demonstrated that overexpression of miR-107 enhances de novo hepatic glucose production.

TABLE 24

Viral overexpression of miR-107 decreases expression of genes associated with gluconeogenesis

| | Blood Glucose (mM) at indicated time | | | |
|---|---|---|---|---|
| | G6Pc | Pepck | PC | FBPase |
| ad-GFP | 0.98 | 1.07 | 1.01 | 1.10 |
| ad-107/GFP | 2.00*** | 1.39* | 1.23* | 1.73* |

Non-esterified fatty acids (NEFAs) were also measured, and found to be decreased when miR-107 was overexpressed (~0.25 nmol/uL in ad-GFP treated mice; ~0.30 nmol/uL, $p<0.05$, in ad-107/GFP treated mice).

These results demonstrate that increased expression of miR-107 results in an impaired tolerance to glucose, a decreased sensitivity to insulin, and increased gluconeogenesis. MiR-107 and miR-103 share a seed sequence, and are expected to regulate similar targets, effects observed following overexpression of miR-107 may also be observed upon overexpression of miR-103. Thus, miR-107 and miR-103 are targets for the treatment of metabolic disorders, including but not limited to diabetes and insulin resistance.

Example 4

Inhibition of miR-103 or miR-107 Decreases Plasma Cholesterol

The inhibition of miR-103 or miR-107 was additionally tested for its effects on blood lipid levels in both wild-type (C57Bl/6, 8 week-old) and ob/ob mice (12 week-old, on high fat diet for 8 weeks). Each treatment group contained 5 mice. In this experiment, anti-miR-103 comprised the sequence of SEQ ID NO: 6,2'-O-methyl modifications at each sugar, phosphorothioate modifications at each of the first 4 internucleoside linkages (at the 5' end), phosphorothioate modifications at each of the last 2 internucleosides linkages (at the 3' end), and a cholesterol conjugate. Anti-miR-107 comprised the sequence of SEQ ID NO: 7,2'-O-methyl modifications at each sugar, phosphorothioate modifications at each of the first 4 internucleoside linkages (at the 5' end), phosphorothioate modifications at each of the last 2 internucleosides linkages (at the 3' end), and a cholesterol conjugate.

Wild-type mice were injected with PBS, a single intraperitoneal injection of anti-miR-107 at a dose of 15 mg/kg, or two intraperitoneal injections of anti-miR-103 at a dose of 15 mg/kg. Ob/ob mice were injected with PBS, a single intraperitoneal injection of anti-miR-107 at a dose of 15 mg/kg, or two intraperitoneal injections of anti-miR-103 at a dose of 15 mg/kg.

Total plasma cholesterol was measured and was found to be significantly lowered in ob/ob mice treated with anti-miR-103 (1.75 ug/ul, $p<0.001$; n=5) or anti-miR-107 (1.86 ug/ul, $p<0.001$; n=5), relative to PBS-treated mice (2.67 ug/ul; n=5). HDL and LDL fractions of total plasma cholesterol were measured by FPLC gel filtration from 200 ul of plasma, revealing a preferential reduction in LDL cholesterol (See Table 25). To measure the number of LDL and HDL particles, immunoblotting was performed using apolipoprotein B detection to measure the number of LDL particles and apolipoprotein A1 detection to measure the number of HDL particles (See FIG. 3A).

TABLE 25

Anti-miR-103 treatment preferentially reduces LDL cholesterol in ob/ob mice

| Fraction | PBS | anti-miR-103 |
|---|---|---|
| 1 | 0.68 | 0.70 |
| 2 | 0.72 | 0.69 |
| 3 | 0.70 | 0.72 |
| 4 | 0.68 | 0.68 |
| 5 | 0.65 | 0.68 |
| 6 | 0.71 | 0.71 |
| 7 | 0.70 | 0.68 |
| 8 | 0.66 | 0.70 |
| 9 | 0.67 | 0.67 |
| 10 | 0.70 | 0.68 |
| 11 | 0.72 | 0.68 |
| 12 | 0.69 | 0.68 |
| 13 | 0.63 | 0.66 |
| 14 | 0.69 | 0.69 |
| 15 | 0.69 | 0.83 |
| 16 | 0.70 | 0.89 |
| 17 | 0.77 | 0.93 |
| 18 | 0.80 | 0.96 |
| 19 | 0.87 | 1.01 |
| 20 | 1.00 | 1.09 |
| 21 | 1.18 | 1.22 |
| 22 | 1.42 | 1.39 |
| 23 | 1.81 | 1.70 |
| 24 | 2.34 | 2.04 |
| 25 | 2.99 | 2.58 |
| 26 | 3.74 | 3.13 |
| 27 | 4.52 | 3.62 |
| 28 | 5.20 | 3.96 |
| 29 | 5.67 | 3.92 |
| 30 | 5.86 | 3.93 |
| 31 | 5.83 | 3.81 |
| 32 | 5.81 | 3.82 |
| 33 | 5.58 | 3.84 |
| 34 | 5.47 | 3.91 |
| 35 | 5.34 | 3.99 |
| 36 | 5.19 | 4.16 |
| 37 | 5.24 | 4.72 |
| 38 | 5.71 | 3.66 |
| 39 | 6.49 | 6.55 |
| 40 | 7.86 | 7.94 |
| 41 | 8.74 | 8.37 |
| 42 | 8.89 | 7.88 |
| 43 | 8.10 | 6.82 |
| 44 | 6.47 | 5.19 |
| 45 | 4.91 | 3.95 |
| 46 | 3.53 | 2.92 |
| 47 | 2.56 | 2.19 |
| 48 | 1.91 | 1.70 |
| 49 | 1.43 | 1.30 |
| 50 | 1.06 | 0.98 |
| 51 | 0.94 | 0.85 |
| 52 | 0.81 | 0.78 |
| 53 | 0.82 | 0.78 |
| 54 | 0.83 | 0.76 |
| 55 | 0.86 | 0.82 |
| 56 | 0.83 | 0.82 |
| 57 | 0.82 | 0.79 |
| 58 | 0.80 | 0.80 |
| 59 | 0.81 | 0.79 |
| 60 | 0.77 | 0.74 |

Non-esterified fatty acids were also measured, and observed to be increased following inhibition of miR-103 (~0.5 nm01/ul) or miR-107 (~0.45 nmol/ul), relative to PBS treatment (~0.35 nmol/ul); n=5 for each group.

8-week old LDL-receptor deficient mice (LDLR−/− mice) were also treated with anti-miR-103 or PBS (n=3), and the major lipoprotein fractions were separated by FPLC gel filtration from 150 ul of plasma and assayed for VLDL, HDL, and LDL fractions. Western blotting was also performed on the fractions assayed for cholesterol, using apolipoprotein B antibody to detect the number of LDL particles and apolipoprotein A1 antibody to detect the number of HDL particles (See FIG. 3B). A preferential reduction in LDL cholesterol was observed (See Table 26). A decrease in VLDL indicates a decrease in triglyceride (See FIG. 3C).

TABLE 26

Preferential reduction in LDL cholesterol in LDLR −/− mice

| Fraction | PBS | anti-miR-103 |
| --- | --- | --- |
| 1 | −0.02 | −0.08 |
| 2 | −0.03 | 0.16 |
| 3 | −0.06 | −0.06 |
| 4 | −0.09 | −0.12 |
| 5 | −0.08 | −0.08 |
| 6 | −0.05 | 0.00 |
| 7 | −0.08 | −0.02 |
| 8 | −0.06 | −0.03 |
| 9 | −0.07 | −0.03 |
| 10 | −0.06 | −0.04 |
| 11 | −0.05 | −0.05 |
| 12 | −0.06 | −0.07 |
| 13 | −0.10 | −0.11 |
| 14 | −0.05 | −0.08 |
| 15 | 0.28 | −0.07 |
| 16 | 0.75 | −0.07 |
| 17 | 0.84 | 0.03 |
| 18 | 0.83 | 0.19 |
| 19 | 1.14 | 0.39 |
| 20 | 0.97 | 0.55 |
| 21 | 1.18 | 0.83 |
| 22 | 1.65 | 1.21 |
| 23 | 2.46 | 1.89 |
| 24 | 3.69 | 2.84 |
| 25 | 5.29 | 3.95 |
| 26 | 6.88 | 5.28 |
| 27 | 8.67 | 6.51 |
| 28 | 10.06 | 7.24 |
| 29 | 10.23 | 7.72 |
| 30 | 9.82 | 7.49 |
| 31 | 8.68 | 6.67 |
| 32 | 7.36 | 5.67 |
| 33 | 5.85 | 4.55 |
| 34 | 4.62 | 3.63 |
| 35 | 3.58 | 2.84 |
| 36 | 2.78 | 2.23 |
| 37 | 2.35 | 1.89 |
| 38 | 2.18 | 1.80 |
| 39 | 2.18 | 1.91 |
| 40 | 2.56 | 2.44 |
| 41 | 3.33 | 3.38 |
| 42 | 4.67 | 4.99 |
| 43 | 6.31 | 6.75 |
| 44 | 7.46 | 7.74 |
| 45 | 8.00 | 7.90 |
| 46 | 7.50 | 6.70 |
| 47 | 6.06 | 5.25 |
| 48 | 4.23 | 3.73 |
| 49 | 2.97 | 2.55 |
| 50 | 1.82 | 1.58 |
| 51 | 1.06 | 0.89 |
| 52 | 0.62 | 0.50 |
| 53 | 0.38 | 0.28 |
| 54 | 0.30 | 0.17 |
| 55 | 0.28 | 0.19 |
| 56 | 0.24 | 0.19 |
| 57 | 0.23 | 0.18 |
| 58 | 0.20 | 0.18 |
| 59 | 0.23 | 0.15 |
| 60 | 0.14 | 0.09 |

These data demonstrate further that inhibition of miR-103 or miR-107 reduces cholesterol levels, preferentially LDL cholesterol levels, in addition to reducing blood glucose levels, improving insulin sensitivity, reducing gluconeogenesis, and improving glucose tolerance.

Example 5

Analysis of Gene Expression Regulation by miR-103 or miR-107

To address the possible mechanism by which miR-103 and miR-107 regulate insulin sensitivity, RNA expression analysis was performed to measure genes in tissues in which miR-103/107 was inhibited or over-expressed. Real-time PCR was conducted to measure the RNA levels of genes that are predicted to be targets of miR-103 or miR-107. Microarray analysis was performed to measure genome-wide changes in gene expression. As the sequences of miR-103 and miR-107 differ only by one nucleobase, they are expected to have overlapping sets of target genes.

To address the possible mechanism by which miR-103 and miR-107 regulate insulin sensitivity, genome-wide expression analysis was performed using Affymetrix microarrays, to compare livers from C57Bl/6J mice infected with Ad-107/GFP and Ad-GFP, 10 days after administration of the virus (n=5 per treatment). In the livers of Ad-107/GFP mice, mRNAs carrying a seed match to miR-107 in the 3'UTR were significantly down-regulated compared to mRNAs whose 3'UTR did not carry a miR-107 seed match, with the down-regulation being more pronounced for the subset of mRNAs harboring seed matches inferred to be under evolutionary selective pressure (FIG. 2B). The data were confirmed for a subset of miR-107 target genes by real-time PCR (see Table 27) performed on RNA collected from the livers of C57Bl/6 mice infected with recombinant adenovirus expressing miR-107 (as in Example 2). A reduction in RNA levels in presence of adenovirus expressing miR-107, relative to the control virus Ad-GFP, indicates that the RNA is a target of miR-103/107. Analysis of the functional annotation of the down-regulated genes indicated that metabolism would be affected by miR-103/107.

TABLE 27

Changes in gene expression following viral overexpression of miR-107

| LIVER C57bl/6 | ad-GFP | ad-107/GFP |
| --- | --- | --- |
| G6Pc | 0.98 | 2.00*** |
| PEPCK | 1.07 | 1.39* |
| Pyruvate carboxylase | 1.01 | 1.23* |
| Fructose 1,6 bisphosphatase | 1.10 | 1.73* |
| Cav1 | 1.0000 | 0.7066** |
| Gpnmb | 0.9548 | 0.1521*** |
| Prom1 | 1.0934 | 0.4454** |
| LPL | 1.0564 | 0.4401*** |
| Pla2 (g4) | 1.0345 | 0.3492*** |
| Pla2 (g7) | 1.0982 | 0.4065*** |
| LYPLA2 | 1.0000 | 0.8787* |
| LYPLA3 | 1.0050 | 0.5679*** |
| Pld1 | 1.0000 | 0.7548** |
| Pld3 | 1.0274 | 0.5772*** |
| ApoBEC1 | 1.0055 | 0.5709*** |
| ApoB48r | 1.1630 | 0.3833*** |

Real-time PCR was performed on RNA collected from the livers of ob/ob mice treated with anti-miR-103 or anti-miR-107 (as in Example 1; n=5 mice). An increase in RNA levels in the presence of anti-miR-103 or anti-miR-107, relative to the PBS control, indicates that the RNA is a target of miR-103 or miR-107. See Table 28 and additional gene expression data in FIG. 4A.

TABLE 28

Changes in liver gene expression following inhibition of miR-103 in ob/ob mice

|  | PBS | anti-miR-103 |
|---|---|---|
| Cav1 | 1.0021 | 1.2232 |
| Gpnmb | 1.0037 | 2.5821 |
| Prom1 | 0.9992 | 1.5617 |
| LPL | 1.0040 | 1.2673 |
| Pla2 (g7) | 1.0002 | 1.3347 |
| ApoBEC1 | 1.0031 | 1.2115 |
| BCKDHA | 1.0003 | 0.3698 |
| SAA1 | 1.0020 | 0.4313 |
| SAA3 | 1.1023 | 0.4360 |
| LCN2 | 1.0020 | 0.4044 |

Real-time PCR was performed on RNA collected from the livers of LDLR−/− mice treated with anti-miR-103 (as in Example 4). An increase in RNA levels in the presence of anti-miR-103, relative to the PBS control, indicates that the RNA is a target of miR-103. See Table 29.

TABLE 29

Anti-miR-103 increases gene expression in liver of LDLR−/− mice

|  | PBS | anti-miR-103 |
|---|---|---|
| LPL | 1.0026 | 1.8160*** |
| Pla2g4 | 1.0123 | 1.7222*** |
| Pla2g7 | 1.0690 | 3.0274*** |
| ApoBEC1 | 1.0223 | 1.8388*** |
| LYPLA3 | 1.0300 | 1.4017** |
| ApoB48r | 1.0891 | 1.3525* |
| LIPIN1 | 0.9896 | 1.3751** |

Real-time PCR was performed on RNA collected from the fat of ob/ob or C57Bl/6 mice treated with anti-miR-103 or anti-miR-107 (as in Example 1). An increase in RNA levels in the presence of anti-miR-103 or anti-miR-107, relative to the PBS control, indicates that the RNA is a target of miR-103 or miR-107. See Table 30 and additional gene expression data in FIG. 4B.

TABLE 30 mRNA increases in fat of ob/ob mice following anti-miR-103 treatment

|  | ob/ob | | C57B1/6 | |
|---|---|---|---|---|
|  | PBS | anti-miR-103 | PBS | anti-miR-103 |
| LPL | 1.0241 | 1.7775** | 1.0937 | 2.3323*** |
| Lipin1 | 1.0238 | 1.5320** | 1.2662 | 2.1105** |
| Cav1 | 0.9860 | 3.4585*** | 1.5891 | 2.3680* |
| Pla2(g7) | 0.9851 | 1.4429* | N.D. | N.D. |

Real-time PCR was performed on RNA collected from the muscle of ob/ob or C57Bl/6 mice treated with anti-miR-103 (as in Example 1). An increase in RNA levels in the presence of anti-miR-103, relative to the PBS control, indicates that the RNA is a target of miR-103 or miR-107. See Table 31 and additional gene expression data in FIG. 4C.

TABLE 31 mRNA changes in muscle of ob/ob mice following anti-miR-103 treatment

|  | ob/ob | |
|---|---|---|
|  | PBS | anti-miR-103 |
| LPL | 1.0215 | 1.4497** |
| Cav1 | 1.0238 | 1.4333** |
| G6Pc | 0.9538 | 0.5288* |
| PC | 0.9840 | 0.1578*** |
| BCAT2 | 1.0199 | 1.5041*** |

Caveolin 1 (Cav1), a key component of caveolae in adipocytes and a mediator of insulin signaling, was among the miR-103/107 seed containing genes that were down- or up-regulated in insulin-sensitive tissues following miR-107 over-expression and silencing, respectively. As illustrated in the above tables, Cav1 transcript levels were reduced approximately 30% in livers of C57Bl/6 mice injected with ad-107/GFP (relative expression of 0.71 in ad-107/GFP mice vs. ad-GFP mice) and increased approximately 22% in livers of anti-miR-103 injected ob/ob mice (relative expression of 1.22 vs. PBS-treated mice). Anti-miR-103 treatment of C57Bl/6 mice lead to a 1.5-fold increase in fat Cav1 mRNA levels (relative expression of 2.37 vs. 1.59 in PBS-treated mice). Strikingly, miR-103 silencing in the fat of ob/ob mice increased Cav1 mRNA levels approximately 3.5-fold (relative expression of 3.45 vs. PBS-treated mice), and miR-103 silencing in muscle resulted in approximately 1.4-fold up-regulation of Cav1 mRNA levels (1.43 relative expression vs. PBS-treated mice).

To test if Cav1 expression is directly regulated by miR-103/107 the coding sequence and 3'UTR were analyzed for functional binding sites. Murine Cav1 (mCav1) contains three miR-103 seed motifs in the 3'UTR, while human Cav1 (hCav1) has three 6-mer seed motifs, one in the 5', and two in the 3' UTR (FIG. 9).

A luciferase assay was used to test contructs containing either the full-length or partial 3'UTR of miR-103/107 target genes, as an additional confirmation that the genes are regulated by miR-103/107. Measurements of luciferase activity from HEK293 cells transfected with plasmid constructs containing the 3'UTR mouse and human Cav1 (mCav1 and hCav1, respectively) showed reduced expression of these reporter constructs in the presence of miR-103 (see Table 32). Mutating the seed, also conserved in mouse (NM_001753 in RefSeq, 2004-2009 (ATGCTG)), resulted in the full reversal of the miR-103-induced decrease of the luciferase activity in both hCav1 3'UTR constructs (NM_001753, 1505-2679 nt(L), and 1749-2679 nt(S)). Furthermore, the total luciferase activity in the mutant 3'UTR hCav1 was increased compared to the wildtype 3'UTR hCav1, likely due to the derepression through the endogenously expressed miR-103.

TABLE 32

Caveolin 1 is a target of miR-103

|  | Relative Luciferase Activity (firefly/renilla) | | |
|---|---|---|---|
|  | Mock | miR-103 | Scrambled 1 |
| mCav1 long | 1 | 0.76* | 0.96 |
| hCav1 short | 1 | 0.8 | 0.93 |
| hCav1 long | 1 | 0.86* | 0.98 |
| hCav1 mut short | 1 | 1.1 | 0.98 |
| hCav1 mut long | 1 | 1.05 | 0.99 |

TABLE 32-continued

Caveolin 1 is a target of miR-103

| | Relative Luciferase Activity (firefly/renilla) | | |
|---|---|---|---|
| | Mock | miR-103 | Scrambled 1 |
| Total hCav1 mut/wt short | | 1.16** | |
| Total hCav1 mut/wt long | | 1.21** | |

Among other RNAs, Caveolin 1 and lipin were identified as targets of miR-103/107. These genes are candidates for the targets that mediate the effects of anti-miR-103 and/or anti-miR-107.

Example 6

Analysis of miR-103 or miR-107 Target Protein Expression

To further understand the regulation of target genes by miR-103 or miR-107, samples from anti-miR treated mice were analyzed for protein expression.

Western blotting was performed on protein extracts from fat tissue of ob/ob mice treated with PBS or anti-miR-103 (as described in Example 1). Membranes were probed for Caveolin 1, Insulin receptor beta, pAKT, AKT, and gamma-tubulin. Phosphorylated p-AKT was observed to be increased. As pAKT is a kinase that is activated by insulin signaling, increased p-AKT levels at similar plasma insulin levels indicated increased insulin sensitivity. See FIG. 5A.

HEK293 cells were also treated with anti-miR-103, and cells were harvested 3 days following anti-miR treatment. Western blotting was performed to detect Caveolin 1 and gamma-tubulin. Caveolin 1 protein levels increased with increasing concentrations of anti-miR-103, indicating that Caveloin 1 was de-repressed by inhibition of miR-103. See FIGS. 5B and 5D.

Northern blotting was used to detect miR-103 in HEK293 cells treated as in FIG. 5B. See FIG. 5C.

To evaluate the effects of adding miR-103 to cells, HEK293 cells were transfected with miR-103 siRNA. Control siRNAs were also used. The addition of miR-103 caused reduced levels of Caveolin 1 protein. See FIGS. 5E and 5F.

To evaluate the effects of adding miR-103 to cells, 3T3 cells were transfected with miR-103 siRNA. Control siRNAs were also used. The addition of miR-103 caused reduced levels of Caveolin 1 protein. See FIG. 5G.

Taken together with the results on mRNA expression, these data demonstrate that Cav1 is a direct target of miR-103 in both mouse and in human.

Example 7

Contribution of Liver to miR-103 Mediated Effects on Insulin Sensitivity

To test the relative contribution of the liver for the effect on insulin sensitivity, liposomal formulations were used to deliver anti-miR primarily to the liver. Liver-targeting lipid nanoparticle (LNP) formulations of anti-miR were prepared using the novel ionizable lipid DLin-KC2-DMA (Semple et al., Nature Biotechnology, 28, 172-176 (2010)). LNPs were comprised of DLin-KC2-DMA, distearoyl phosphatidylcholine (DSPC), cholesterol and mPEG2000-DMG, utilized at the molar ratio of 50:10:38.5:1.5. Ant-miRs were formulated in the LNPs at a total lipid:anti-miR weight ratio of approximately 11:1.

Anti-miR-103 or anti-mm-107, formulated in liposomes, was administered to mice at a dose of 15 mg/kg of anti-miR (n=8 mice for anti-miR-103, n=7 mice for anti-mm-107). Mice received one injection per day, for two days. Northern blotting was performed using 30 ug of total RNA from liver, fat or muscle. Liposome-formulated anti-miR-103, but not liposome-formulated anti-mm-107, induced specific and potent silencing of miR-103 in liver, but not in fat and muscle. See FIG. 6. Silencing of miR-103/107 in livers of ob/ob mice neither had a significant effect on blood glucose levels in random and fasting conditions (see Table 33), nor did this treatment result in improved insulin sensitivity. This observation indicates that the insulin-sensitizing actions of miR-103/107 are mainly mediated by extrahepatic tissues such as fat and muscle.

TABLE 33

Liposomally formulated anti-miR-103 does not significantly affect blood glucose

| | Blood Glucose (mM) | | | | | | |
|---|---|---|---|---|---|---|---|
| ob/ob | D0 6 h fast | D3 random | D3 6 h fast | D5 random | D5 6 h fast | D8 12 h fast | D9 12 h fast |
| Lip-anti-mm-107 | 7.4429 | 13.7857 | 7.7000 | 7.5833 | 9.7667 | 6.4000 | 10.4286 |
| Lip-anti-miR-103 | 7.4125 | 9.6250 | 7.1000 | 7.1625 | 7.9000 | 5.0750 | 8.3000 |

Example 8

Effects of miR-103 Inhibition in Adipose Tissue

Since the expression of miR-103 is approximately 8-fold higher in adipose tissue compared to liver and muscle, the effects of silencing miR-103/107 in adipose tissue were examined in more detail.

Obese (ob/ob) mice exhibited a slight reduction in body weight when miR-103/107 was systemically silenced using anti-miR-103 compared to control-treated mice. See Table 34. In contrast, manipulation of miR-103/107 expression in the liver using liposomally-formulated anti-miR-103 or Ad-107/GFP did not affect body weight compared to control treated mice. In light of this observation, the fat distribution of both high-fat fed obese and ob/ob animals was investigated by computer tomography (CT) 13 days following treatment with anti-miR or control. See FIG. 7A. Both high-fat fed and ob/ob mice treated with anti-miR-103 had reduced total fat due to a decrease in both subcutaneous (SC) and visceral (V) fat (See Tables 34 and 35).

TABLE 34

Anti-miR-103 decreases subcutaneous and visceral fat

Computer Tomography at Day 13

| | Subcutaneous | | Visceral | | Total | |
|---|---|---|---|---|---|---|
| | ob/ob | DIO | ob/ob | DIO | ob/ob | DIO |
| anti-MM-103 | 8.16 | 5.44 | 16.58 | 12.06 | 30.18 | 34.07 |
| anti-miR-103 | 7.46 | 3.87 | 15.38 | 10.18 | 26.71* | 29.43* |

TABLE 35

Anti-miR-107 reduces body weight of obese ob/ob mice

| | Body Weight (g) | | | | | |
|---|---|---|---|---|---|---|
| ob/ob | Day 0 | Day 3 | Day 6 | Day 12 | Day 15 | Day 16 |
| anti-MM-103 | 44.21 | 46.10 | 47.84 | 50.17 | 49.76 | 48.80 |
| anti-miR-103 | 43.94 | 45.55 | 46.16 | 47.89 | 47.10 | 46.14* |

To investigate whether this reduction is due to lower cell numbers or smaller adipocytes, mean adipocyte cell size from fat tissue sections was quantified using an automated image analysis software. Anti-miR-103 treated high-fat fed obese and ob/ob animals had smaller adipocytes compared to anti-mm-107 injected controls (FIG. 7B, 7C; quantification in Table 36).

TABLE 36

Anti-miR-103 treatment results in smaller adipocyte size

| | DIO | | ob/ob | |
|---|---|---|---|---|
| | SC | V | SC | V |
| anti-miR-124 | N.D. | N.D. | 23533.66 | 25163.76 |
| anti-MM-107 | 23794.78 | 25325.03 | 24193.78 | 24890.49 |
| anti-miR-103 | 19523.82*** | 20822.32*** | 19520.48*** | 20822.43*** |

Also observed was a significant increase in the number of small adipocytes and a decrease in large adipocytes (See Tables 37 and 38; values are normalized to the total cell number).

TABLE 37

DIO mice: anti-miR-103 increases the small adipocyte number and decreases large adipocyte number

| | SC | | V | |
|---|---|---|---|---|
| | anti-MM-107 | anti-miR-103 | anti-mm-107 | anti-miR-103 |
| 1 | 0.0000 | 0.0000 | 0.0000 | 0.0000 |
| 2 | 0.0490 | 0.0680 | 0.0308 | 0.0641* |
| 3 | 0.1194 | 0.1392 | 0.0576 | 0.1171* |
| 4 | 0.1057 | 0.1386*** | 0.1033 | 0.1200 |
| 5 | 0.1015 | 0.1239 | 0.1054 | 0.1075 |
| 6 | 0.0949 | 0.0918 | 0.0985 | 0.1053 |
| 7 | 0.0873 | 0.0845 | 0.0781 | 0.0837 |
| 8 | 0.0619 | 0.0639 | 0.0870 | 0.0850 |
| 9 | 0.0594 | 0.0501 | 0.0671 | 0.0648 |
| 10 | 0.0443 | 0.0522 | 0.0556 | 0.0431** |
| 11 | 0.0410 | 0.0393 | 0.0574 | 0.0400* |
| 12 | 0.0348 | 0.0333 | 0.0474 | 0.0329 |
| 13 | 0.0276 | 0.0296 | 0.0438 | 0.0340 |
| 14 | 0.0227 | 0.0188 | 0.0256 | 0.0186 |
| 15 | 0.0223 | 0.0162 | 0.0172 | 0.0209 |
| 16 | 0.0183 | 0.0122 | 0.0222 | 0.0112*** |
| 17 | 0.0217 | 0.0100* | 0.0220 | 0.0137 |
| 18 | 0.0155 | 0.0073 | 0.0144 | 0.0087 |
| 19 | 0.0166 | 0.0058* | 0.0181 | 0.0046** |
| 20 | 0.0166 | 0.0050** | 0.0128 | 0.0051* |
| 21 | 0.0110 | 0.0035* | 0.0100 | 0.0075 |
| 22 | 0.0099 | 0.0037 | 0.0096 | 0.0046* |
| 23 | 0.0059 | 0.0023 | 0.0081 | 0.0026* |
| 24 | 0.0057 | 0.0008** | 0.0060 | 0.0017 |
| 25 | 0.0033 | 0.0000 | 0.0014 | 0.0000 |
| 26 | 0.0016 | 0.0000 | 0.0007 | 0.0000 |
| 27 | 0.0016 | 0.0000 | 0.0000 | 0.0000 |
| 28 | 0.0005 | 0.0000 | 0.0000 | 0.0000 | n = 6 for anti-mm-107;
n = 7 for anti-miR-103

TABLE 38

Ob/ob mice: anti-miR-103 increases small adipocyte number and decreases large adipocytenumber

| | SC | | V | |
|---|---|---|---|---|
| | anti-mm-107 | anti-miR-103 | anti-mm-107 | anti-miR-103 |
| 1 | 0.0000 | 0.0006 | 0.0000 | 0.0000 |
| 2 | 0.0524 | 0.0860** | 0.0518 | 0.0767** |
| 3 | 0.0965 | 0.1275** | 0.0862 | 0.1016** |
| 4 | 0.1005 | 0.1302*** | 0.0878 | 0.1118** |
| 5 | 0.0927 | 0.1129** | 0.0868 | 0.1000 |
| 6 | 0.0900 | 0.0958 | 0.0871 | 0.1044** |
| 7 | 0.0886 | 0.0883 | 0.0858 | 0.0922 |
| 8 | 0.0697 | 0.0687 | 0.0741 | 0.0786 |
| 9 | 0.0601 | 0.0592 | 0.0672 | 0.0735 |
| 10 | 0.0555 | 0.0451** | 0.0571 | 0.0524 |
| 11 | 0.0484 | 0.0384* | 0.0452 | 0.0442 |
| 12 | 0.0388 | 0.0313 | 0.0478 | 0.0397 |
| 13 | 0.0282 | 0.0250 | 0.0438 | 0.0256*** |
| 14 | 0.0299 | 0.0239 | 0.0390 | 0.0252*** |
| 15 | 0.0307 | 0.0154*** | 0.0255 | 0.0167* |
| 16 | 0.0243 | 0.0139** | 0.0224 | 0.0128** |
| 17 | 0.0185 | 0.0112** | 0.0191 | 0.0139* |
| 18 | 0.0178 | 0.0097** | 0.0163 | 0.0100** |
| 19 | 0.0160 | 0.0083** | 0.0134 | 0.0087* |
| 20 | 0.0125 | 0.0065* | 0.0126 | 0.0058** |
| 21 | 0.0091 | 0.0010*** | 0.0103 | 0.0020*** |
| 22 | 0.0083 | 0.0003*** | 0.0084 | 0.0028*** |
| 23 | 0.0074 | 0.0003*** | 0.0071 | 0.0008*** |
| 24 | 0.0042 | 0.0003** | 0.0051 | 0.0006*** |
| 25 | 0 | 0 | 0 | 0 |
| 26 | 0 | 0 | 0 | 0 |
| 27 | 0 | 0 | 0 | 0 |
| 28 | 0 | 0 | 0 | 0 | n = 4 for anti-mm-107;
n = 5 for anti-miR-103

Comparing the decrease in fat pad size measured by CT with the average decrease in adipocyte size showed that anti-miR-103 mice had approximately 10-20% more adipocytes than anti-mm-107 controls. To explore whether this could be attributed to changes in the preadipocyte differentiation, stromal-vascular fraction (SVF) was isolated from both V and SC fat of wildtype mice, and differentiation was induced in the presence of either anti-miR-103 or anti-mm-107. After 8 days in culture, anti-miR-103 transfected cells contained more mature adipocytes than the cells from anti-mm-107 (FIG. 7D), indicating that the absence of miR-103 enhances adipocyte differentiation in a cell autonomous fashion. Quantification of adipocyte number by high content imaging demonstrated approximately 2 and 2.5-fold increases of differentiated adipocytes in the anti-miR-103 treated SVF derived from V or SC fat, respectively (see Table 39). Conversely, Ad-107/GFP-mediated miR-107 over-expression led to 3.7-fold decrease in the number of differentiated adipocytes compared to Ad-GFP control infected SVF (See Table 39).

TABLE 39 anti-miR-103 treatment increases differentiated adipocytes

| | Relative number of differentiated cells | |
|---|---|---|
| | SC | V |
| anti-mm-107 | 1.00 | 1.00 |
| anti-miR-103 | 1.75*** | 2.51** |
| ad-GFP | N.D. | 1.00 |
| ad-107/GFP | N.D. | 0.28*** |

The negative regulation of miR-103 on preadipocyte differentiation was further corroborated by gene expression analysis of adipocyte differentiation markers Ap2, and PPAR-gamma. Both markers exhibited increased mRNA levels in differentiated SVF in which miR103/107 was silenced with anti-miR-103 compared to the anti-mm-107 control (see Tables 40).

TABLE 40

Adipocyte differentiation markers increase following inhibition of miR-103/107

| | AP2 Relative Gene Expression | | | | PPARγ Relative Gene Expression | | | |
|---|---|---|---|---|---|---|---|---|
| | 0 h | 24 h | 48 h | 96 h | 0 h | 24 h | 48 h | 96 h |
| Mock | 0.96 | 3.80 | 12.62 | 37.16 | 0.99 | 1.69 | 2.15 | 5.68 |
| anti-mm-107 | 0.96 | 3.80 | 14.92 | 57.24 | 0.99 | 1.71 | 2.12 | 7.36 |
| anti-miR-103 | 0.96 | 3.85 | 19.31 | 92.78*** | 0.99 | 1.91 | 2.92* | 9.34* |

Example 9 miR-103-Mediated Glucose Uptake

Smaller adipocytes are associated with increased insulin sensitivity in human and rodent models. To explore if insulin-stimulated glucose uptake in adipocytes was affected by miR-103 inhibition, primary adipocytes were isolated from either anti-miR-103, or control treated ob/ob mice, and insulin-stimulated D-$^{14}$C-glucose uptake was measured in vitro.

In one study, primary adipocytes were isolated from 7 month old ob/ob mice treated with PBS or anti-miR-103 (2 injections of 15 mg/kg each). Anti-miR-124 or anti-mm-107 was used as a control anti-miR. Mice were sacrificed 6 days after injection following a 15 hour fast, and the primary subcutaneous (SC) or visceral (V) adipocyte fractions were preincubated for 10 minutes with or without 20 nM insulin, and then for an additional 1 hour with 1 mM $^{14}$C-labeled glucose. Anti-miR-103 improved insulin-stimulated glucose uptake in adipocyte cells, relative to PBS or anti-miR-124 treatment, indicating an increase in insulin sensitivity. See Table 41. Glucose uptake after stimulation with 20 nM insulin was significantly higher in the anti-miR-103 adipocytes compared to the controls (anti-mm-107 or PBS) (Table 41).

TABLE 41

Anti-miR-103 improves insulin-stimulated glucose uptake (FIG. 7h)

| | 14C-labeled glucose uptake in primary adipocytes | | | | |
|---|---|---|---|---|---|
| | SC anti-mm-107 | SC anti-miR-103 | V anti-mm-107 | V anti-miR-103 | V PBS |
| No Insulin | 1.00 | 1.12 | 1.00 | 1.63 | 0.82 |
| 20 nM Insulin | 1.27 | 1.78 | 1.29 | 2.61 | 1.05 |

SC: p < 0.01 in no insulin, anti-miR-103 relative to anti-mm-107
SC: p < 0.001 in 20 nM insulin, anti-miR-103 relative to anti-mm-107
V: p < 0.001 in no insulin, anti-miR-103 relative to anti-mm-107
V: p < 0.01 in 20 nM insulin, anti-miR-103 relative to anti-mm-107

Furthermore, adiponectin levels, which positively correlate with the insulin sensitivity, were increased in anti-miR-103 treated ob/ob mice (Table 42), and decreased in C57Bl/6 mice injected with ad-107/GFP.

TABLE 42

Anti-miR-103 increases adiponectin levels in ob/ob mice

| Treatment | Strain | Adiponectin ug/ml |
|---|---|---|
| anti-mm-107 | ob/ob | 6.20 |
| anti-miR-103 | ob/ob | 8.11 |
| ad-GFP | C57Bl/6 | 8.98 |
| ad-107/GFP | C57Bl/6 | 6.79 |

Together, these data demonstrate that silencing of miR-103/107 increases insulin sensitivity in adipocytes.

Example 10 miR-103-Mediated Lipoprotein Lipase Hydrolase Activity

LPL hydrolase activity in the fat of C57Bl/6 or ob/ob mice treated with PBS or anti-miR-103 was measured using an enzymatic assay. An increase in LPL hydrolase activity in the anti-miR-103 treated mice indicated an increase in insulin sensitivity. See Table 43.

TABLE 43

Anti-miR-103 treatment increases LPL activity

| | c57bl/6 | ob/ob |
|---|---|---|
| anti-mm-107 | 0.34 | 0.22 |
| anti-miR-103 | 0.38 | 0.31* |

Increased insulin sensitivity results in improved insulin resistance. Accordingly, provided herein are methods for increasing insulin sensitivity, thus improving insulin resistance, by inhibiting the activity of miR-103 and or miR-107.

Example 11

Effects of miR-103 Inhibition Mice Lacking the Caveolin1 Gene

Cav1 is the principal protein of caveolae, distinct nonionic detergent-insoluble, lipid- and cholesterol-enriched vascular invaginations at the plasma membrane. Cav1 activates insulin signaling most likely by stabilizing caveolae and its associated IR. Specifically, peptides corresponding to the scaffolding domain derived from Cav-1 and -3, potently stimulate insulin receptor kinase activity toward insulin receptor substrate-1 (IRS-1). Cav3 overexpression augments insulin-stimulated phosphorylation of IRS-1 in 293T cells and increases hepatic IR phosphorylation in response to insulin stimulation, thereby improving overall glucose metabolism of diabetic mice. Cav1 null (Cav1 KO) mice are phenotypically normal on a chow diet. However, when placed on high fat diet they develop insulin resistance due to diminished IR signaling, as evidenced by a 90% decrease in total fat IR protein levels. We investigated if the activity of insulin signaling correlated with miR-103/107 mediated changes in Cav1 expression. In adipocytes of ob/ob mice, silencing of miR-103/107 using anti-miR-107 resulted in increased Cav1 protein levels (FIG. 8C), augmented IRb expression as well as enhanced pAkt levels compared to anti-mm-107 treated mice (FIG. 8C). In contrast, wild-type mice in which ad-107/GFP was injected into the peritoneal fat 8 days prior to the analysis exhibited a reduction in Cav1 expression and decreased IRb and pAKT levels (FIG. 8B; relative Cav1 expression of 0.4 following ad-107/GFP injection v. ad-GFP injection). Since overexpression of miR-107 in the liver by recombinant adenovirus led to hepatic insulin resistance and impaired glucose tolerance, downstream molecular insulin signaling events in those animals were studied. Protein levels of Cav1 and pAKT levels were diminished in the liver of wildtype mice infected with ad-107/GFP, with no changes observed in IRb protein levels (FIG. 8A). This result is in agreement with the phenotypic findings showing that overexpression of miR-103 can induce hepatic insulin resistance and data from Cav1 KO mice, which do not exhibit reduced IRb levels in the liver but have reduced IRb and pAkt levels in adipocytes. Lastly, in order to show that modulation of Cav1 expression is responsible for the increase in insulin signaling upon miR-103/107 silencing, high-fat fed obese mice or Cav1 KO mice were treated with anti-miR-103 or anti-mm-107 (15 mg/kg anti-miR, once per day intraperitoneally, for 2 consecutive days) to study the activation of insulin signaling following insulin stimulation. Whereas silencing of miR-103/107 in fat of high-fat fed obese wild-type littermates of the CAV1 KO mice led to increased expression of IRb, phosphorylated IRb and phospho-Akt compared to anti-mm-107 treated mice, no activation of insulin signaling was observed in the fat of high-fat fed obese Cav1 KO mice that were treated with anti-miR-103 (FIG. 8D). Together, these data demonstrate that miR-103/107 regulates insulin sensitivity through a caveolin-mediated process.

Example 12

Experimental Methods

Statistical analysis All bars show mean±STD, except Table 10 where bars show mean±STE. Significance was calculated using students t-test ($p<0.05$; $p<0.01$; $p<0.001$). Throughout the examples, unless otherwise indicated, statistical significance is indicated in the Tables: *=$p<0.05$; =$p<0.01$; *=$p<0.001$.

RNA isolation and Northern blotting analysis Total RNA was isolated using the Trizol reagent (Invitrogen). 5-30 µg RNA was separated at 15 W on 14% polyacrylamide gels as described Krutzfeldt et al., Nature, 2005, 438, 685-689.

Real Time PCR 2 µg of total RNA was used for cDNA preparation with random hexamer primers using Super Script III Reverse Transcriptase (Invitrogen). Steady state mRNA expression was measured by quantitative real-time PCR using the LightCycler 480 SYBR Green Master I Mix (Roche) with a Mx3005P Real Time PCR System (Stratagene). Transcript levels were normalized to GAPDH or 36B4. Primer sequences for real-time PCRs are available on request. MiRNA levels were measured using the TaqMan microRNA Assays for miR-103, mir-107, or U6 (Applied Biosystems) and PCR results were normalized to U6 levels.

Assay of luciferase activity Mouse or human 3' UTR sequences were PCR-amplified with specific primers, followed by attB adapter PCR, and cloned in the pDONR221 entry vector using BP Clonase (Invitrogen). The positive clones were then further cloned behind the stop codon of the firefly luciferase in the dual renila/firefly Luciferase pEM393 destination vector. HEK-293 cells were cultured in 24-well plates and each well was transfected with 100 ng of the final construct together with either PBS, or 50 nmol of either control or si-103 double-strand siRNA (Sigma) in quadruplicates. Cells were harvested and assayed 42-48 h after transfection using the Dual-Luciferase Reporter Assay System (Promega). Results normalized to the renilla luciferase control and expressed relative to the average value of the control PBS.

Animals All animal models were maintained in a C57BL/6 background on a 12-h light/dark cycle in a pathogen-free animal facility. Six-eight week-old wt, or leptin-deficient (ob/ob), or 12 weeks old high fat diet (DIO) mice fed for 8 weeks with 60% fat (Pvolimi Kliba AG) were injected in the tail-vein with either PBS, anti-miRs, ad-GFP, or ad-107/GFP (as indicated). Anti-miRs were administered at doses of 15 mg per kg body weight in 0.2 ml per injection on 2 consecutive days. Mice were injected with adenoviruses at $5 \times 10^9$ plaque-forming units (PFU) in 0.2 ml PBS through the tail vein.

Generation of recombinant adenovirus The recombinant adenovirus used to express miR-107 and GFP (Ad-107/GFP) was generated by inserting the PCR amplified miRNA precursor sequence with primers: 5'-AATAC-CCGCATGGAAGCAGGCTAA-3' (SEQ ID NO: 17) and 5'-AACATGTCTCAAGGAGAGGACGGT-3' (SEQ ID NO: 18) sinto a GFP expressing shuttle vector Ad5CMV K—NpA. Ad-GFP (ViraQuest), which does not contain a transgene was used as a control.

Adenovirus fat injection Ad-GFP or ad-107/GFP was injected in the peritoneal fat at a concentration of $1 \times 10^9$ pfu in 40 µl PBS following surgical exposure.

Computer Tomography Subcutaneous and visceral fat pads were scanned using an animal CT-Scanner (LaTheta). Images were corrected and analyzed using the LaTheta Software.

Isolation of stromal-vascular (SV) fraction and primary adipocytes Primary adipocytes and (SV) fraction from subcutaneous and visceral fat were prepared as described previously (Hansen et al., Mol. Endocrinol., 1998, 12, 1140-1149 and Tozzo et al., Am. J. Physiol., 1995, 268, E956-

964. Adipocyte differentiation was induced with insulin, dexamethasone, isobutylmethylxanthine and rosiglitazone when SV cells were 80% confluent (Tozzo et al.). Cells were treated using anti-miRs at a concentration of 5.5 µg/during the induction period on days 2 and 3.

Automated analysis of adipocyte differentiation Differentiated cells were fixed with 5% formaldehyde prior to staining with BODIPY for lipid droplets, Hoechst for nuclei and Syto60 for cytosolic staining (Invitrogen). 25 pictures per well were taken with an automated microscope imaging system (CellWorx). Pictures were analyzed using Cell Profiler Software.

Glucose uptake [$^{14}$C] spiked glucose uptake with or without 20 nM insulin stimulation was measured as described (Tozzo et al.).

Adipocyte size Hemotoxylin and eosin staining of 10 µm slices 5% paraformaldehyde fixed adipose tissue was performed according to standard procedures (for example, Chen and Farese, J. Lipid. Res., 2002, 43, 986-989), and images were analyzed using Cell Profiler Software. At least 2000 adipocytes were measured per animal to determine adipocyte size.

Glucose, Insulin, Cholesterol, TGs and NEFA measurements Blood glucose values were measured using an automated glucose monitor (Glucometer Elite, Bayer). Insulin was measured from plasma using Sensitive Rat Insulin RIA Kit (Linco). Cholesterol and TAGs were measured with Chol, or Trig/GB reagents respectively with c.f.a.s. as standard (Roche/Hitachi). NEFA were quantified with NEFA-HR (2) R1/R2 Set (Wako).

Glucose, Insulin, and Pyruvate Tolerance Tests Glucose, insulin or pyruvate tolerance tests were performed by i.p. injection of either glucose (2 g/kg of body weight in saline); insulin (0.75 unit/kg body weight); or pyruvate (2 g/kg of body weight in saline) respectively, after overnight fast (as indicated in the figures) for glucose and pyruvate, or 6 h fast for insulin. Blood glucose levels were measured before (time=j) and 15, 30, 60, and 120 min after injection.

Cell culture, infection, and transfection Hepa1-6, 3T3-L1, or HEK293 cells were maintained in growth medium Dulbecco's modified Eagle's medium (Invitrogen) containing 4.5 g/liter glucose supplemented with 10% FBS and penicillin/streptomycin. Hepa1-6 and 3T3-L1 were kept on collagen-coated plates. Hepa1-6 were infected with ad-GFP, or ad-107/GFP at 1:1000 dilution of 5×10$^{10}$ PFU virus prep in growth medium for 36 h. HEK293 cells were transfected with anti-miRs at concentration of 5.5 µg/ml in growth medium, or with PBS, si-103, or si-141 using Lipofectamine 2000 (Invitrogen).

Western blotting and antibodies Cells were washed with ice cold PBS and extracted in lysis buffer (10 mM Tris-HCl, pH 8.0, 140 mM NaCl, 1% Triton X-100, 1 mM EDTA, and protease inhibitor cocktail (Roche)), and Halt phosphatase inhibitors (Thermo Scientific) at 4° C. Proteins were separated by 8-12% SDS-PAGE, transferred on nitrocellulose filters, and detected with the following antibodies: mouse monoclonal anti-y-tubulin (Sigma-Aldrich), rabbit polyclonals anti-insulin receptor b subunit (C-19):sc-711 (IRb); anti-p-insulin receptor b subunit (Tyr1162/1163): sc25103 (p-IRb); anti-Caveolin 1 (N20):sc-894; and anti-GM103 (Bl0):sc-55591 (Santa Cruz Biotechnology); anti-p-AKT, anti-AKT, anti-p-S6BP; anti-p-GCK3 (Cell Signaling).

Sucrose density gradient fractionation and insulin stimulation Ad-GFP, or ad-107/GFP infected Hepa1-6 cells were serum starved for 12 h in Dulbecco's modified Eagle's medium without fetal bovine serum, stimulated or not with 500 nM insulin in growth medium for 15 min., scraped in ice cold PBS and resuspended in 1.5 ml homogenization buffer containing 250 mM sucrose, 4 mM HEPES pH 7.4, and protease and Halt phosphatase inhibitors (Thermo Scientific). Cell suspension was dounced in tight douncer for 25 times, and the perinuclear supernatant (PNS) after 10 min at 1000 rpm was loaded from the top on 0.4-2 M continuous sucrose density gradients (for example, Ort et al., Eur. J. Cell Biol., 2000, 79, 621-630), and centrifuged with Beckman ultracentrifuge for 18 h at 25000 rpm (100000 g) on 4° C. For the flotation gradient experiments, the PNS was mixed 1:1 with 85% sucrose, and 1 ml of the mix was loaded from the bottom on discontinuous sucrose gradient to the final 5% (2 ml), 30% (5 ml), and 42.5% (1 ml) sucrose and centrifuged 19 h at 39000 RPM in SW41 rotor using Beckman ultracentrifuge at 4° C. 0.5 ml fractions were collected from the top, precipitated with 1.5 volumes of ethanol overnight on −80° C., washed with 70% ethanol and resuspended in 2×SDS containing loading buffer.

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of reducing blood glucose in a subject in need thereof comprising administering to the subject a compound comprising modified oligonucleotide having a nucleobase sequence at least 90% complementary to nucleobases 1-21 of SEQ ID NO: 1 (miR-103) or nucleobases 1-21 of SEQ ID NO: 2 (miR-107), wherein the modified oligonucleotide consists of 12 to 30 linked nucleosides.

2. The method of claim 1, wherein the subject has at least one metabolic disorder selected from pre-diabetes, diabetes, metabolic syndrome, obesity, diabetic dyslipidemia, hyperlipidemia, hypertension, hypertriglyceridemia, hyperfattyacidemia, and hyperinsulinemia.

3. The method of claim 1, comprising measuring the blood glucose level of the subject.

4. The method of claim 1, comprising administering at least one additional therapy, wherein the at least one additional therapy is a glucose-lowering agent or a lipid-lowering agent.

5. The method of claim 1, wherein the nucleobase sequence of the modified oligonucleotide is 100% complementary to the nucleobase sequence of miR-103 (SEQ ID NO: 1) and is 100% complementary to the nucleobase sequence of miR-107 (SEQ ID NO: 2).

6. The method of claim 1, wherein the modified oligonucleotide comprises at least one modified sugar.

7. The method of claim 6, wherein the modified sugar is independently selected from a 2'-O-methoxyethyl sugar, a 2'-fluoro sugar, 2'-O-methyl sugar, and a bicyclic sugar moiety.

8. The method of claim 1, wherein the modified oligonucleotide comprises at least one modified internucleoside linkage.

9. The method of claim 8, wherein the modified internucleoside linkage is a phosphorothioate internucleoside linkage.

10. The method of claim 1, wherein each internucleoside linkage of the modified oligonucleotide is a modified internucleoside linkage.

11. The method of claim 10, wherein each internucleoside linkage is a phosphorothioate internucleoside linkage.

12. The method of claim 1, wherein the subject, prior to administration of the compound, was determined to have an increased level of miR-103 or miR-107.

13. The method of claim 12, wherein the subject has at least one metabolic disorder.

14. The method of claim 13, wherein at least one metabolic disorder is selected from pre-diabetes, diabetes, metabolic syndrome, obesity, diabetic dyslipidemia, hyperlipidemia, hypertension, hypertriglyceridemia, hyperfattyacidemia, and hyperinsulinemia.

15. The method of claim 1, wherein the modified oligonucleotide consists of 15 linked nucleosides.

16. The method of claim 1, wherein the modified oligonucleotide consists of 16 linked nucleosides.

17. The method of claim 1, wherein the modified oligonucleotide consists of 17 linked nucleosides.

18. The method of claim 1, wherein the modified oligonucleotide consists of 18 linked nucleosides.

19. The method of claim 1, wherein the modified oligonucleotide consists of 19 linked nucleosides.

20. The method of claim 1, wherein the modified oligonucleotide consists of 20 linked nucleosides.

21. The method of claim 1, wherein the modified oligonucleotide consists of 21 linked nucleosides.

* * * * *